United States Patent
Ambati et al.

(10) Patent No.: US 11,602,535 B2
(45) Date of Patent: *Mar. 14, 2023

(54) COMPOSITIONS AND METHODS FOR TREATING RETINAL DEGRADATION

(71) Applicant: University of Kentucky Research Foundation, Lexington, KY (US)

(72) Inventors: Jayakrishna Ambati, Lexington, KY (US); Benjamin Fowler, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 125 days.

This patent is subject to a terminal disclaimer.

(21) Appl. No.: 17/116,755

(22) Filed: Dec. 9, 2020

(65) Prior Publication Data

US 2021/0085681 A1    Mar. 25, 2021

Related U.S. Application Data

(63) Continuation of application No. 16/361,810, filed on Mar. 22, 2019, now Pat. No. 10,864,212, which is a continuation of application No. 15/142,087, filed on Apr. 29, 2016, now Pat. No. 10,300,057, which is a continuation of application No. 14/450,000, filed on Aug. 1, 2014, now Pat. No. 9,326,983.

(60) Provisional application No. 61/861,290, filed on Aug. 1, 2013, provisional application No. 61/987,612, filed on May 2, 2014.

(51) Int. Cl.

| | | |
|---|---|---|
| *A01N 43/04* | (2006.01) |
| *A61K 31/70* | (2006.01) |
| *A61K 31/506* | (2006.01) |
| *A61K 31/513* | (2006.01) |
| *A61K 31/7072* | (2006.01) |
| *A61K 31/7076* | (2006.01) |
| *A61K 31/52* | (2006.01) |
| *A61K 31/7064* | (2006.01) |
| *A61K 31/7052* | (2006.01) |
| *A61K 31/706* | (2006.01) |
| *A61K 31/7068* | (2006.01) |
| *C07D 405/04* | (2006.01) |
| *C07D 411/04* | (2006.01) |
| *A61P 25/16* | (2006.01) |
| *A61P 25/28* | (2006.01) |

(52) U.S. Cl.
CPC .......... *A61K 31/506* (2013.01); *A61K 31/513* (2013.01); *A61K 31/52* (2013.01); *A61K 31/706* (2013.01); *A61K 31/7052* (2013.01); *A61K 31/7064* (2013.01); *A61K 31/7068* (2013.01); *A61K 31/7072* (2013.01); *A61K 31/7076* (2013.01); *C07D 405/04* (2013.01); *C07D 411/04* (2013.01); *A61P 25/16* (2018.01); *A61P 25/28* (2018.01)

(58) Field of Classification Search
None
See application file for complete search history.

(56) References Cited

U.S. PATENT DOCUMENTS

| | | |
|---|---|---|
| 5,496,935 A | 3/1996 | Matthes et al. |
| 6,914,054 B2 | 7/2005 | Sommadossi et al. |
| 8,809,517 B2 | 8/2014 | Ambati |
| 9,326,983 B2 | 5/2016 | Ambati et al. |
| 9,453,226 B2 | 9/2016 | Ambati et al. |
| 9,464,289 B2 | 10/2016 | Ambati |
| 9,707,235 B1 | 7/2017 | Ambati |
| 10,300,057 B2 | 5/2019 | Ambati et al. |
| 10,864,212 B2 | 12/2020 | Ambati et al. |
| 11,219,623 B2 | 1/2022 | Ambati et al. |
| 2010/0226931 A1 | 9/2010 | Valiante et al. |
| 2014/0324357 A1 | 10/2014 | Halliday et al. |
| 2014/0342357 A1 | 11/2014 | Ambati |
| 2015/0038446 A1 | 2/2015 | Ambati et al. |
| 2016/0009810 A1 | 1/2016 | Ambati |
| 2016/0263114 A1 | 9/2016 | Ambati et al. |
| 2018/0044327 A1 | 2/2018 | Ambati et al. |
| 2019/0255049 A1 | 8/2019 | Ambati et al. |
| 2019/0262341 A1 | 8/2019 | Ambati et al. |

FOREIGN PATENT DOCUMENTS

| | | |
|---|---|---|
| EP | 0311100 A2 | 4/1989 |
| JP | 63-250396 | 4/1987 |
| WO | WO-2011/153234 A2 | 12/2011 |
| WO | WO-2013/012806 A2 | 1/2013 |
| WO | WO-2014/160336 A1 | 10/2014 |

OTHER PUBLICATIONS

Morgan et al. Cancer Chemother. Pharmacol. (2003), vol. 51, pp. 459-464.*
Weaver et al., "The design and synthesis of nucleoside triphosphate isoteres as potential inhibitors of HIV reverse transcriptase", Tetrahedron, 53, pp. 5537-5562, Mar. 26, 1998 (Mar. 26, 1998).
Goulaouic et al., "N- versus O-Alkylation of 2,3'-Anhydrothymidine: Reaction of the obtained Pyrimidinium Salts with Azide Ions", Journal of Organic Chemistry, 58, pp. 3030-3037, May 21, 1993 (May 21, 1993).
Verheyden et al., "Halo Sugar Nucleosides. IV. Synthesis of Some 4',5'-Unsaturated Pyrimidine Nucleosides", Journal of Organic Chemistry, 39, pp. 3273-3579, Nov. 1, 1974 (Nov. 1, 1974).
Abdul-Sater et al., "Inflammasome-Dependent Caspase-1 Activation in Cervical Epithelial Cells Stimulates Growth of the Intracellular Pathogen Chlamydia Trachomatis," The Journal of Biological Chemistry, 284(39): 26789-26796 (2009).

(Continued)

*Primary Examiner* — Patrick T Lewis
(74) *Attorney, Agent, or Firm* — Stites & Harbison PLLC; Mandy Wilson Decker

(57) ABSTRACT

The present disclosure relates to compositions and methods for treating retinal damage and/or retinal degradation. More specifically, this disclosure relates to methods for treating degradation of the retinal pigment epithelium by administering compositions comprising a nucleoside and/or a nucleoside or nucleotide reverse transcriptase inhibitor.

20 Claims, 35 Drawing Sheets

(56) References Cited

OTHER PUBLICATIONS

Abulafia et al., "Inhibition of the inflammasome complex reduces the inflammatory response after thromboembolic stroke in mice," Journal of Cerebral Blood Flow & Metabolism, 29: 534-544 (2009).
Adamczak et al., "Inflammasome Proteins in Cerebrospinal Fluid of Brain Injured Patients are Biomarkers of Functional Outcome," J Neurosurg., 117(6): 1119-1125 (2012).
Adinolfi et al., "Basal Activation of the P2X7 ATP Receptor Elevates Mitochondrial Calcium and Potential, Increases Cellular ATP Levels, and Promotes Serum-Independent Growth," Mol Biol Cell, 16: 3260-3272 (2005).
Adinolfi et al., "Expression of P2X7 Receptor Expression in Evolutive and Indolent Forms of Chronic B Lymphocytic Leukemia," Blood, 99(2): 706-708 (2002).
Agarwal et al., "Emtricitabine Prodrugs with Improved Anti-HIV Activity and Cellular Uptake," Molecular Pharmaceutics, 10(2): 467-476 (2013).
Agarwal et al., "Synthesis and Biological Evaluation of Fatty Acyl Ester Derivatives of 2',3'-didehydro-2'3'-dideoxythymidine," Bioorg Med Chem Lett, 21: 1917-1921 (2011).
Ahmad et al., "Elevated Levels of circulating Interleukin-18 in Human Immunodeficiency Virus-Infected Individuals: Role of Peripheral Blood Mononuclear Cells and Implications for AIDS Pathogensis," J Virol, 76: 12448-12456 (2002).
Aksentijevich et al., "The Clinical Continuum of Cryopyrinopathies: Novel CIAS1 Mutations in North American Patients and a New Cryopyrin Model," Arthritis Rheum, 56(4): 1273-1285 (2007).
Alcocer-Gomez et al., "NLRP3 Inflammasome: A New Target in Major Depressive Disorder," CNS Neuroscience & Therapeutics, 20: 294-295 (2014).
Amaral et al., "NLRP3 Inflammasome-Mediated Neutrophil Recruitment and Hypernociception Depend on Leukotriene B4 in a Murine Model of Gout," Arthritis & Rheumatism, 64(2): 474-484 (2012).
Ambati et al., "Age-related Macular Degeneration: Etiology, Pathogenesis, and Therapeutic Strategies," Surv Ophthalmol, 48: 257-293 (2003).
Ambati et al., "Mechanisms of Age-Related Macular Degeneration," Neuron, 75: 26-39 (2012).
Andersen et al., "Replication Across Regioisomeric Ethylated Thymidine Lesions by Purified DNA Polymerases," Chemical Research in Toxicology, 26(11): 1730-1738 (2013).
Andersen et al., "The NLRP3/ASC inflammasome promotes T-cell-dependent immune complex glomerulonephritis by canonical and noncanonical mechanisms," Kidney International, 86: 965-978 (2014).
Anderson et al., "Plasma-borne indicators of inflammasome activity in Parkinson's disease patients," Parkinson's Disease, 7(Article No. 2): 1-12 (2021).
Armstrong et al., "Diagnosis and treatment of Parkinson disease: a review," JAMA, 323(6):548-580 (2020).
Artlett et al., "The Inflammasome Activating Caspase-1 Mediates Fibrosis and Myofibroblast Differentiation in Systemic Sclerosis," Arthritis and Rheumatism, 63(11): 3563-3574 (2011).
Ather et al., "Serum Amyloid A (SAA) Activates the NLRP3 Inflammasome and Promotes TH17 Allergic Asthma in Mice," J Immunol, 187(1): 64-73 (2011).
Babelova et al., "Biglycan, a Danger Signal that Activates the NLRP3 Inflammasome via Toll-like and P2X Receptors*," The Journal of Biological Chemistry, 284(36): 24035-24048 (2009).
Babolin et al., "TpF1 from Treponema Pallidum Activates Inflammasome and Promotes the Development of Regulatory T Cells," The Journal of Immunology, 187:1377-1384 (2011).
Bakker et al., "A Tissue-Specific Role for Nlrp3 in Tubular Epithelial Repair after Renal Ischemia/Reperfusion," The American Journal of Pathology, 184(7): 2013-2022 (2014).
Baldini et al., "The P2X7 receptor-inflammasome complex has a role in modulating the inflammatory response in primary Sjögren's syndrome," Journal of Internal Medicine, 274: 480-489 (2013).
Balzarini et al., "Differential Patterns of Intracellular Metabolism of 2',3'-didehydro-2'3'-dideoxythymidine and 3'-azido-2',3'-dideoxythymidine, Two Potent Anti-Human Immunodeficiency Virus Compounds," J Biol Chem, 264: 6127-6133 (1989).
Bank, "Characteristics of compounds that cross the blood-brain barrier," BMC Neurology, 9(Suppl 1):S3 (2009).
Basso et al., "Behavioral Profile of P2X7 Receptor Knockout Mice in Animal Models of Depression and Anxiety: Relevance for Neuropsychiatric Disorders," Behavioral Brain Research, 198: 83-90 (2009).
Batzer et al., "Alu Repeats and Human Genomic Diversity," Nature Review Genetics, 3:370-379 (2002).
Bauer et al., "Colitis induced in mice with dextran sulfate sodium (DSS) is mediated by the NLRP3 inflammasome," Gut, 59:1192e-1199 (2010).
Bennucci et al., "Effect of etanercept plus lamivudine in a patient with rheumatoid arthritis and viral hepatitis B," Journal of Clinical Rheumatology, 14(4):245-246 (2008).
Bernier., "Purinergic regulation of inflammasome activation after central nervous system injury," J Gen Physiol, 140(5): 571-575 (2012).
Besnard et al., "NLRP3 Inflammasome is required in murine asthma in the absence of aluminium adjuvant," Allergy, 66(8): 1047-1057 (2011).
Bonar et al., "Constitutively Activated NLRP3 Inflammasome Causes; Inflammation and Abnormal Skeletal Development in Mice," Plos One, 7(4): e35979 (2012).
Boucher et al., "Resilience and reduced c-Fos expression in P2X7 receptor knockout mice exposed to repeated forced swim test," Neuroscience, 189:170-177 (2011).
Bringmann et al., "Upregulation of P2X7 Receptor currents in Muller glial cells during proliferative vitreoretinopathy," Investigative Ophthalmology & Visual Science, 42(3):860-867 (2001).
Brydges et al., "Divergence of IL-1, IL-18, and cell death in NLRP3; inflammasomopathies," J Clin Invest, 123(11): 4695-4705 (2013).
Cabrini et al., "A His-155 to Tyr polymorphism confers gain-of-function to the human P2X7 receptor of human leukemic lymphocytes," The Journal of Immunology, 175:82-89 (2005).
Cario-Toumaniatz et al., "P2X7 Receptor Activation-induced contraction and lysis in human saphenous vein smooth muscle," Circulation Res, 83:196-203 (1998).
Case et al., "Caspase-11 stimulates rapid flagellin-independent pyroptosis in response to Legionella pneumophila," PNAS, 110(5): 1851-1856 (2013).
Chakraborty et al., "Inflammasome Signaling at the Heart of Central Nervous System Pathology," Journal of Neuroscience Research, 88:1615-1631 (2010).
Chang et al., "Inhibition of the P2Z7 receptor reduces cystogenesis in PKD," J Am Soc Nephrol,22:1696-1706 (2011).
Cheewatrakoolpong et al., "Identification and Characterization of Splice Variants of the Human P2X7 ATP Channel," Biochem Biophys Res Commun, 332: 17-27 (2005).
Chen et al., "Testing the role of P2X7 receptors in the development of type 1 diabetes in nonobese diabetic mice," The Journal of Immunology, 186:4278-4284 (2011).
Cheng et al., "Comparative efficacy of antiviral drugs on human ocular fibroblasts," Exp Eye Res, 61(4): 461-467 (1995).
Chi et al., "Caspase-8 promotes NLRP1/NLRP3 inflammasome; activation and IL-1? production in acute glaucoma," PNAS, 111(30): 11181-11186 (2014).
Chow et al., "NLRP3 promotes inflammation-induced skin cancer but is dispensable for asbestos-induced mesothelioma," Immunology and Cell Biology, 90: 983-986 (2012).
Churg et al., "The role of interleukin-1b in murine cigarette smoke-induced emphysema and small airway remodeling," Am J Respir Cell Mol Biol, 40:482-490 (2009).
Codolo et al., "Triggering of inflammasome by aggregated α-synuclein an inflammatory response in synucleinopathies," Plos One, 8(1):e55375 (2013).
Cohen et al., "A multicentre, double blind, randomised, placebo controlled trial of anakinra (Kineret), a recombinant interleukin 1 receptor antagonist, in patients with rheumatoid arthritis treated with background methotrexate," Ann Rheum Dis, 63:1062-1068 (2004).

(56) References Cited

OTHER PUBLICATIONS

Cruz et al., "ATP Activates a Reactive Oxygen Species-Dependent Oxidative Stress Response and Secretion of Proinflammatory Cytokines in Macrophages," J Biol Chem, 282: 2871-2879 (2007).
Csak et al., "Fatty Acid and Endotoxin Activate Inflammasomes in Mouse Hepatocytes that Release Danger Signals to Stimulate Immune Cells," Hepatology, 54: 133-144 (2011).
Csolle et al., "The absence of P2X7 receptors (P2rx7) on non-haematopoietic cells leads to selective alteration in mood-related behaviour with dysregulated gene expression and stress reactivity in mice," International Journal of Neuropsychopharmacology, 16:213-233 (2013).
Cuisset et al., "Mutations in the autoinflammatory cryopyrin-associated periodic syndrome gene: epidemiological study and lessons from eight years of genetic analysis in France," Ann Rheum Dis, 70: 495-499 (2011).
David et al., "IL-18 Underexpression Reduces IL-2 Levels During HIV Infection: A Critical Step Towards the Faulty Cell-Mediated Immunity?" Aids, 14: 2212-2214 (2000).
Davis et al., "The Inflammasome NLRs in Immunity, Inflammation, and Associated Diseases," Annu Rev Immunol, 29: 707-735 (2011).
Dell'antonio et al., "Relief of Inflammatory pain in rats by local use of the selective P2X7 ATP receptor inhibitor, oxidized ATP," Arthritis & Rheumatism, 46(12):3378-3385 (2002).
Deplano et al., "P2X7 receptor-mediated Nlrp3-infammasome activation is a genetic determinant of macrophage-dependent crescentic glomerulonephritis," Journal of Leukocyte Biology, 93:127-134 (2013).
Dewannieux et al., "LINE-mediated Retrotransposition of Marked Alu Sequences," Nature Genetics, 35:41-48 (2003).
Dhimolea, "Interleukin-1B inhibitors for the treatment of cyropyrin-associated periodic syndrome," The Application of Clinical Genetics. 4:21-27 (2011).
Diaz-Hernandez et al., "Altered P2X7-receptor level and function in mouse models of Huntington's disease and therapeutic efficacy of antagonist administration," The FASEB Journal, 23(6):1893-1906 (2009).
Diaz-Hernandez et al., "In vivo P2X7 inhibition reduces amyloid plaques in Alzheimer's disease through GSK3 and secretases," Neurobiology of Aging, 33:1816-1828 (2012).
Dixit, "Nlrp3 Inflammasome Activation in Type 2 Diabetes: Is It Clinically Relevant?," Diabetes, 62: 22-24 (2013).
Dostert et al., "Innate Immune Activation through Nalp3 inflammasome sensing of asbestos and silica," Science, 320(5876):674-677 (2008).
Dridi et al., "ERK1/2 Activation is a Therapeutic Target in Age-related Macular Degeneration," Proc Natl Acad Sci USA, 109: 13781-13786 (2012).
Duewell et al., "NLRP3 inflammasomes are required for atherogenesis and activated by cholesterol crystals," Nature, 464:1357-1362 (2010).
Edwards et al., "Nonpeptidic inhibitors of human neutrophil elastase. 7. Design, synthesis, and in vitro activity of a series of pyridopyrimidine trifluoromethyl ketones," Journal of medicinal chemistry, 39(5):1112-1124 (1996).
Eltom et al., "P2X7 receptor and caspase 1 activation are central to airway inflammation observed after exposure to tobacco smoke," PLOS One, 6(9):1-11 (2011).
Esposito et al., "Role of FAP48 in HIV-associated lipodystrophy," Journal of Cellular Biochemistry, 113(11): 3446-3454 (2012).
Extended European Search Report for EP Application No. 16756477 dated Jun. 26, 2018.
Fann et al., "Intravenous immunoglobulin suppresses NLRP1 and NLRP3 inflammasome-mediated neuronal death in ischemic stroke," Cell Death and Disease, 4:e790 (2013).
Ferrara et al., "Graft-versus-host Disease," Lancet, 373: 1550-1561 (2009).
Fourie et al., "Percutaneous delivery of carbamazepine and selected N-alkyl and N-hydroxyalkyl analogues," International Journal of Pharmaceutics, 279(1-2):59-66 (2004).
Fowler et al., "Nucleoside Reverse Transcriptase Inhibitors are Anti-Inflammatory and Target Dry Age-Related Macular Degeneration," University of Kentucky Uknowledge; Theses and Disserations—Physiology; pp. 1-115 (2014).
Fowler et al., "Nucleoside Reverse Transcriptase Inhibitors Possess Intrinsic Anti-Inflammatory Activity," Science, 346: 6212, 1000-1003 (2014).
Franchi et al., "The inflammasome: a caspase-1-activation platform that regulates immune responses and disease pathogenesis," Nature Immunology, 10: 241-247 (2009).
Franklin et al., "ASC has extracellular and prionoid activities that propagate inflammation," Nat Immunol, 15(8): 727-737 (2014).
Freeman et al., "Alpha-Synuclein Induces Lysosomal Rupture and Cathepsin Dependent Reactive Oxygen Species Following Endocytosis," PLOS One, 8(4): e62143 (2013).
Fulgenzi et al., "Periodate oxidized ATP (oATP) reduced hyperalgesia in mice: Involvement of P2X7 receptors and implications for therapy," International Journal of Immunopathology and Pharmacology, 21(1):61-71 (2007).
Furlan-Freguia et al., "P2X7 receptor signaling contributes to tissue factor-dependent thrombosis in mice," The Journal of Clinical Investigation, 121(7):2932-2944 (2011).
Furst, "Review of recombinant human interleukin-I receptor antagonist in the treatment of rheumatoid arthritis," Clinical Therapeutics, 26(12):1960-1975 (2004).
Garcia-Marcos et al., "Role of Sodium in Mitochondrial Membrane Depolarization Induced by P2X7 Receptor Activation in Submandibular Glands," FEBS Lett, 579: 5407-5413 (2005).
Gartland et al., "Blockade of the pore-forming P2X7 receptor inhibits formation of multinucleated human osteoclasts in vitro," Calcified Tissue International, 73:361-369 (2003).
Gasse et al., "IL-1R1/MyD88 signaling and the inflammasome are essential in pulmonary inflammation and fibrosis in mice," The Journal of Clinical Investigation, 117(12):3786-3799 (2007).
Gasse et al., "Uric Acid Is a Danger Signal Activating NALP3 Inflammasome in Lung Injury Inflammation and Fibrosis," American Journal of Respiratory and Critical Care Medicine, 179: 903-913 (2009).
Glinskii et al., "Identification of intergenictrans-regulatory RNAs containing a disease-linked SNP sequence and targeting cell cycle progression/differentiation pathways in multiple common human disorders," Cell Cycle, 8(23): 3925-3942 (2009).
Goldback-Mansky et al., "Current status of understanding the pathogenesis and management of patients with NOMID/CINCA," Curr Rheurmatol Rep, 13(2):123-131 (2011).
Goosen et al., "Physicochemical characterization and solubility analysis of thalidomide and its N-alkyl analogs," Pharmaceutical Research, 19(1):13-19 (2002).
Goossens et al., "Expression of NLRP3 inflammasome and T cell population markers in adipose tissue are associated with insulin resistance and impaired glucose metabolism in humans," Molecular Immunology, 50:142-149 (2012).
Gordon et al., "Inflammasome inhibition prevents ?-synuclein pathology and dopaminergic neurodegeneration in mice," Sci. Transl. Med., 10(4066): 1-12 (2018).
Griffith et al., "Pure hemozoin is inflammatory in vivo and activates the NALP3 inflammasome via release of uric acid," The Journal of Immunology, 183:5208-5220 (2009).
Gris et al., "NLRP3 plays a critical role in the development of experimental autoimmune encephalomyelitis by mediating Th1 and Th17 responses," J Immunol, 185: 974-981 (2010).
Gross et al., "Syk kinase signalling couples to the Nlrp3 inflammasome for anti-fungal host defense," Nature, 459(21):433-436 (2009).
Guerra et al., "Purinergic receptor regulation of LPS-induced signaling and pathophysiology," Journal of Endotoxin Research, 9(4):256-263 (2003).
Gulbransen et al., "Activation of neuronal P2X7 receptor-pannexin-1 mediates death of enteric neurons during colitis," Nat Med, 18(4):600-604 (2012).
Gunther et al., "Neuroprotective effects of the P2 receptor antagonist PPADS on focal cerebral ischaemia-induced injury in rats," European Journal of Neuroscience, 23:2824-2828 (2006).

(56) References Cited

OTHER PUBLICATIONS

Hacker et al., "Deep brain stimulation in early-stage Parkinson disease," Neurology, 95(4): e393-e401 (2020).
Hattori et al., "Feasibility study of 616 melanoma therapy using oxidized ATP to target purinergic receptor P2X7," European Journal of Pharmacology, 695:20-26 (2012).
Hazleton et al., "Purinergic Receptors are Required for HIV-1 Infection of Primary Human Macrophages," J Immunol, 188: 4488-4495 (2012).
He et al., "MEFV E148Q polymorphism is associated with Henoch-Schönlein purpura in Chinese children," Pediatr Nephrol, 25:2077-2082 (2010).
He et al., "Spinal P2X7 receptor mediates microglia activation-induced neuropathic pain in the sciatic nerve injury rat model," Behavioural Brain Research, 226:163-170 (2012).
Henao-Mejia et al., "Inflammasome-mediate dysbiosis regulates progression of NAFLD and obesity," Nature 482(7384):179-185 (2012).
Heneka et al., "NLRP3 is activated in Alzheimer's disease and contributes to pathology in APP/PS1 mice," Nature, 493: 674-682 (2013).
Hentze et al., "Critical Role for Cathepsin 6 in Mediating Caspase-1-Dependent Interleukin-18 Maturation and Caspase-1-Independent Necrosis Triggered by the Microbial Toxin Nigericin," Cell Death Differ, 10: 956-968 (2003).
Hickey et al., "Available and emerging treatments for Parkinson's disease: a review," Drug Design, Development and Therapy, 5:241-254 (2011).
Hoffman et al., "Mutation of a new gene encoding a putative pyrin-like protein causes familial cold autoinflammatory syndrome and Muckle-Wells syndrome," Nat Genet, 29(3): 301-305 (2001).
Honore et al., "A-740003 [N-(1-{[(Cyanoimino)(5-quinolinylamino) methyl]amino-2,2-dimethylpropyl)-2-(3,4-dimethoxyphenyl)acetamide], a novel and selective P2X7 receptor antagonist, dose-dependently reduces neuropathic pain in the rat," The Journal of Pharmacology and Experimental Therapeutics, 319(3):1376-1385.
Hornung et al., "Silica crystals and aluminum salts mediate NALP-3 inflammasome activation via phagosomal destabilization," Nat Immunol, 9(8): 847-856 (2008).
Huang et al., "The Immune Factors Involved in the Pathogenesis, Diagnosis, and Treatment of Sjogren's Syndrome," Clinical and Developmental Immunology, 2013(Article ID 160491): 1-6 (2013).
Hugenschmidt et al., "The Cross-sectional and Longitudinal Associations of Diabetic Retinopathy With Cognitive Function and Drain MRI Findings: The Action to Control Cardiovascular Risk in Diabetes (ACCORD) Trial," Diabetes Care, 37: 3244-3252 (2014).
Humphreys et al., "Stress-activated Protein Kinase/JNK Activation and Apoptotic Induction by the Macrophage P2X7 Nucleotide Receptor," J Biol chem, 275: 26792-26798 (2000).
Hurelbrink et al., "Death of Dopaminergic Neurons in Vitro and in Nigral Grafts: Reevaluating the Role of Caspase Activation," Experimental Neurology, 171: 46-58 (2001).
Iannello et al., "HIV-1 Causes an Imbalance in the Production of Interleukin-18 and Its Natural Atagonist in HIV-Infected Individuals: Implications for Enhanced Viral Replication," J Infect Dis, 201:608-617 (2010).
Imagawa et al., "Safety and efficacy of canakinumab in Japanese patients with phenotypes of cryopyrin-associated periodic syndrome as established in the first open-label, phase-3 pivotal study (24-week results)," Clinical and Experimental Rheumatology, 31:302-309 (2013).
Inoue et al., "NLRP3 inflammasome induces chemotactic immune cell migration to the CNS in experimental autoimmune encephalomyelitis," PNAS, 109(26): 10480-10485 (2012).
International Search Report and Written Opinion for International Application No. PCT/US16/19852 dated May 3, 2016.
Ising et al., "NLRP3 inflammasome activation drives tau pathology," Nature, 575: 669-673 (2019).
Iyer et al., "Necrotic cells trigger a sterile inflammatory response through the Nlrp3 inflammasome," PNAS, 106(48): 20388-20393 (2009).
Jankovic et al., "The Nlrp3 Inflammasome Regulates Acute Graft-versus-host Disease," J Exp Med, 210: 1899-1910 (2013).
Jelassi et al., "Anthraquinone emodin inhibits human cancer cell invasiveness by antagonizing P2X7 receptors," Carcinogenesis, 34(7): 1487-1496 (2013).
Jelassi et al., "P2X7 receptor activation enhances SK3 channels-and cystein cathepsin-dependent cancer cells invasiveness," Oncogene, 30: 2108-2122 (2011).
Jeong et al., "Structure-Activity Relationships of .beta.-D-(2S,5R)- and .alpha.-D-(2s,5S)-1, 3-Oxathiolanyl Nucleosides as Potential Anti-HIV Agents," Journal of Medicinal Chemistry, 36(18):2627-2638 (1993).
Ji et al., "P2X7 deficiency Attenuates Hypertension and Renal Injury in Deoxycorticosterone Acetate-Salt Hypertension," Am J Physiol Renal Physiol, 303: F1207-F1215 (2012).
Ji et al., "P2X7 receptor antagonism attenuates the hypertension and renal injury in Dahl salt-sensitive rats," Hypertension Research, 35:173-179 (2012).
Jun et al., "; Extracellular ATP Mediates Necrotic Cell Swelling in SN4741 Dopaminergic Neurons through P2X7 Receptors," J Biol Chem, 282 (52): 37350-37358 (2007).
Kahlenberg et al., "Inflammasome Activation of IL-18 Results in Endothelial Progenitor Cell Dysfunction in Systemic Lupus Erythematosus," The Journal of Immunology, 187: 6143-6156 (2011).
Kahlenberg et al., "Mechanisms of Caspase-1 Activation by P2X7 Receptor-Mediated K+ Release," Am J Physiol Cell Physiol, 286: C1100-1108 (2004).
Kahlenberg et al., "Neutrophil Extracellular Trap-Associated Protein Activation of the NLRP3 Inflammasome Is Enhanced in Lupus Macrophages," J Immunol, 190: 1217-1226 (2013).
Kakkar et al., "Management of Parkinson's disease: Current and future pharmacotherapy," European Journal of Pharmacology, 750: 74-81 (2015).
Kakurai et al., "Involvement of P2X7 receptors in retinal ganglion cell death after optic nerve crush injury in rats," Neuroscience Letters, 534: 237-241 (2013).
Kalbitz et al., "Role of extracellular histones in the cardiomyopathy of sepsis," The FASEB Journal, 29: 2185-2193 (2015).
Kaneko et al., "DICER1 Deficit Induces Alu RNA Toxicity in Age-related Macular Degeneration," Nature, 471: 325-330 (2011).
Kawamura et al., "P2X7 Receptors Regulate NKT Cells in Autoimmune Hepatitis 1," Journal of Immunology, 176: 2152-2160 (2006).
Keating et al., "P2X7 Receptor-Dependent Intestinal Afferent Hypersensitivity in a Mouse Model of Postinfectious Irritable Bowel Syndrome," The Journal of Immunology, 187: 1467-1474 (2011).
Keller et al., "Thalidomide Inhibits Activation of Caspase-11," Journal of Immunology, 183: 5593-5599 (2009).
Kerns et al., "Drug-like properties: concepts, structure design and methods from ADME to toxicity optimization," Elsevier (2008).
Kerur et al., "TLR-lndependent and P2X7-Dependent Signaling Mediate Alu RNA-lnduced NLRP3 Inflammasome Activation in Geographic Atrophy," Invest Ophthalmol Vis Sci, 54: 7395-7401 (2013).
Killeen et al., "Signaling Through Purinergic Receptors for ATP Induces Human Cutaneous Innate and Adaptive Th17 Responses: Implications in the Pathogenesis of Psoriasis," The Journal of Immunology, 190: 4324-4336 (2013).
Killinger et al., "The vermiform appendix impacts the risk of developing Parkinson's disease," Sci Transl Med., 10(465): 1-32 (2018).
Kim et al., "NLRP3 Inflammasome Knockout Mice are Protected Against Ischemic but not Cisplatin-Induced Acute Kidney Injury," J Pharmacol Exp Ther, 346: 465-472 (2013).
Kimbler et al., "Activation of P2X7 Promotes Cerebral Edema and Neurological Injury After Traumatic Brain Injury in Mice," PLoS One, 7(7): 1-10 (2012).
Kobayashi et al., "Induction of the P2X7 Receptor in Spinal Microglia in a Neuropathic Pain Model," Neuroscience Letters, 504: 57-61 (2011).

(56) References Cited

OTHER PUBLICATIONS

Koo et al., "ESX-1-dependent cytolysis in lysosome secretion and inflammasome activation during mycobacterial infection," Cellular Microbiology, 10(9): 1866-1878 (2008).
Koo et al., "Evidence for IL-1 Receptor Blockade as a Therapeutic Strategy for the Treatment of Depression," Curr Opin Investing Drugs, 10(7): 664-671 (2009).
Kubes et al., "Reviews in Basic And Clinical Gastroenterology and Hepatology," Gastroenterology, 143: 1158-1172 (2012).
Kubes et al., "Sterile Inflammation in the Liver," Gastroenterology, 143: 1158-1172 (2012).
Kubota et al., "Cryopyrin-Associated Periodic Syndromes: Background and Therapeutics," Mod Rheumatol, 20: 213-221 (2010).
Kuemmerle-Deschner et al., "Canakinumab (ACZ885, a fully human IgG1 anti-IL-1b mAb) Induces Sustained remission in Pediatric Patients with Cryopyrin-Associated Periodic Syndrome (CAPS)," Arthritis Research and Therapy, 13(34): 1-10 (2011).
Labasi et al., "Absence of the P2X7 Receptor Alters Leukocyte Function and Attenuates an Inflammatory Response," The Journal of Immunology, 168: 6436-6445 (2002).
Lee et al., "Upregulated NLRP3 Inflammasome Activation in Patients with Type 2 Diabetes," Diabetes, 62: 194-204 (2013).
Lewis et al., "Mitochondrial Toxicity of NRTI Antiviral Drugs: An Integrated Cellular Perspective," Nat Rev Drug Discov, 2: 812-822 (2003).
Li et al., "Lewy bodies in grafted neurons in subjects with Parkinson's disease suggest host-to-graft disease propagation," Nature Medicine, 14(5): 501-503 (2008).
Li et al., "Mechanisms of ATP Release by Human Trabecular Meshwork Cells the Enabling Step in Purinergic Regulations of Aqueous Humor Outflow," J Cell Physiol, 227(1): 172-182 (2012).
Li et al., "MicroRNA-30e regulates neuroinflammation in MPTP model of Parkinson's disease by targeting Nlrp3," Human Cell, 31: 106-115 (2018).
Li et al., "Propionibacterium acnes Activates the NLRP3 Inflammasome in Human Sebocytes," Journal of Investigative Dermatology, 134: 2747-2756 (2014).
Liu et al., "Expression of the NLRP3 Inflammasome in Cerebral Cortex After Traumatic Brain Injury in a Rat Model," Neurochem Res, 38: 2072-2083 (2013).
Liu et al., "The role of inflammasome in Alzheimer's disease," Ageing Research Reviews, 15: 6-15(2014).
Lommatzsch et al., "Extracellular Adenosine Triphosphate and Chronic Obstructive Pulmonary Disease," Am J Respir Crit Care Med, 181, 928-934 (2010).
Lopez-Castejon et al., "P2X7 Receptor-Mediated Release of Cathepsins from Macrophages is a Cytokine-Independent Mechanism Potentially Involved in Joint Diseases," Journal of Immunology, 185: 2611-2619 (2010).
Lu et al., "Uncoupling protein 2 deficiency aggravates astrocytic endoplasmic reticulum stress and nod-like receptor protein 3 inflammasome activation," Neurobiology of Aging, 35: 421-430 (2014).
Lucattelli et al., "P2X7 Receptor Signaling in the Pathogenesis of Smoke-Induced Lung Inflammation and Emphysema," Am J Respir Cell Mol Biol, 44: 423-239 (2011).
Macri et al., "Serum levels of interleukin 1ß, interleukin 8 and tumour necrosis factor a as markers of gastric cancer," Biomarkers, 11(2): 184-193 (2006).
Manda et al., "Highly active antiretroviral therapy drug combination induces oxidative stress and mitochondrial dysfunction in immortalized human blood-brain barrier endothelial cells," Free Radical Biology & Medicine, 50:801-810 (2011).
Mansson et al., "NOD-like receptors in the human upper airways: a potential role in nasal polyposis," Allergy, 66: 621-628 (2011).
Mao et al., "Nitric Oxide Suppresses NLRP3 Inflammasome Activation and Protects Against LPS-Induced Septic Shock," Cell Research 23: 201-212 (2013).
Mao et al., "The NLRP3 Inflammasome is Involved in the Pathogenesis of Parkinson's Disease in Rats," Neurochem Res, 42:1104-1115 (2017).
Marcellino et al., "On the Role of P2X7 Receptors in Dopamine Nerve Cell Degeneration in a Rat Model of Parkinson's Disease: Studies with the P2X7 Receptor Antagonist A-438079," J Neural Transm, 117: 681-687 (2010).
Mariathasan et al., "Cryopyrin Activates the Inflammasome in Response to Toxins and ATP," Nature, 440: 228-232 (2006).
Mariathasan et al., "Differential Activation of the Inflammasome by Caspase-1 Adaptors ASC and Ipaf," Nature, 430: 213-218 (2004).
Martinon et al., "Gout-associated Uric Acid Crystals Activate the NALP3 Inflammasome," Nature, 440: 237-241 (2006).
Martinon et al., "The Inflammasome: A Molecular Platform Triggering Activation of Inflammatory Caspases and Processing of ProIL-Beta," Mol Cell, 10: 417-426 (2002).
Martinon et al., "The Inflammasomes: Guardians of the Body," Annu Rev Immunol, 27: 229-265 (2009).
Masters et al., "Activation of the NLRP3 Inflammasome by Islet Amyloid Polypeptide Provides a Mechanism for Enhanced IL-1b in type 2 Diabetes," Nature Immunology, 11(10): 897-905 (2010).
Masuda et al., "Syk Inhibitors as Treatment for Allergic Rhinitis," Pulmonary Pharmacology and Therapeutics, 21: 461-467 (2008).
Matute et al., "P2X7 Receptor Blockade Prevents ATP Excitotoxicity in Oligodendrocytes and Ameliorates Experimental Autoimmune Encephalomyelitis," The Journal of Neuroscience, 27(35): 9525-9533 (2007).
McClellan et al., "High-Mobility Group Box 1: A Novel Target for Treatment of Pseudomonas aeruginosa Keratitis," The Journal of Immunology, 194: 1776-1787 (2015).
McDonald et al., "Intravascular Danger Signals Guide Neutrophils to Sites of Sterile Inflammation," Science, 330: 362-366 (2010).
Minagar et al., "The role of macrophage/microglia and astrocytes in the pathogenesis of three neurologic disorders: HIV-associated dementia, Alzheimer disease, and multiple sclerosis," Journal of the Neurological Sciences, 202: 13-23 (2002).
Mishra et al., "Nitric Oxide Controls the Immunopathology of Tuberculosis by Inhibiting NLRP3 Inflammasome-Dependent Processing of IL-1," Nature Immunology, 14(1): 52-61 (2013).
Mittag et al., "Retinal Damage after 3 to 4 Months of Elevated Intraocular Pressure in a Rat Glaucoma Model," Invest Ophthalmol Vis Sci., 41: 3451-3459 (2000).
Mittal et al., "β2-Adrenoreceptor is a Regulator of the α-Synuclein Gene Driving Risk of Parkinson's Disease," Science, 357(6354): 891-898 (2017).
Mizutani et al., "Nucleoside Reverse Transcriptase Inhibitors Suppress Laser-Induced Choroidal Neovascularization in Mice," Invest Ophthalmol Vis Sci, 12: 7122-7129 (2015).
Mochizuki et al., "An AAV-derived Apaf-1 dominant negative inhibitor prevents MPTP toxicity as antiapoptotic gene therapy for Parkinson's disease," PNAS, 98(19): 10918-10923 (2001).
Nakahira et al., "Autophagy Proteins Regulate Innate Immune Responses by Inhibiting the Release of Mitochondrial DNA Mediated by the NALP3 Inflammasome," Nat Immunol, 12: 222-230 (2011).
Nakao et al., "Infiltration of COX-2-expressing macrophages is a prerequisite for IL-1?-induced neovascularization and tumor growth," J Clin Invest, 115(11): 2979-2991 (2005).
Noh et al., "Cordycepin inhibits IL-1β-induced MMP-1 and MMP-3 expression in rheumatoid arthritis synovial fibroblasts," Rheumatology, 48: 45-48 (2009).
Nykanen et al., "ATP Requirements and Small Interfering RNA Structure in the RNA Interference Pathway," Cell, 107: 309-321 (2001).
O'Brien et al., "A bioluminescent caspase-1 activity assay rapidly monitors inflammasome activation in cells," Journal of Immunological Methods, 447:1-13 (2017).
Okamoto et al., "Constitutively Active Inflammasome in Human Melanoma Cells Mediating Autoinflammation via Caspase-1 Processing and Secretion of Interleukin-1ß," The Journal of Biological Chemistry, 285(9): 6477-6488 (2010).
Ostertag et al., "Induction of Endogenous Virus and of Thymidine Kinase by Bromodeoxyuridine in Cell Cultures Transformed by Friend Virus," Proc Natl Acad Sci USA, 71:4980-4985 (1974).

(56) References Cited

OTHER PUBLICATIONS

Ou et al., "NLRP3 Inflammasome Inhibition Prevents α-Synuclein Pathology by Relieving Autophagy Dysfunction in Chronic MPTP-Treated NLRP3 Knockout Mice," Molecular Neurobiology, 58: 1303-1311 (2020).
Ozaki et al., "Targeting the NLRP3 inflammasome in chronic inflammatory diseases: current perspectives," Journal of Inflammation Research, 8: 15-27 (2015).
Pamuk et al., "Spleen Tyrosine Kinase Inhibition in the Treatment of Autoimmune, Allergic and Autoinflammatory Diseases," Arthritis Research and Therapy, 12:222, 1-11 (2010).
Pelegrin et al., "Pannexin-1 Mediates Large Pore Formation and Interleukin-1 beta Release by the ATP-gated P2X7 Receptor," EMBO J, 25: 5071-5082 (2006).
Peng et al., "Systemic Administration of an Antagonist of the ATP-Sensitive Receptor P2X7 Improves Recovery After Spinal Cord Injury," PNAS, 106(30): 12489-12493 (2009).
Pereira et al., "Activation of NLRC4 by Flagellated Bacteria Triggers Caspase-1-Dependent and -Independent Responses to Restrict Legionella Pneumophila Replication in Macrophages and in Vivo," The Journal of Immunology, 187: 6447-6455 (2011).
Petrilli et al., "Activation of the NALP3 Inflammasome is Triggered by Low Intracellular Potassium Concentration," Cell Death Differ, 14: 1583-1589 (2007).
Pubchem.Schembl 15257684. Feb. 13, 2015; pp. 1-10.
Puchem. CID 59120361. Aug. 20, 2012; pp. 1-10.
Qin et al., "Propionibacterium Acnes Induces 1L-1b Secretion via the NLRP3 Inflammasome in Human Monocytes," Journal of Investigative Dermatology, 134: 381-388 (2014).
Qu et al., "Pannexin-1 is Required for ATP Release During Apoptosis but not for Inflammasome Activation," J Immunol, 186:6553-6561 (2011).
Raffaghello et al., "The P2X7 Receptor Sustains the Growth of Human Neuroblastoma Cells Through a Substance P-Dependent Mechanism," Cancer Res, 66(2): 907-914 (2006).
Rathinam et al., "TRIF Licenses Caspase-11-Dependent NLRP3 Inflammasome Activation by Gram-Negative Bacteria," Cell, 150: 606-619 (2012).
Rautio et al., "Piperazinylalkyl prodrugs of naproxen improve in vitro skin permeation," European journal of pharmaceutical sciences, 11(2):157-163 (2000).
Rawat et al., "Inflammasome Up-Regulation and Activation in Dysferlin-Deficient Skeletal Muscle," The American Journal of Pathology, 176(6): 2891-2900 (2010).
Ribeiro et al., "Activation of innate immune defense mechanisms contributes to polyomavirus BK-associated nephropathy," Kidney International, 81: 100-111 (2012).
Rimessi et al., "Mitochondrial Ca2+ dependent NLRP3 activation exacerbates the Pseudomonas aeruginosa-driven inflammatory response in cystic fibrosis," Nature Communications, 6(Article No. 6201): 1-16 (2015).
Riteau et al., "ATP Release and Purinergic Signaling: A Common Pathway for Particle-Mediated Inflammasome Activation," Cell Death Dis, 3: e403 (2012).
Ritter et al., "Schistosoma Mansoni Triggers Dectin-2, which Activates the Nlrp3 Inflammasome the Alters Adaptive Immune Responses," PNAS, 107(47): 20459-20464 (2010).
Rosales-Reyes et al., "Burkholderia Cenocepacia Type VI Secretion System Mediates Escape of Type II Secreted Proteins into the Cytoplasm of Infected Macrophages," PloS One, 7(7): e41726, 1-14 (2012).
Ryu et al., "Block of Purinergic P2X7 Receptor is Neuroprotective in an Animal Model of Alzheimer's Disease," Neuropharmacology and Neurotoxicology, 19(17): 1715-1719 (2008).
Saladino et al., "Ozonation of thionucleosides. A new chemical transformation of 4-thiouracil and 6-thioguanine nucleosides to cytosine and adenosine counterparts," Tetrahedron, 51(12): 3607-3616 (1995).

Samad et al., "Interleukin-1?-mediated induction of Cox-2 in the CNS contributes to inflammatory pain hypersensitivity," Nature, 410: 471-475 (2001).
Sandanger et al., "The NLRP3 inflammasome is up-regulated in cardiac fibroblasts and mediates myocardial ischaemia-reperfusion injury," Cardiovascular Research, 99: 164-174 (2013).
Sasaki et al., "Immunohistochemical Study of Fas, Fas Ligand and Interleukin-1b Converting Enzyme Expression in Human Prostatic Cancer," British Journal of Urology, 81: 852-855 (1998).
Schroder et al., "The Inflammasomes," Cell, 140: 821-832 (2010).
Serrano et al., "Evidence of association of the NLRP1 gene with giant cell arteritis," Ann Rheum Dis, 72(4): 628-630 (2013).
Sharp et al., "P2X7 Deficiency Suppresses Development of Experimental Autoimmune Encephalomyelitis," Journal of Neuroinflammation, 5(33): 1-13 (2008).
Shin et al., "Self Double-Stranded (ds) DNA induced 1L-1b Production From Human Monocytes by Activating NLRP3 Inflammasome in the Presence of Anti-dsDNA Antibodies," J Immunol, 190: 1407-1415 (2013).
Shio et al., "Malarial Hemozoin Activates the NLRP3 Inflammasome Through Lyn and Syk Kinases," PLOS Pathogens, 5(8): E1000559, 1-14 (2009).
Singhal et al., "Inflammasomes in neuroinflammation and changes in brain function: a focused review," Frontier Neurosci, 8(Article 315): 1-13 (2014).
Sivaraj et al., "Ocular manifestations of systemic lupus erythematosus," Rheumatology, 46: 1757-1762 (2007).
Soderlund et al., "Elevation of cerebrospinal fluid interleukin-1? in bipolar disorder," J Psychiatry Neurosci, 36(2): 114-118 (2011).
Sokal et al., "A dose ranging study of the pharmacokinetics, safety, and preliminary efficacy of lamivudine in children and adolescents with chronic hepatitis B," Antimicrobial agents and chemotherapy, 44(3):590-597 (2000).
Solini et al., "Increased P2X7 Receptor Expression and Function in Thyroid Papillary Cancer: A New Potential Marker of the Disease?," Endocrinology, 149(1): 389-396 (2007).
Song et al., "NLRP3 Phosphorylation Is an Essential Priming Event for Inflammasome Activation," Molecular Cell, 68: 185-197 (2017).
Sorge et al., "Genetically Determined P2X7 Receptor Pore Formation Regulates Variability in Chronic Pain Sensitivity," Nat Med, 18: 595-599 (2012).
Stienstra et al., "Inflammasome is a Central Player in the Induction of Obesity and Insulin Resistance," PNAS, 108(37): 15324-15329 (2011).
Stylianou et al., "Raised Serum Levels of Interleukin-18 is Associated with Disease Progression and May Contribute to Virological Treatment Failure in HIV-1-Infected Patients," Clin Exp Immunol, 132: 462-466 (2003).
Surprenant et al., "The Cytolytic P2Z Receptor for Extracellular ATP Identified as a P2X Receptor (P2X7)," Science, 272: 735-738 (1996).
Sutterwala et al., "NALP3: a Key Player in Caspase-1 Activation," Journal of Endotoxin Research, 12(4): 1-6 (2006).
Syberg et al., "Genetic Background Strongly Influences the Bone Phenotype of P2X7 Receptor Knockout Mice," Journal of Osteoporosis, Article ID 391097 (2012).
Tarallo et al., "DICEr1 Loss and Alu RNA Induce Age-Related Macular Degeneration via the NLRP3 Inflammasome and MyD88," Cell, 149: 847-859 (2012).
Taylor et el., "P2X7 Deficiency Attenuates Renal Injury in Experimental Glomerulonephritis," J Am Soc Nephrol, 20: 1275-1281 (2009).
Thakur et al., "Caspase-1 Inhibitor Reduces Severity of Pseudomonas Aeruginosa Keratitis in Mice," Invest Ophthalmol Vis Sci, 45: 3177-3184 (2004).
Thakur et al., "Regulation of Pseudomonas Aeruginosa Corneal Infection in IL-1b Converting Enzyme (ICE, caspase-1) Deficient Mice," Current Eye Research, 29(4-5): 225-233 (2004).
Toma et al., "Pathogenic Vibrio Activate NLRP3 Inflammasome via Cytotoxins and TLR/Nucleotide-Binding Oligomerization Domain-Mediated NF-kB Signaling," The Journal of Immunology, 184: 5287-5297 (2010).

(56) References Cited

OTHER PUBLICATIONS

Tomura et al., "Effects of therapeutic hypothermia on inflammasome signaling after traumatic brain injury," Journal of Cerebral Blood Flow & Metabolism, 32: 1939-1947 (2012).
Tsai et al., "Epigallocatechin-3 Gallate Prevents Lupus Nephritis Development in Mice via Enhancing the Nrf2 Antioxidant Pathway and Inhibiting NLRP3 Inflammasome Activation," Free Radical Biology and Medicine, 51: 744-754 (2011).
Ture-Ozdemir et al., "Pro-inflammatory cytokine and caspase-1 responses to pattern recognition receptor activation of neutrophils and dendritic cells in Behcet's disease," Rheumatology, 52:800-805 (2013).
Usui et al., "Critical Role of Caspase-1 in Vascular Inflammation and Development of Atherosclerosis in Western Diet-fed Apolipoprotein E-deficient Mice," Biochemical and Biophysical Research Communications, 425:162-168 (2012).
Van Praag et al., "Stable Concentrations of Zidovudine, Stavudine, Lamivudine, Abacavir, and Nevirapine in Serum and Cerebrospinal Fluid during 2 Years of Therapy," Antimicrobial Agents and Chemotherapy, 46(3): 896-899 (2002).
Vanaja et al., "Bacterial RNA:DNA hybrids are activators of the NLRP3 inflammasome," PNAS, 111(21): 7765-7770 (2014).
Vandanmagsar et al., "The NALP3/NLRP3 Inflammasome Instigates Obesity-Induced Autoinflammation and Insulin Resistance," Nat Med, 17(2): 179-188 (2011).
Vergani et al., "Effects of the Purinergic Inhibitor Oxidized ATP in a model of Islet Allograft Rejection," Diabetes, 62: 1665-1675 (2013).
Vergani et al., "Long-Term Heart Transplant Survival by Targeting the Ionotropic Purinergic Receptor P2X7," Circulation, 127: 463-475 (2013).
Vilaysane et al., "The NLRP3 Inflammasome Promotes Renal Inflammation and Contributes to CKD," J Am Soc Nephrol, 21: 1732-1744 (2010).
Wang et al., "Metabolic inflammation exacerbates dopaminergic neuronal degeneration in response to acute MPTP challenge in type 2 diabetes mice," Experimental Neurology, 251: 22-29 (2014).
Wang et al., "P2X7 Receptor Inhibition Improves Recovery After Spinal Cord Injury," Nature Medicine, 10(8): 821-827 (2004).
Wang et al., "Quercetin and Allopurinol Reduce Liver Thioredoxin interacting Protein to Alleviate Inflammation and Lipid Accumulation in Diabetic Rats," British Journal of Pharmacology, 169: 1352-1371 (2013).
Weber et al., "Lack of the Purinergic Receptor P2X7 Results in Resistance to Contact Hypersensitivity," J Exp Med, 27(12): 2609-2619 (2010).
Wegrzyn et al., "Rheumatoid arthritis after 9 years of human immunodeficiency virus infection: possible contribution of tritherapy," The Journal of Rheumatology, 29: 2232-2234 (2002).
Wilhelm et al., "Graft-versus-host Disease is Enhanced by Extracellular ATP Activating P2X7R," Nat Med, 16: 1434-1438 (2010).
Wong et al., "The 3 Year Incidence and Cumulative Prevalence of Retinopathy: The Atherosclerosis Risk In Communities Study," Am J Ophthalmol, 143(6): 970-976 (2007).
Woods et al., "P2x7 Receptor Activation Induces Inflammatory Responses in Salivary Gland Epithelium," Am J Physiol Cell Physiol, 303: S790-S801 (2012).
Wree et al., "NLRP3 inflammasome activation is required for fibrosis development in NAFLD," J Mol Med (Berl)., 92(10): 1069-1082 (2014).
Wu et al., "Functional Decreases in P2X7 Receptors are Associated with Retinoic Acid-Induced Neuronal Differentiation of Neuro-2a Neuroblastoma Cells," Cellular Signaling, 21: 881-891 (2009).
Xia et al., "Neurons Respond Directly to Mechanical Deformation With Pannexin-Mediated ATP Release and Autostimulation of P2X7 Receptors," J Physiol, 590(10): 2285-2304 (2012).
Xu et al., "Innate immune sensing of bacterial modifications of; Rho GTPases by the Pyrin inflammasome," Nature, 513: 237-241 (2014).
Xu et al., "Mycoplasma Hyorhinis Activates the NLRP3 Inflammasome and Promotes Migration and Invasion of Gastric Cancer Cells," PLOS One, 8(11): 1-14 (2013).
Yajima et al., "Critical Role of Bone Marrow Apoptosis-Associated Speck Like Protein, an Inflammasome Adaptor Molecule, in Neointimal Formation After Vascular Injury in Mice," Circulation, 117: 3079-3087 (2008).
Yamin et al., "Activation of the Native 45-kDa Precursors Form of Interleukin-1-Converting Enzyme," J Biol Chem, 271: 13272-13282 (1996).
Yarchoan et al., "Response of Humanimmunodeficiency-Virus-Associated Neurological Disease to 3'-Azido-3'-Deoxythymidine," Lancet, 132-135 (1987).
Yasukawa et al., "An ITAM-Syk-CARD9 signalling axis triggers contact hypersensitivity by stimulating IL-1 production in dendritic cells," Nature Communications, 5:3755 (2014).
Youm et al., "Elimination of the NLRP3-ASC Inflammasome Protects Against Chronic Obesity-Induced Pancreatic Damage," Endocrinology, 152(11): 4039-4045 (2011).
Zaborina et al., "P2Z-Independent and P2Z Receptor-Mediated Macrophage Killing by Pseudomonas Aeruginosa Isolated from Cystic Fibrosis Patients," Infection and Immunity, 67(10): 5231-5242 (1999).
Zaborina et al., "Secreted Products of a Nonmucoid Pseudomonas Aeruginosa Strain Induce Two Modes of Macrophage Killing: External—ATP- dependent, P2Z-Receptor-Mediated Necrosis and ATP-Independent, Caspase-Mediated Apoptosis, Microbiology," 146: 2521-2530 (2000).
Zhang et al., "Cardiac Fibroblasts Contribute to Myocardial Dysfunction in Mice with Sepsis: The Role of NLRP3 Inflammasome Activation," PLoS One, 9(9): e107639 (2014).
Zhang et al., "Effects of Thalidomide on Angiogenesis and Tumor Growth and Metastasis of Human Hepatocellular Carcinoma in Nude Mice," World J Gastroenterol, 11(2): 216-220 (2005).
Zhang et al., "Enterohemorrhagic *Escherichia coli* Specific Enterohemolysin Induced IL-1b in Human Macrophages and EHEC-Induced IL-1b required Activation of NLRP3 Inflammasome," PLOS One, 7(11): 1-9 (2012).
Zhao et al., "Bay11-7082 attenuates murine lupus nephritis via inhibiting NLRP3 inflammasome and NF-kB activation," International Immunopharmacology, 17: 116-122 (2013).
Zhao et al., "P2X7 Blockade Attenuates Murine Lupus Nephritis by Inhibiting Activation of the NLRP3/ASC/Caspase 1 Pathway," Arthritis and Rheumatism, 65(12): 3176-3185 (2013).
Zheng et al., "Silence of NLRP3 Suppresses Atherosclerosis and Stabilizes Plaques in Apolipoprotein E-Deficient Mice," Mediators of Inflammation, 2014(Article ID: 507208): 1-8 (2014).
Zhou et al., "MicroRNA-7 targets Nod-like receptor protein 3 inflammasome to modulate neuroinflammation in the pathogenesis of Parkinson's disease," Molecular Neurodegeneration, 11(28): 1-15 (2016).
Ziganshin et al., "Effect of PPADS on P2X Receptor-Mediated Responses of Human Blood Vessels," Bulletin of Experimental Biology and Medicine, 137(3): 284-287 (2004).
U.S. Appl. No. 14/450,000, Granted.
U.S. Appl. No. 15/142,087, Granted.
U.S. Appl. No. 16/361,810, Granted.
U.S. Appl. No. 17/189,870, Pending.
U.S. Appl. No. 15/552,441, Granted.
U.S. Appl. No. 16/361,832, Pending.
U.S. Appl. No. 17/189,803, Pending.
U.S. Appl. No. 17/189,833, Pending.
Al-Khalidi et al., "Zidovudine ameliorates pathology in the mouse model of Duchenne muscular dystrophy via P2RX7 purinoceptor antagonism," Acta Neuropathologica Communications, 6:27 (2018).
Dehner et al., "Parkinsonism in HIV infected patients during antiretroviral therapy—data from a Brazilian tertiary hospital," Braz J Infect Dis, 20(5): 499-501 (2016).
Hirsch et al., "Neuroinflammation in Parkinson's disease: a target for neuroprotection?," Lancet Neurol, 8: 382-397 (2009).

(56) References Cited

OTHER PUBLICATIONS

Koprich et al., "Neuroinflammation mediated by IL-1β increases susceptibility of dopamine neurons to degeneration in an animal model of Parkinson's disease," Journal of Neuroinflammation, 5:8 (2008).
McCoy et al., "Blocking Soluble Tumor Necrosis Factor Signaling with Dominant-Negative Tumor Necrosis Factor Inhibitor Attenuates Loss of Dopaminergic Neurons in Models of Parkinson's Disease," The Journal of Neuroscience, 26(37): 9365-9375 (2006).
Mirsattari et al., "Parkinsonism With HIV Infection," Movement Disorders, 13(4): 684-689 (1998).
Tansey et al., "Neuroinflammation in Parkinson's disease: Its role in neuronal death and implications for therapeutic intervention," Neurobiology of Disease, 37(3): 510-518 (2010).
Tisch et al., Parkinsonism in HIV-Infected Patients on Highly Active Antiretroviral Therapy, Neurology, 73(5): 401-403 (2009).
Wahner et al., "Inflammatory Cytokine Gene Polymorphisms and Increased Risk of Parkinson Disease," Arch Neurol., 64: 836-840 (2007).
Besnard et al., "NLRP3 Inflammasome is required in murine asthma in the absence of aluminium adjuvant," allergy, 86:1047-1057 (2011).
Chakraborty et al., "Inflammasome Signaling at the Heart of Central Nervous System Pathology," Journal of Neuroscience, 88(8): 1615-1631 (2010).
Fowler et al., "Nucleoside Reverse Transcriptase Inhibitors are Anti-Inflammatory and Target Dry Age-Related Macular Degeneration," University of Kentucky Uknowledge; Theses and Dissertations—Physiology; pp. 1-115 (2014).
Goldback-Mansky et al., "Current status of understanding the pathogenesis and management of patients with NOMID/CINCA," Curr Rheumatol Rep, 13(2):123-131 (2011).
Goosens et al., "Expression of NLRP3 inflammasome and T cell population markers in adipose tissue are associated with insulin resistance and impaired glucose metabolism in humans," Molecular Immunology, 50:142-149 (2012).
Hattori et al., "Feasibility study of B16 melanoma therapy using oxidized ATP to target purinergic receptor P2X7," European Journal of Pharmacology, 695:20-26 (2012).
Hentze et al., "Critical Role for Cathepsin B in Mediating Caspase-1-Dependent Interleukin-18 Maturation and Caspase-1-Independent Necrosis Triggered by the Microbial Toxin Nigericin," Cell Death Differ, 10: 956-968 (2003).
Iannello et al., "HIV-1 Causes an Imbalance in the Production of Interleukin-18 and Its Natural Antagonist in HIV-Infected Individuals: Implications for Enhanced Viral Replication," J Infect Dis, 201:608-617 (2010).
Kerur et al., "TLR-Independent and P2X7-Dependent Signaling Mediate Alu RNA-Induced NLRP3 Inflammasome Activation in Geographic Atrophy," Invest Ophthalmol Vis Sci, 54: 7395-7401 (2013).
Pubchem. CID 59120361. Aug. 20, 2012; pp. 1-10.
Singhal et al., "Inflammasomes in neuroinflammation and changes in brain function: a focused review," Frontiers in Neuroscience, 8: Article 315 (2014).
Tomura et al., "Effects of Therapeutic Hypothermia on Inflammasome signaling After Traumatic Brain Injury," Journal of Cerebral Blood Flow and Metabolism, 32: 1939-1947 (2012).
Vandanmagsar et al., "The NAPL3/NLRP3 Inflammasome Instigates Obesity-Induced Autoinflammation and Insulin Resistance," Nat Med, 17(2): 179-188 (2011).

\* cited by examiner pUC19 | pAluA pUC19 + d4T | pAluA + d4T

COMPOSITIONS AND METHODS FOR TREATING RETINAL DEGRADATION

RELATED APPLICATIONS

This application is a continuation of U.S. Pat. Nos. 10,864,212, 10,300,057, and 9,326,983, U.S. Provisional Application Ser. No. 61/861,290, filed Aug. 1, 2013, and U.S. Provisional Application Ser. No. 61/987,612, filed May 2, 2014, the entire disclosures of which are incorporated herein by this reference.

TECHNICAL FIELD

The presently-disclosed subject matter relates to compositions for treating retinal damage and/or degradation. More specifically, this disclosure relates to methods for treating degradation of the retinal pigment epithelium by administering compositions comprising a nucleoside and/or a nucleoside reverse transcriptase inhibitor (NRTI).

BACKGROUND

Geographic atrophy, an advanced form of age-related macular degeneration that causes blindness in millions of people worldwide and for which there is no approved treatment, results from death of retinal pigmented epithelium (RPE) cells. For example, expression of DICER, an enzyme involved in microRNA (miRNA) biogenesis, is reduced in the RPE of human eyes with geographic atrophy, and that conditional ablation of Dicer1 induces RPE degeneration in mice. Surprisingly, ablation of seven other enzymes responsible for miRNA biogenesis or function does not induce such pathology. Instead, knockdown of DICER1 leads to accumulation of Alu repeat RNA in human RPE cells and of B1 and B2 (Alu-like elements) repeat RNAs in the RPE of mice. Alu RNA is dramatically increased in the RPE of human eyes with geographic atrophy, and introduction of this pathological RNA induces death of human RPE cells and RPE degeneration in mice.

Age-related macular degeneration (AMD), which is as prevalent as cancer in industrialized countries, is a leading cause of blindness worldwide. In contrast to the neovascular form of AMD, for which many approved treatments exist, the far more common atrophic form of AMD remains poorly understood and without effective clinical intervention. Extensive atrophy of the retinal pigment epithelium leads to severe vision loss and is termed geographic atrophy.

Hence, there remains a need for compositions and methods for treating retinal degradation, and particularly RPE degradation.

BRIEF SUMMARY

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

The present disclosure provides, in certain embodiments, a method for treating retinal damage and/or degradation, comprising administering an effective amount of a composition to a subject in need thereof, wherein the composition comprises a reverse transcriptase inhibitor, such as a nucleoside reverse transcriptase inhibitor (NRTI), selected from: (i) a compound having the structure of

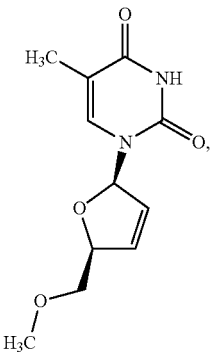 [SMILES: COC[C@@H]1C=C[C@H](n2cc(C)c(=O)[nH]c2=O)O1]

or a pharmaceutically acceptable salt thereof;
(ii) a compound having the structure of

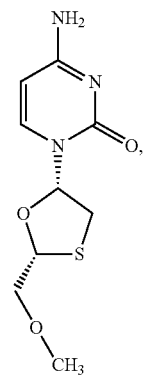 [SMILES: COC[C@@H]1O[C@H](n2ccc(N)nc2=O)CS1]

or a pharmaceutically acceptable salt thereof; (iii) stavudine (d4T); (iv) lamivudine (3TC); (v) cordycepin; (vi) azidothymidine (AZT); (vii) abacavir (ABC); and/or (viii) a combination thereof.

Moreover, the methods of the present disclosure may further comprise the steps of (i) inhibiting inflammasome activation by Alu RNA; (ii) reducing ATP-induced permeability of a cell; (iii) reducing an amount of mitochondrial reactive oxygen species in a cell; aid/or (iv) inhibiting activation of at least one inflammasome in a subject's eye. Additionally, the cell(s) of the methods of the present disclosure may be chosen, for example, from a retinal pigmented epithelium cell, a retinal photoreceptor cell, a choroidal cell, and a combination thereof. And an inflammasome of the present disclosure may be, for example, an NLRP3 inflammasome, an IL-1beta inflammasome, or a combination thereof.

Furthermore, in some embodiments, the present disclosure provides a compound having the structure:

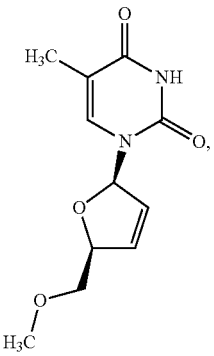

or a pharmaceutically acceptable salt thereof;
or a compound having the structure

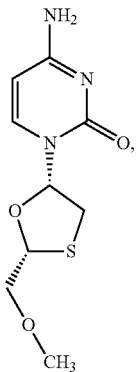

or a pharmaceutically acceptable sale thereof.

The present disclosure also provides a pharmaceutical composition comprising at least one of the compounds provided in the present disclosure, together with a pharmaceutically acceptable carrier. And further embodiments of the present disclosure include a method for synthesizing at least one compound provided in the present disclosure.

BRIEF DESCRIPTION OF THE DRAWINGS

FIG. 11 was created after human THP-1 monocytes were differentiated into macrophages with PMA, and, as shown in FIG. 11, treatment with MSU, a known inflammasome activator, increased IL-1 beta secretion compared to non-treated cells, whereas d4T co-administration at a range of doses (25-1000 uM) did not significantly affect IL-1beta secretion.

FIG. 17 provides the results of the fluorescence measurement in relative fluorescence units (RFU, y-axis).

FIG. 38 shows a gel indicating that d4T blocked Caspase-1.

In FIG. 54, mitochondrial reactive oxygen species (ROS) were visualized with MitoSox (Red) and cell nuclei with Hoechst (Blue).

DESCRIPTION OF EXEMPLARY EMBODIMENTS

Figure 1:
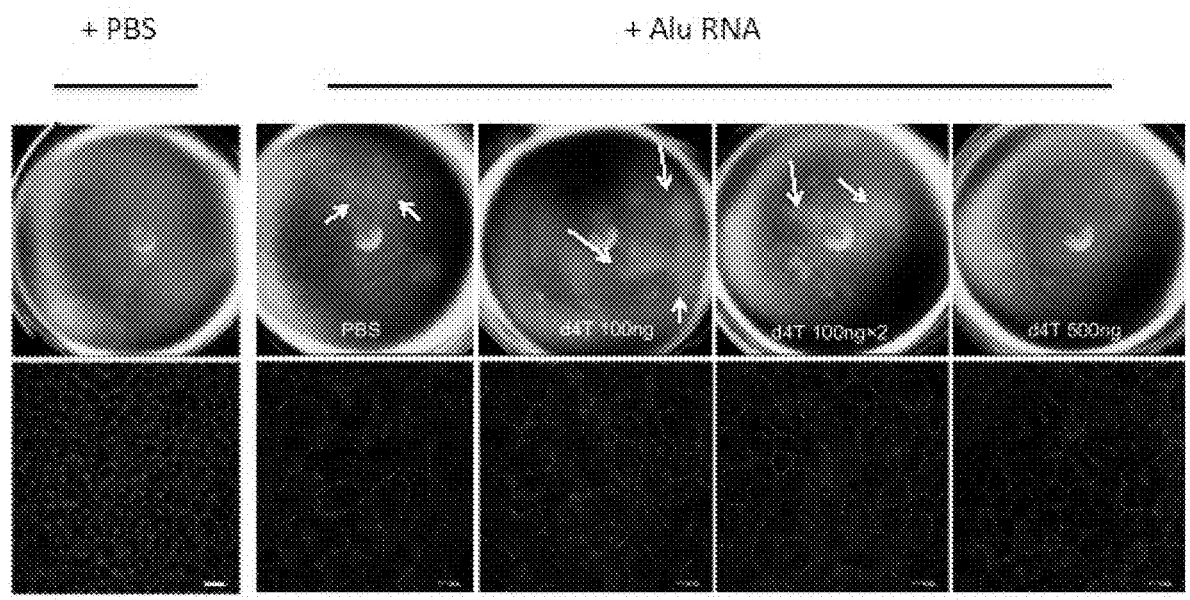
FIG. 1 displays a top row of ocular fundus photographs of mice receiving control PBS, or Alu RNA treatment, with or without increasing amounts of d4T (left to right); and RPE flat mounts, stained for intercellular junctions (ZO-1) in red that are disrupted upon Alu RNA administration but that are restored to healthy RPE morphology/intercellular junctions at highest dose of d4T.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is illustrated by specific but non-limiting examples throughout this description. The examples may include compilations of data that are representative of data gathered at various times during the course of development and experimentation related to the present invention(s). Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

While the following terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a fluorophore" includes a plurality of such images, and so forth.

Unless otherwise indicated, all numbers expressing quantities, properties, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "physiologically functional derivative" means any pharmaceutically acceptable derivative of a compound of the present disclosure. For example, an amide or ester of a compound of formula (I) or of a compound of formula (II), which upon administration to a subject, particularly a mammal, is capable of providing, either directly or indirectly, a compound of the present disclosure of an active metabolite thereof.

The terms "treatment" or "treating" refer to the medical management of a subject with the intent to cure, ameliorate, stabilize, or prevent a condition or disorder (e.g., retinal degradation). This term includes active treatment, that is, treatment directed specifically toward the improvement of a condition, and also includes causal treatment, that is, treatment directed toward removal of the cause of the associated condition. In addition, this term includes palliative treatment, that is, treatment designed for the relief of symptoms rather than the curing of the condition; preventative treatment, that is, treatment directed to minimizing or partially or completely inhibiting the development of symptoms or disorders of the associated condition; and supportive treatment, that is, treatment employed to supplement another specific therapy directed toward the improvement of the associated disease, pathological condition, or disorder.

With regard to administering the compound, the term "administering" refers to any method of providing a composition and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, intravitreous administration, including via intravitreous sustained drug delivery device, intracameral (into anterior chamber) administration, suprachoroidal injection, subretinal administration, Subconjunctival injection, sub-Tenon's administration, peribulbar administration, Transscleral drug delivery, administration via topical eye drops, and the like. Administration can be continuous or intermittent. In various aspects, a preparation can be administered therapeutically; that is, administered to treat an existing disease or condition (e.g., exposure to OP compounds). In further various aspects, a preparation can be administered prophylactically; that is, administered for prevention of a disease or condition.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The terms "subject" or "subject in need thereof" refer to a target of administration, which optionally displays symptoms related to a particular disease, condition, disorder, or the like. The subject(s) of the herein disclosed methods can be human or non-human (e.g., primate, horse, pig, rabbit, dog, sheep, goat, cow, cat, guinea pig, rodent, and non-mammals). The term "subject" does not denote a particular age or sex. Thus, adult and newborn subjects, as well as fetuses, whether male or female, are intended to be covered. The term "subject" includes human and veterinary subjects.

As will be recognized by one of ordinary skill in the art, the terms "suppression," "suppressing," "suppressor," "inhibition," "inhibiting" or "inhibitor" do not refer to a complete elimination of angiogenesis in all cases. Rather, the skilled artisan will understand that the term "suppressing" or "inhibiting" refers to a reduction or decrease in angiogenesis. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some exemplary embodiments, the presently-disclosed subject matter includes methods for treating retinal damage and/or retinal degeneration. Indeed, some methods of the present disclosure comprise administering to a subject in need thereof an effective amount of a composition for treating retinal damage and/or degradation.

In some embodiments the composition comprises a nucleoside and/or a nucleoside reverse transcriptase inhibitor (NRTI). Further, in some embodiments, the composition is a pharmaceutical composition comprising a nucleoside and/or a NRTI compound as well as a pharmaceutically acceptable carrier.

As discussed herein, in some exemplary methods of the present disclosure, the administered composition is a composition comprising a nucleoside and/or NRTI. Thus, exemplary compositions are comprised of compounds including, but not limited to, stavudine (d4T), lamivudine (3TC), cordycepin, azidothymidine (AZT), abacavir (ABC), chemical derivatives thereof methoxy-derivatives to abrogate phosphorylation), and the like, Other possible compounds include, for example, those described in U.S. Pat. No.

6,514,979 to Heredia et al. Those of ordinary skill in the art will also recognize further nucleosides and/or NRTIs, as described herein, that can be used in the compositions and methods of this disclosure.

In some embodiments a method of the present disclosure comprises inhibiting activation of one or more physiological processes by Alu RNA. As disclosed herein, Alu RNA (including Alu repeat RNA in human cells and B1 and B2, Alu-like element repeat RNAs) increases are associated with cells that are associated with certain conditions of interest. For example, an Alu RNA increase is associated with the retinal pigment epithelium (RPE) cells of eyes with geographic atrophy. This increase of Alu RNA induces the death of RPE cells. Methods and compositions disclosed herein can treat RPE degradation, thereby treating conditions associated with such cell death.

In some embodiments, a method of the present disclosure comprises inhibiting the activation of at least one inflammasome. In certain embodiments, the at least one inflammasome is selected from an NLRP3 inflammasome, a 1L-1beta inflammasome, and a combination thereof. In some embodiments, the inhibiting one or more inflammasomes of a cell includes administering an inhibitor (composition) to the cell and/or to a subject, wherein the cell is the cell of a subject. For compositions comprising an inhibitor, an inhibitor as described herein can be, for example, a polypeptide inhibitor (including an oligonucleotide inhibitor), a small molecule inhibitor, and/or an siRNA inhibitor.

Moreover, some exemplary methods of administering the present composition(s) can inhibit inflammation by LPS/ATP, inflammasome activation by LPS/ATP, inflammasome activation by Alu RNA, and/or nigericin-induced inflammasome activation. Exemplary methods can also treat retinal degradation and/or other retinal damage by reducing mitochondrial reactive oxygen species, particularly as caused by Alu RNA expression, by blocking entry via the P2X7 receptor, and/or by reducing ATP-induced cell permeability.

In some embodiments, a method of the present disclosure comprises treating retinal damage by inhibiting a particular action in a cell. In some embodiments, the cell is selected from an RPE cell, a retinal photoreceptor cell, or a choroidal cell. In some embodiments, the cell is an RPE cell. In some embodiments, the cell is the cell of a subject. In some embodiments, the cell is a cell of a subject having, suspected of having, or at risk of having a condition of interest. In some embodiments, the cell is a cell of a subject having, suspected of having, or at risk of having age-related macular degeneration. In some embodiments, the cell is a cell of a subject having, suspected of having, or at risk of having geographic atrophy. In some embodiments, the cell is a cell of a subject having, suspected of having, or at risk of having geographic atrophy and the cell is an RPE cell. In some embodiments, a subject having age-related macular degeneration can be treated using methods and compositions as disclosed herein.

Thus, as used herein with reference to a polypeptide being inhibited, "of a cell" refers to a polypeptide that is inside the cell (inside the cell membrane), on the cell (in the cell membrane, presented on the cell membrane, otherwise on the cell), or outside of a cell, but insofar as the polypeptide is outside of the cell, it is in the extracellular milieu such that one of ordinary skill in the art would recognize the polypeptide as being associated with the cell. For example, VDAC1, VDAC2, caspase-8, NFκB, or a polypeptide of an inflammasome (e.g., NLRP3, PYCARD, caspase-1) could be in the cell. For another example, NLRP3 could be in the cell or on the cell.

As described herein, the presently-disclosed subject matter further includes pharmaceutical compositions comprising the compounds described herein together with a pharmaceutically acceptable carrier.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compositions can be formulated as eye drops. For example, the pharmaceutically acceptable carrier may comprise saline solution or other substances used to formulate eye drop, optionally with other agents. Thus, eye drop formulations permit for topical administration directly to the eye of a subject.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

The presently-disclosed subject matter further includes a kit that can include a compound or pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

Moreover, NRTIs of the present disclosure are a diverse, widely used, inexpensive class of small molecules, with extensive pharmacokinetic and safety data collected over the past several decades of human use; NRTIs are therefore ripe for drug repurposing. As such, the present disclosure provides a novel and broadly applicable basis for use of one or more NRTIs by addressing major unmet medical needs.

As briefly described above, age-related macular degeneration is a disease that affects tens of millions of people worldwide, and there is no effective treatment for AMD (Ambati and Fowler, 2012). Similarly, graft-versus host disease is the major obstacle preventing successful tissue transplant (Ferrara et al., 2009); and sterile liver inflammation is a major contributor to drug-induced liver injury and steatohepatitis, a major determinant of fibrosis and carcinogenesis (Kubes and Mehal, 2012). Thus, some methods and/or compounds of the present disclosure are intended to treat age-related macular degeneration, graft-versus host disease, and/or sterile liver inflammation by administering, in some embodiments, a compound comprising at least one NRTI, as provided in the present disclosure.

Since inflammasome inhibition by NRTIs can be achieved without phosphorylation of a particular NRTI, the use of me-d4T or other phosphorylation-incompetent nucleoside analogs, as provided herein, should avoid therapeutic-limiting toxicities associated with NRTI-triphosphate-mediated polymerase inhibition (Lewis et al., 2003). Accordingly, in some embodiments, the present disclosure is directed to methods for treating retinal disease by administering me-d4T or another phosphorylation-incompetent nucleoside analog to a subject in need thereof.

Further, in certain embodiments, the present disclosure provides methods for treating retinal damage, comprising: administering an effective amount of a composition to a subject in need thereof, wherein the composition comprises an NRTI. In some embodiments, the NRTI is selected from the group consisting of stavudine (d4T), lamivudine (3TC), cordycepin, azidothymidine (AZT), abacavir (ABC), or derivatives or combinations thereof.

In some embodiments, the presently disclosed subject matter provides methods for protecting an RPE cell, a retinal photoreceptor cell, a choroidal cell, or a combination thereof, comprising at least the step of administering a composition that comprises at least one nucleoside analog or NP according to the present disclosure, to a subject in need thereof.

Moreover, in some embodiments, the present disclosure is directed to the synthesis and/or use of one or more compounds of Formula I, Formula II, Formula III, Formula IV, and/or Formula IV:

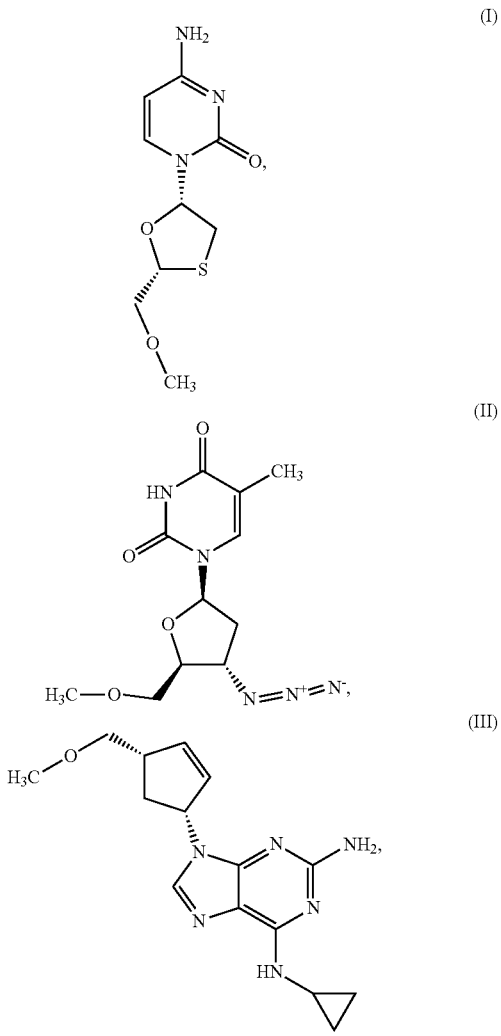

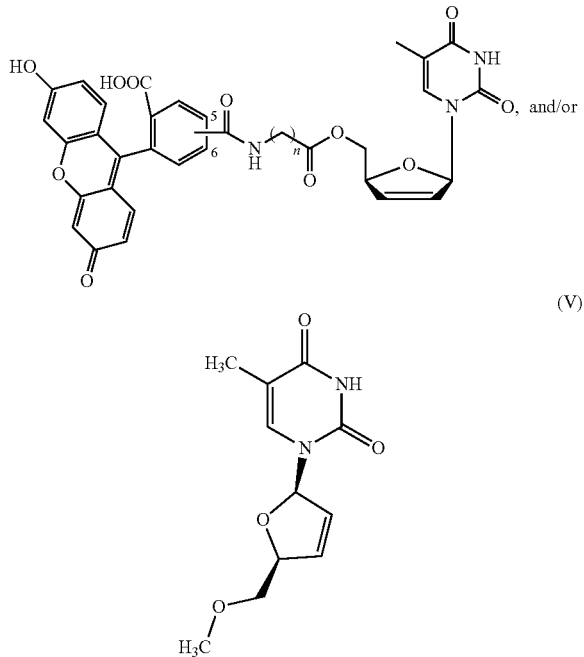

and/or to any salt, particularly any pharmaceutically acceptable salt, any solvate, and/or any physiological derivative thereof. In some embodiments, "n" of Formula IV is any integer, and in a particular embodiment, n is 11.

Further, the present disclosure provides uses of a compound of any of Formulas (I), (II), (III), (IV) and/or (IV), or any combination thereof, in the preparation or manufacture of a pharmaceutical composition, such as a drug and/or medicine, especially a composition for the treatment of retinal damage and/or retinal degeneration in a mammal. In some embodiments, the present disclosure provides a pharmaceutical composition comprising a compound of any of Formulas (I), (II), (III), (IV) and/or (IV), any salt, particularly any pharmaceutically acceptable salt, any solvate, and/or any physiological derivative thereof, together with a pharmaceutically acceptable carrier.

In certain embodiments, the methods and compositions of the present disclosure inhibit graft-versus-host disease, chronic pain, proliferative vitreoretinopathy, glaucoma, rheumatoid arthritis, multiple sclerosis, bipolar disorder, major depressive disorder, renal fibrosis, nephritis, pulmonary fibrosis, Huntington's disease, osteoporosis, chronic lymphocytic leukemia, anxiety disorders, pulmonary tuberculosis, osteoporosis in post-menopausal women and fracture patients, systemic lupus erythematosus, chronic inflammatory and neuropathic pain, autosomal dominant polycystic kidney disease, spinal cord injury, Alzheimer's disease, neuropathic pain, hypertension, varicose veins, type I diabetes, type II diabetes, gout, autoimmune hepatitis, graft vascular injury, atherosclerosis, thrombosis, metabolic syndrome, salivary gland inflammation, traumatic brain injury, ischemic heart, disease, ischemic stroke, Parkinson's disease, melanoma, neuroblastoma, prostate, breast, skin, and thyroid cancers, tubular early gastric cancer, neuroendocrine cancer, mucoid colon cancer, colon cancer; high-grade urothelial carcinoma, kidney clear cell carcinoma, undifferentiated ovary carcinoma, papillary intracystic breast carcinoma, gram negative sepsis, infectious *Pseudomonas aeruginosa*, *Vibrio cholera*, *Legionella* spp., *Francisella* spp., and *Leishmania* spp. *Chlamydia* spp., cryopyrinopathies; keratitis, acne vulgaris, Crohn's disease, ulcerative colitis, irritable bowel syndrome, insulin resistance, obesity, hemolytic-uremic syndrome, polyoma virus infection, immune complex renal disease, acute tubular injury, lupus nephritis, familial cold autoinflammatory syndrome, Muckle-Wells syndrome and neonatal onset multisystem inflammatory disease, chronic infantile neurologic cutaneous and articular autoinflammatory diseases, renal ischemia-perfusion injury, glomerulonephritis, cryoglobulinemia, systemic vasculitides, IgA nephropathy, malaria, helminth parasites, septic shock, allergic asthma, hay fever, chronic obstructive pulmonary disease, drug-induced lung inflammation, contact dermatitis, leprosy, *Burkholderia cenocepacia* infection, respiratory syncitial virus infection, psoriasis, scleroderma, reactive arthritis, cystic fibrosis, syphilis, Sjögren's syndrome, inflammatory joint disease, non-alcoholic fatty liver disease, cardiac surgery (peri-/post-operative inflammation), acute and chronic organ transplant rejection, acute and chronic bone marrow transplant rejection, tumor angiogenesis, and/or any combination thereof.

Moreover, in some embodiments, the present disclosure provides that non-canonical NRTI function, independent of chain termination, prevents P2X7-dependent blindness, graft-versus-host disease and/or sterile inflammation. Accordingly, the present disclosure is directed, in certain embodiments, to methods of preventing P2X7-dependent blindness, graft-versus-host disease and/or inflammation in a subject by administering an effective amount of at least one NRTI, as described herein, to subject in need thereof.

Further, in certain embodiments, the methods and compositions of the present disclosure inhibit (i) inflammasome activation by Alu RNA associated with a cell; (ii) inflammation by LPS/ATP, (iii) inflammasome activation by LPS/ATP, (iv) nigericin-induced inflammasome activation, and/or combinations thereof. And in some embodiments, the inflammasome is selected from the group consisting of a NLRP3 inflammasome and/or a 1L-1beta inflammasome. Additionally, some embodiments of the methods of the present disclosure may include, for example, the steps of (i) blocking entry via a P2X7 receptor associated with a cell; (ii) reducing mitochondrial reactive oxygen species caused by Alu RNA expression; and/or (iii) reducing ATP-induced cell permeability of a cell. And a cell contemplated in the present disclosure may include, for example, an RPF: cell, a retinal photoreceptor cell, a choroidal cell, or any combination thereof.

Further, NRTIs are mainstay therapeutics for HIV, and they block retrovirus replication. Alu RNA, an endogenous retroelement that also requires reverse transcriptase (RT) for its life cycle, activates the NLRP3 inflammasome to cause cell death of the retinal pigment epithelium in geographic atrophy, which is the untreatable form of age-related macular degeneration that blinds millions of individuals. Moreover, the inventors of the present disclosure have found that NRTIs, as a class, are novel inhibitors of the NLRP3 inflammasome. And, surprisingly, this effect is independent of reverse transcriptase inhibition.

Thus, the inventors of the present disclosure have found that the NRTIs d4T, AZT, ABC, and 3TC block Caspase 1 activation by Alu RNA, as does 5'-methoxy-d4T, which does not inhibit reverse transcriptase. Further, the present inventors have found that AZT is not phosphorylated in thymidine kinase-deficient cells but still blocks LPS/ATP-induced interleukin-1 beta secretion; that NRTIs block P2X7-dependent YOPRO-1 dye uptake in mouse models of geographic atrophy, graft-versus-host disease, and sterile liver inflammation; and that NRTIs are novel inhibitors of the NLRP3 inflammasome independent of canonical reverse transcriptase inhibition. Accordingly, NRTIs are ripe for drug repurposing in a variety of P2X7-driven diseases.

NRTIs were first discovered to be anti-viral compounds in 1974 (Ostertag et al., 1974), and are widely used to treat human immunodeficiency virus (HIV). The canonical mechanism of action of NRTIs is via chain termination of DNA synthesis from a viral RNA template, thereby interfering with the viral life cycle of reverse transcriptase-dependent viruses.

Age-related macular degeneration (AMD) is a leading cause of blindness in the elderly worldwide (Ambati et al., 2003; Ambati and Fowler, 2012). In the more prevalent and untreatable dry form of AMD, overabundance of non-coding Alu RNAs causes blindness by inducing cell death of the retinal pigment epithelium (Dridi et al., 2012; Kaneko et al., 2011; Tarallo et al., 2012). Alu sequences are non-coding retrotransposons that, like HIV, rely on reverse transcriptase for their life cycle (Batzer and Deininger, 2002; Dewannieux et al., 2003).

Figure 34:
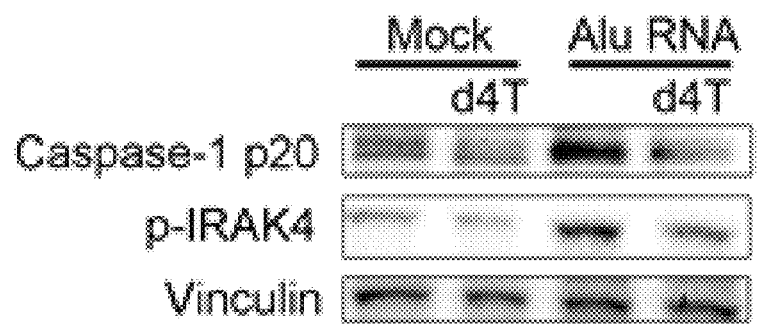
FIG. 34 is a Western blot of Caspase-1 activation (p20 subunit) and IRAK4 phosphorylation in primary human RPE cells transfected with Alu RNA±d4T.
Figure 35:
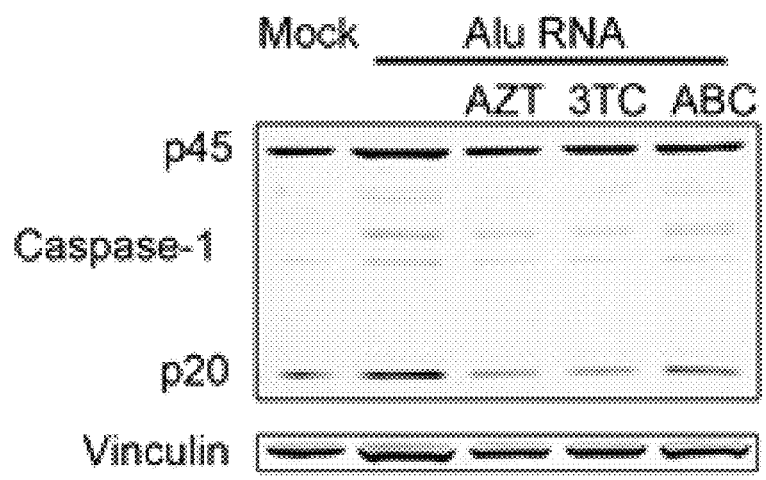
FIG. 35 is a Western blot of Caspase-1 activation in human RPE cells transfected with Alu RNA±NRTIs (3TC, AZT, ABC).
Figure 44:
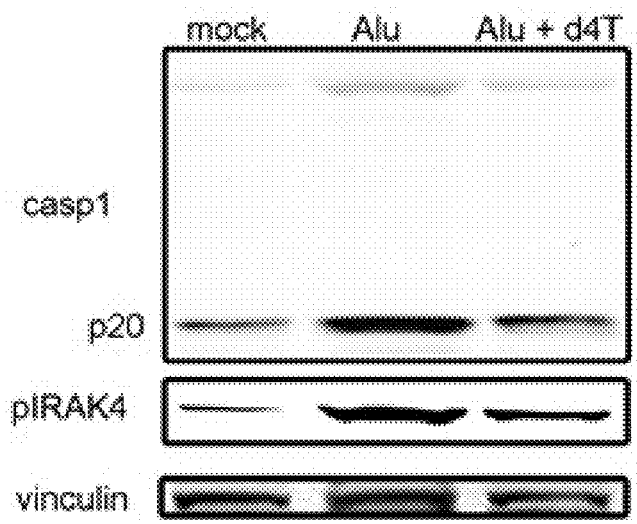
FIG. 44 is a Western blot of Caspase-1 activation (p20 subunit) and IRAK4 phosphorylation in primary mouse RPE cells transfected with Alu RNA±d4T.
Figure 45:
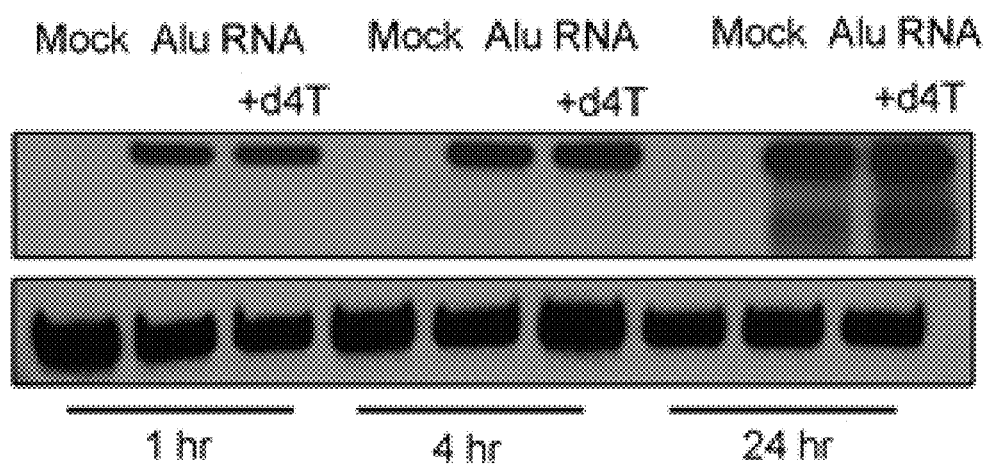
FIG. 45 is a Northern blot of biotin-UTP-labeled Alu RNA-transfected primary human RPE cells.

Alu RNA mediates RPE cell death via activation of Caspase 1 and the NLRP3 inflammasome (Tarallo et al., 2012). The present disclosure provides that a reverse transcriptase inhibitor, such as stavudine (d4T; 2'3' dideoxythymidine; Zerit, Bristol-Myers Squibb), which is FDA-approved for the treatment of HIV, prevents Caspase 1 cleavage to its active 20 kDa form (Hentze et al., 2003; Yamin et al., 1996) in primary human (FIG. 34) and mouse RPE cells (FIG. 44) without reducing Alu RNA levels (FIG. 45). Further, the present disclosure shows that d4T also blocks phosphorylation of IRAK4, a kinase downstream of the MyD88 adaptor that mediates Alu-induced RPE cell death (Tarallo et al., 2012), in human and mouse RPE cells (FIG. 34 and FIG. 44). The inventors of the present disclosure have also found that other NRTIs, including the anti-HIV drugs azidothymidine (AZT; 3'-azido-2',3'-dideoxythymidine; Retrovir, ViiV Healthcare), lamivudine (3TC; 2'3' dideoxycytidine; Zeffix, GlaxoSmithKline) and abacavir (ABC; a di-deoxyguanosine analog; Ziagen, ViiV Healthcare), also block Caspase-1 cleavage induced by Alu RNA (FIG. 35).

Figure 36:
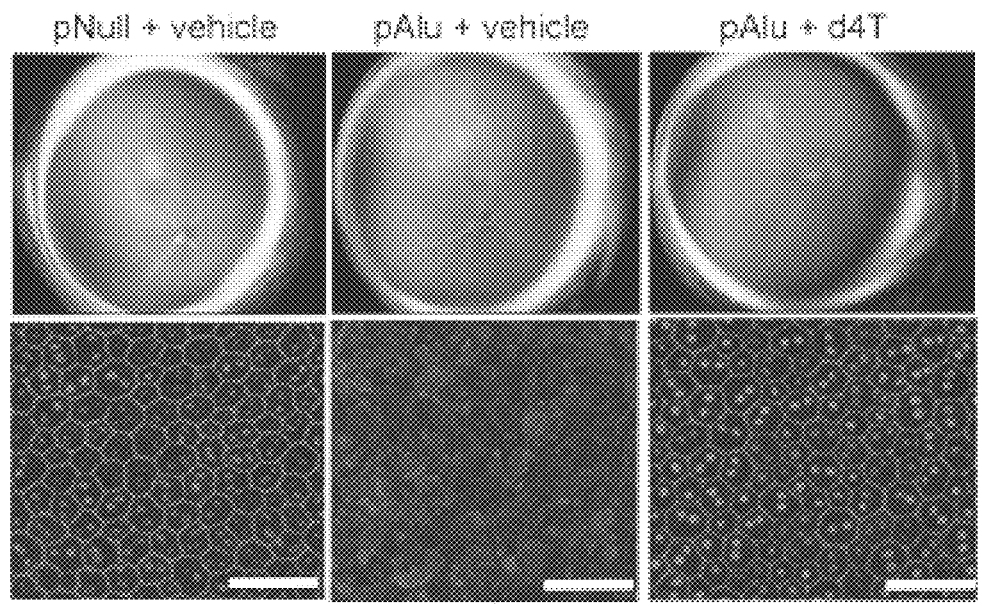
FIG. 36 includes fundus photographs: top row; flat mounts stained for zonula occludens-1 (ZO-1; red), bottom row bars, 50 μm.
Figure 37:
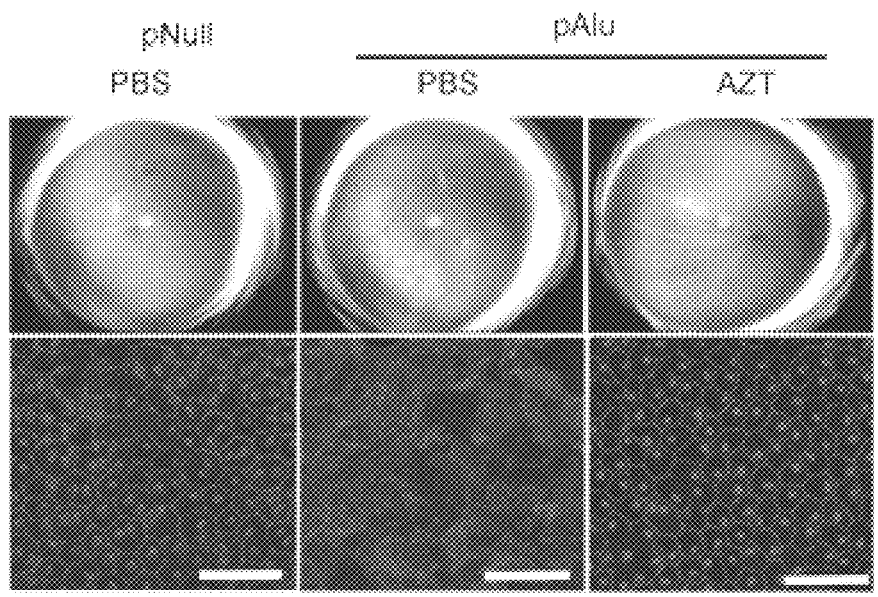
FIG. 37 provides fundus photographs: top row; flat mounts stained for zonula occludens-1 (ZO-1; red), bottom row. Scale bars, 50 μm.

Additionally, the present disclosure provides that d4T and AZT prevent RPE degeneration in the Alu RNA-induced mouse model of dry AMD. (Kaneko et al., 2011; Tarallo et al., 2012) Moreover, it has been found that mice receiving daily oral administration of d4T blocked RPE degeneration after sub-retinal injection of a plasmid expressing Alu RNA (FIG. 36), as did intraperitoneal administration of AZT (FIG. 37).

Figure 20:
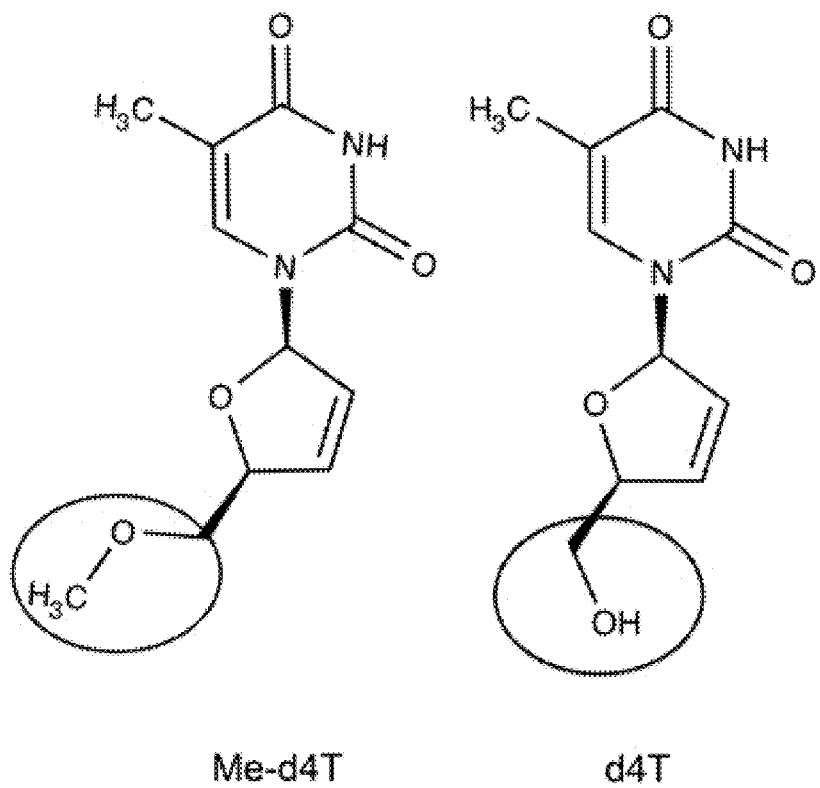
FIG. 20 provides a chemical structure of methoxy-d4T (me-d4T). More specifically, as shown in FIG. 20, a single substitution of the ribose 5' hydroxyl group of d4T with a methoxy group (circled) has been designed to prevent d4T phosphorylation

In order to test whether reverse transcriptase inhibition was required for inflammasome blockade by d4T, a 5' O-methyl-modified version of d4T (5'-OCH3-d4T; me-d4T) was synthesized (FIG. 20; FIG. 25, FIG. 36, FIG. 27, FIG. 28). Accordingly, in some embodiments, the present disclosure is directed to methods for synthesizing a 5' O-methyl-modified version of d4T as provided herein.

Figure 21:
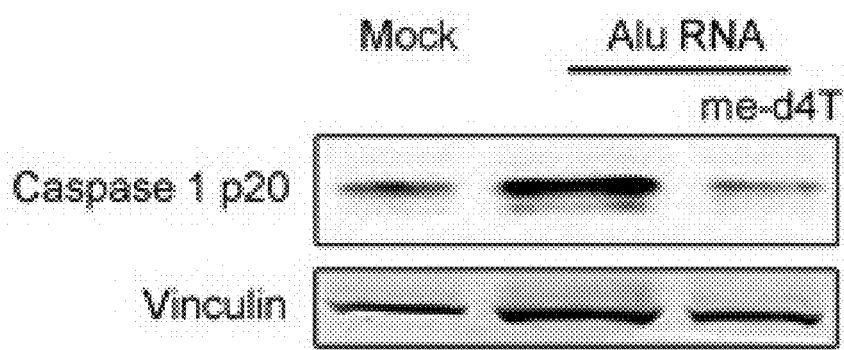
FIG. 21 is a Western blot of Caspase-1 activation (p20 subunit) in primary human RPE cells transfected with Alu RNA±me-d4T.

Only the triphosphate version of nucleoside analogs inhibit reverse transcriptase; the methyl modification at the 5' position prevents phosphorylation and thus formation of nucleoside triphosphate (Nykanen et al., 2001). Accordingly, like d4T, me-d4T also blocks Caspase-1 activation in human RPE cells (FIG. 21).

Figure 22:
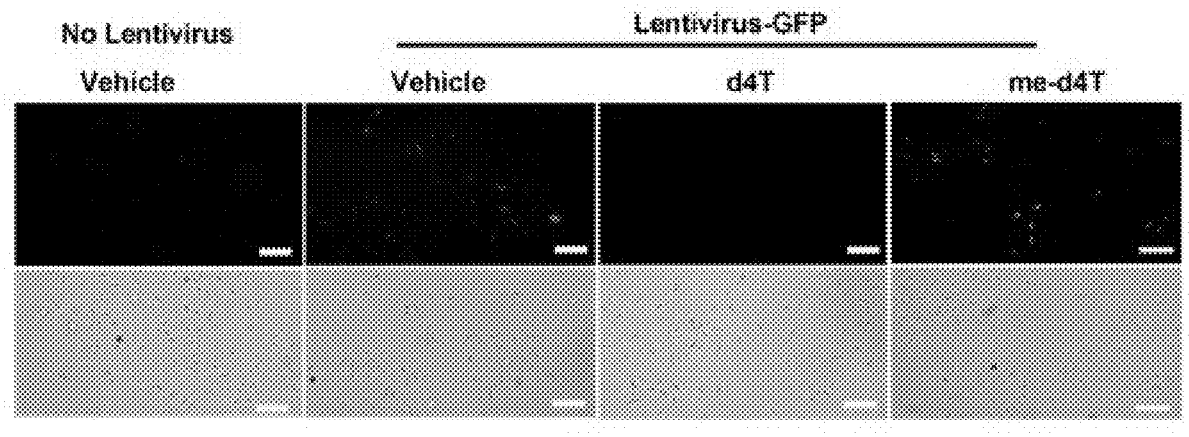
FIG. 22 shows cells, wherein unmodified d4T, but not me-d4T, blocks replication of a GFP-expressing lentivirus in HeLa cells.
Figure 23:
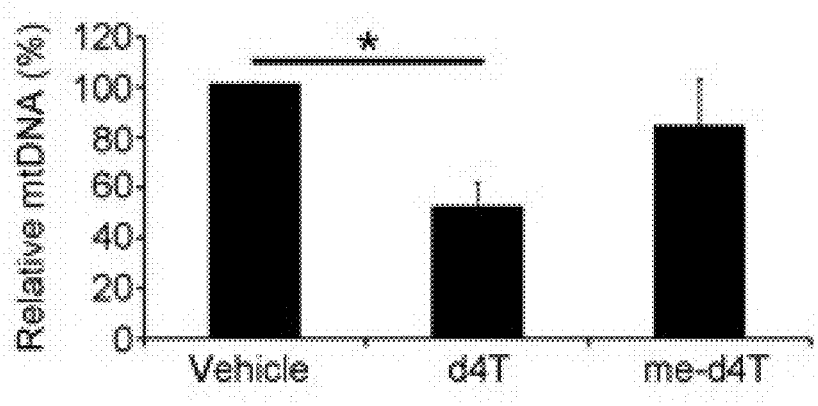
FIG. 23 provides a graph illustrating that unmodified d4T, but not me-d4T, reduces mtDNA levels (normalized to chromosomal DNA exon-intron junction sequence) in primary mouse RPE cells as determined by real-time quantitative PCR. n=4, *p<0.05 by Student's t-test.
Figure 24:
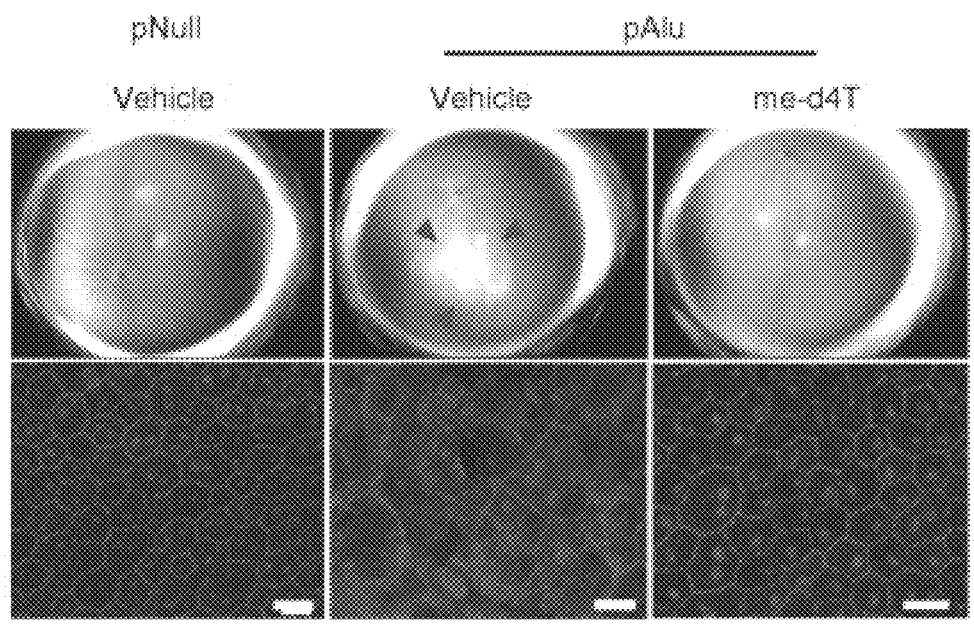
FIG. 24 provides flat mounts stained for zonula occludens-1 (ZO-1; red), bottom row. Degeneration outlined by blue arrowheads. Representative images of n=4 (B, C, E) shown. Scale bars, (C): 200 μm; (E): 20 μm FIG. 25 provides a schematic overview of me-d4T synthesis.

The present inventors have confirmed that me-d4T does not inhibit reverse transcriptase: and, in contrast to unmodified d4T, me-d4T does not block lentivirus replication (FIG. 22). Also, the triphosphate metabolite of di-deoxy nucleoside analogs caused depletion of mitochondrial DNA; and consistent with the idea that me-d4T is not phosphorylated, it has been found that d4T, but not me-d4T reduces mtDNA levels. (FIG. 23). Me-d4T also prevents Alu-induced RPE degeneration in mice (FIG. 24). These data indicate that d4T can block Caspase-1 activation and RPE degeneration independent of reverse transcriptase inhibition.

Further, the present inventors also tested whether NRTIs blocked inflammasome activation by LPS/ATP, which is not known to signal via reverse transcriptase (Mariathasan et al., 2004; Mariathasan et al., 2006; Martinon et al., 2002). It was found that d4T inhibited LP S/ATP-induced Caspase-1 maturation in primary mouse bone marrow-derived macrophages (FIG. 38) as detected by Western blot.

Figure 39:
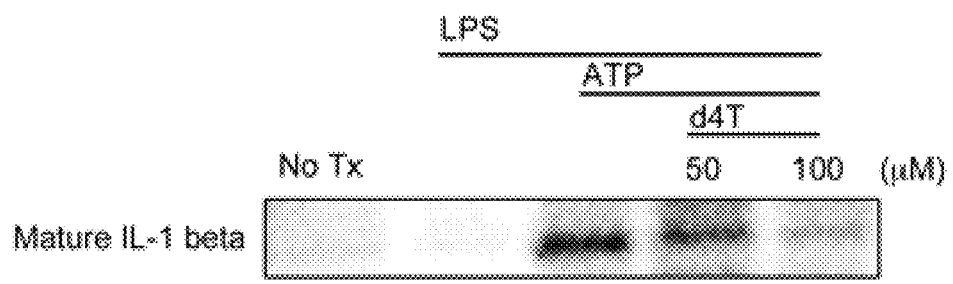
FIG. 39 also illustrates that NRTIs block LPS/ATP-induced inflammasome activation, showing specifically a gel indicating that d4T blocked IL-1 beta.

Caspase-1 directly processes interleukin 1 beta (IL-1 beta) upon LPS/ATP stimulation; d4T also blocks secretion of mature IL-1 beta in these cells (FIG. 39). To determine whether LPS/ATP-induced inflammasome activation can be inhibited without RT inhibition, the present inventors utilized thymidine kinase-deficient (Raji/TK$^-$) and -expressing (Raji/TK$^+$) cells (Balzarini et al., 1989). After addition of AZT, TK$^+$, but not TK$^-$ cells, the present inventors produced AZT-triphosphate (AZT-TP), the AZT metabolite required for RT inhibition (FIG. 40; FIG. 46, FIG. 47, FIG. 48, FIG. 49, FIG. 50). Even though AZT was not phosphorylated in TK$^-$ cells, AZT still inhibited LPS/ATP-induced interleukin-1 beta maturation (FIG. 41), indicating that AZT did not inhibit interleukin-1 beta maturation via reverse transcriptase inhibition.

Figure 42:
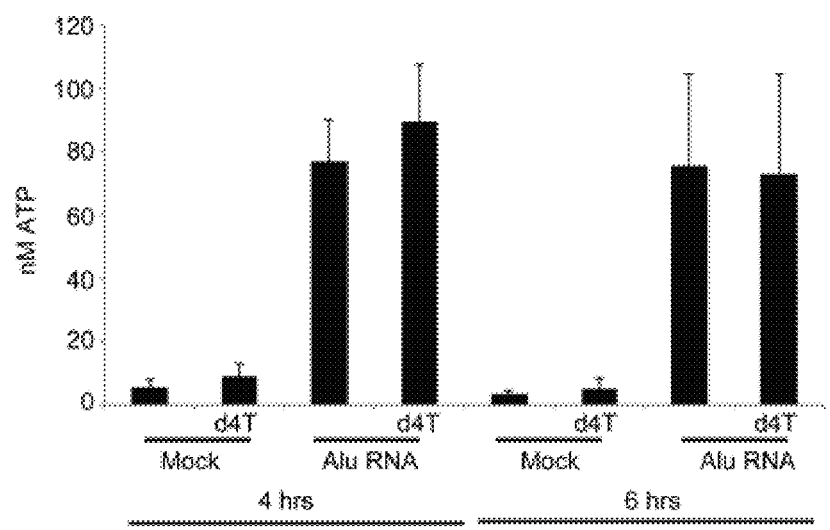
FIG. 42 is a bar graph illustrating that d4T does not block Alu-induced ATP release from primary human RPE cells (n=4).

Alu RNA (Kerur et al., 2013) and LPS/ATP (Qu et al., 2011) activate the inflammasome via the ATP receptor P2X7. The present inventors therefore hypothesized that d4T blocks P2X7 or some P2X7-dependent pathway. First, testing was conducted to determine whether d4T acts upstream of P2X7 by modulating ATP levels; however, d4T does not block release of ATP to cell culture media induced by Alu RNA (FIG. 42).

Next, testing was conducted to determine whether d4T directly antagonizes P2X7 function: upon ATP binding, cell-surface P2X7 forms non-selective cation channels that mediate inflammasome activation (Kahlenberg and Dubyak, 2004; Petrilli et al., 2007). However, d4T did not significantly modulate P2X7 cation channel function as monitored by patch clamp analysis of HEK293 stable cell lines expressing either the human or rat P2X7 receptor (Humphreys et al., 2000).

Finally, P2X7 activation is associated with the formation of a large pore that is permeable to molecules of up to ~1000 Da (Adinolfi et al., 2005; Cheewatrakoolpong et al., 2005; Surprenant et al., 1996). It was found that d4T, and also AZT and 3TC, inhibited P2X7-dependent uptake of the fluorescent dye YO-PRO1 (M. W. Da) in human P2X7-overexpressing HEK293 stable cell line (FIG. 43) after addition of the selective P2X7 agonist bzATP.

Figure 51:
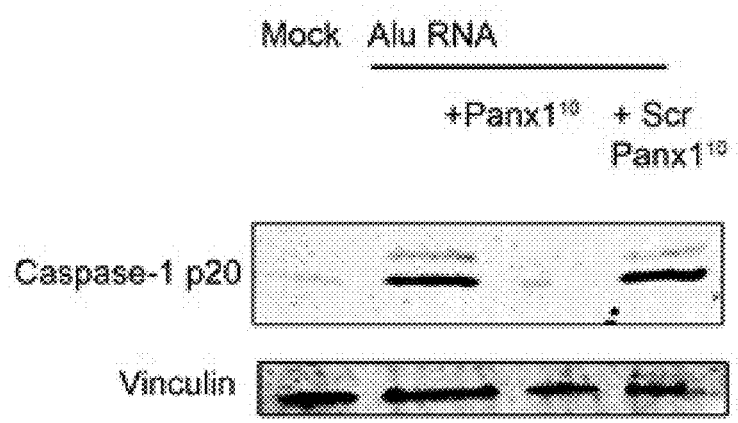
FIG. 51 is a Western blot of Caspase-1 activation (p20 subunit) in primary human RPE cells transfected with Alu RNA, with short peptide (Panx1[10]), which blocks P2X7 pore function but not cation flux (vs. scrambled peptide: Scr Panx1[10]).
Figure 52:
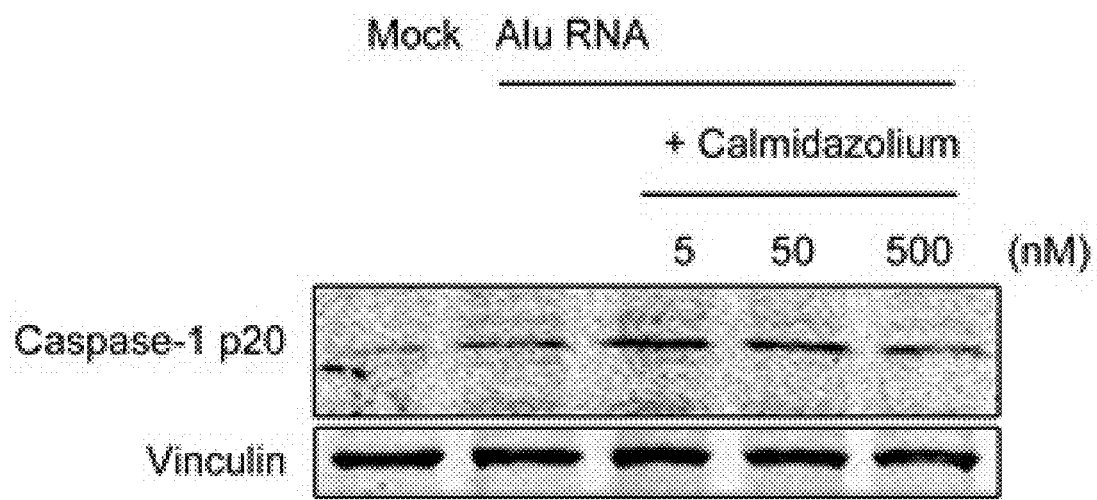
FIG. 52 is a Western blot of Caspase-1 activation (p20 subunit) in primary human RPE cells transfected with Alu RNA, with calmidazolium (FIG. 32 provides the chemical structure of IC- and EC-d4T used), which blocks P2X7 cation flux but not pore function.

Consistent with the idea that NRTIs block Alu-induced P2X7-mediated inflammasome activation via a mechanism involving dye uptake, Alu RNA-induced Caspase-1 activation was inhibited by a small peptide that blocks P2X7-mediated dye uptake and LPS/ATP-induced inflammasome activation, but not cation flux (Pelegrin and Surprenant, 2006) (FIG. 51). On the other hand, Alu-induced Caspase-1 activation was not inhibited by calmidazolium, which selectively blocks P2X7-mediated cation flux but not dye uptake (FIG. 52).

Figure 32:
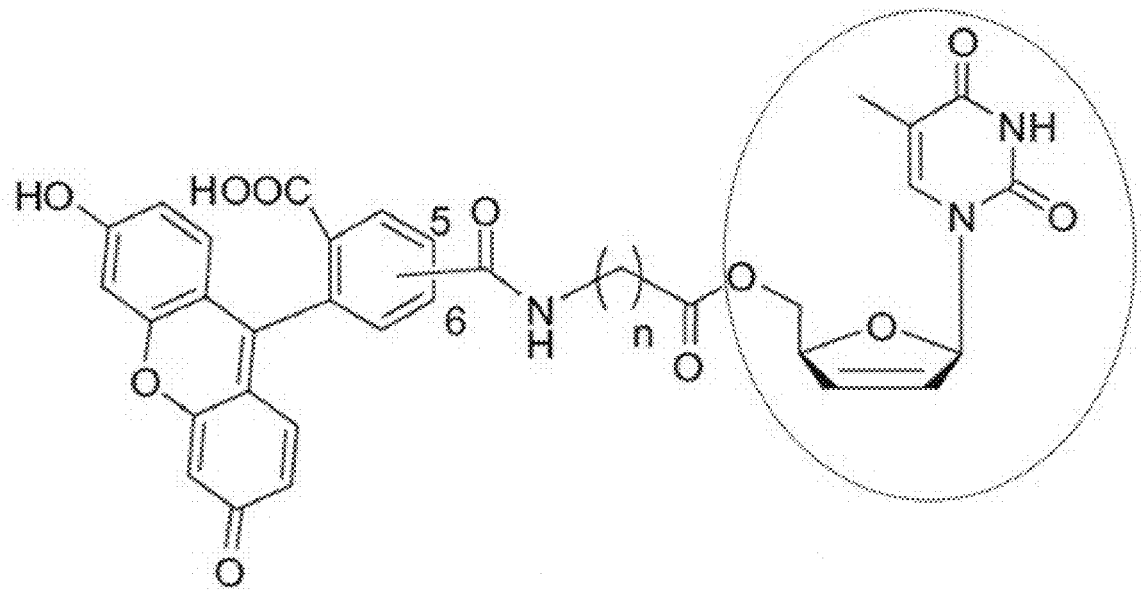
FIG. 32 shows a cell permeant variant of d4T (IC-d4T), where "n" group is equal to 11. Derivatives include cell permeant variants of 3TC, AZT, ABC, where the nucleobase group (circled) may be replaced, in various embodiments, by 3TC, AZT, ABC, or methoxy-variants of d4T, 3TC, AZT, ABC (FIG. 29-31), or derivatives thereof.
Figure 53:
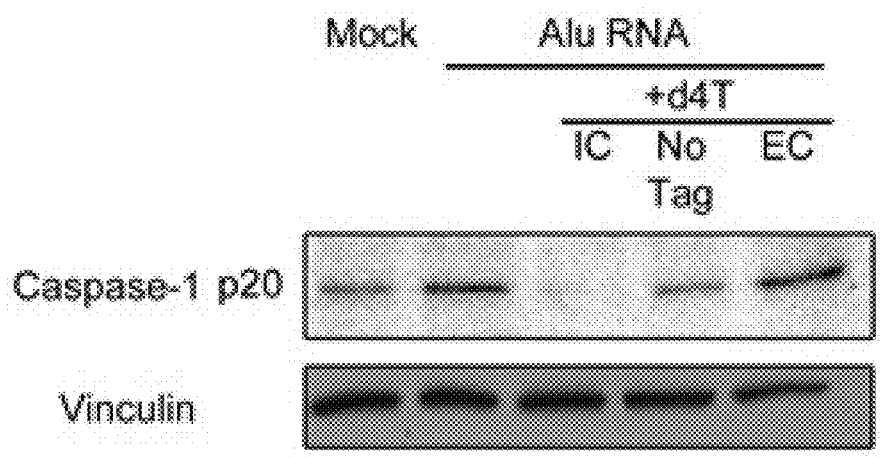
FIG. 53 is a Western blot of Caspase-1 activation (p20 subunit) in primary human RPE cells transfected with Alu RNA, with cell permeable (IC), cell-impermeable (EC), or unmodified (no tag) d4T.
Figure 54:
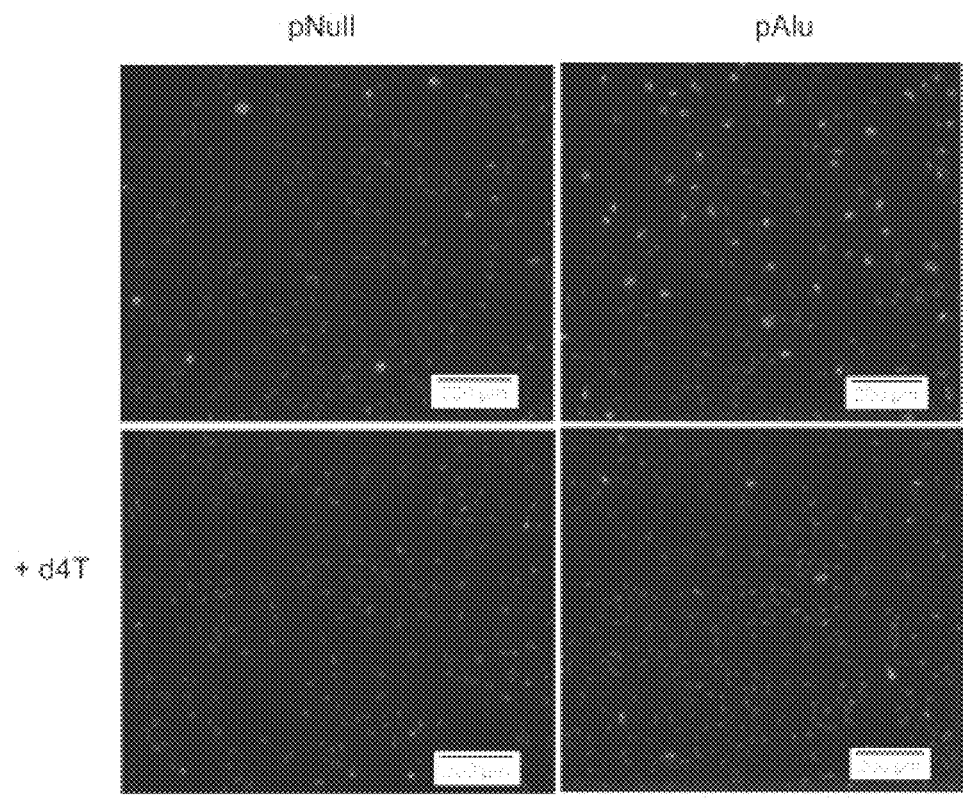
FIG. 54 shows that d4T prevents pAlu-induced mitochondrial ROS generation in primary human RPE cells.

Furthermore, the intracellular C-terminus of P2X7 governs P2X7-associated dye uptake, and a version of d4T that is not cell permeable (Agarwal et al., 2011) does not block caspase-1 activation by Alu RNA (FIG. 53, FIG. 32). Consistent with antagonism at or downstream of P2X7, but upstream of mitochondrial dysfunction, d4T blocks mitochondrial ROS (mtROS) production, which are produced upon LPS/ATP stimulation (Adinolfi et al., 2005; Cruz et al., 2007; Garcia-Marcos et al., 2005; Nakahira et al., 2011) and Alu overexpression (Tarallo et al., 2012) was measured by MitoSOx assay (FIG. 54). Finally, d4T does not prevent P2X7-independent interleukin 1-beta secretion in PMA-primed THP-1 cells treated with crystalline monosodium urate (FIG. 11) (Martinon et al., 2006; Riteau et al., 2012).

To explore the potential therapeutic relevance of NRTIs beyond the Alu-induced model of geographic atrophy (GA), it was hypothesized that if NRTIs function as generic inflammasome inhibitors, then they might be broadly useful in other animal models of disease that are also driven by P2X7. In the NLRP3 inflammasome- and P2X7-driven graft-versus-host disease model (Jankovic et al., 2013; Wilhelm et al., 2010), treatment of mice receiving allogeneic bone marrow and T cells with d4T showed improved survival compared to saline treated controls (30-70% vs. 0%). Furthermore, in the NLRP3- and P2X7-driven model of sterile inflammation (McDonald et al., 2010), d4T reduced neutrophil migration to the focus of liver injury.

Interestingly, it has been shown that P2X7-dependent pore function alone can influence phenotype (Sorge et al., 2012). However, at present, there are not any FDA-approved drugs that selectively target downstream P2X7 signaling and not ion channel activation. Therefore, NRTIs could be valuable both clinically and experimentally in the selective targeting of P2X7 function.

A role for P2X7 in regulating HIV replication was recently proposed (Hazleton et al., 2012), and HIV patients have increased plasma IL-18 levels (Ahmad et al., 2002; Iannello et al., 2010), which decrease after treatment with NRTI-containing highly active anti-retroviral therapy (Stylianou et al., 2003). Notably, reduction of plasma IL-18 levels by NRTI treatment of HIV-1 infected patients did not significantly associate with viral load or CD4+ T-cell counts (David et al., 2000), indicating that NRTIs can dampen IL-18 levels before inhibition of viral replication occurs. IL-18 maturation requires pro-IL18 cleavage by active Caspase 1, which typically also requires P2X7 activation. Thus, the methods and experiments of the present disclosure are consistent with the idea that NRTIs can modulate HIV-induced cytokine expression independent of reverse transcriptase inhibition.

In some embodiments, d4T prevents RPE degeneration induced by Alu RNA in wild type mice. As shown in FIG. 1, sub-retinal Alu RNA administration to mice causes RPE degeneration in a mouse model of age-related macular degeneration. Indeed, as shown, d4T co-delivered to the vitreous humor of wild type mice prevents Alu RNA-induced RPE cell death in a dose-dependent manner at one week after delivery. The top row of FIG. 1 provides an ocular fundus photograph of mice receiving control PBS, or Alu RNA treatment, with or without increasing amounts of d4T (left to right). Arrows denote depigmented regions of RPE cell death, which resolve at highest dose of d4T. The bottom row of FIG. 1 shows an RPE flat mount, stained for intercellular junctions (ZO-1) in red that are disrupted upon Alu RNA administration, but restored to healthy RPE morphology/intercellular junctions at highest dose of d4T.

Figure 2:
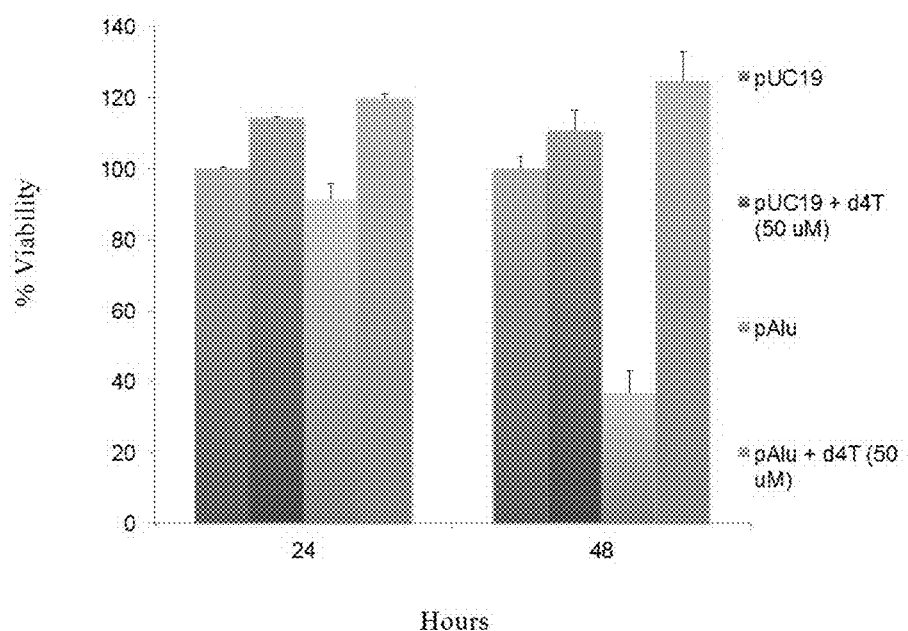
FIG. 2 provides a bar graph showing that human (HeLa) cells treated with an enforced expression plasmid for Alu RNA (pAluA) for denoted amounts of time exhibited profoundly reduced viability compared to a null plasmid (pUC19), as monitored by MTS proliferation assay and that d4T co-administration prevented cell death induced by Alu overexpression.

Meanwhile, in certain embodiments, d4T protects against cytotoxicity induced by plasmid expressing Alu RNA in vitro. FIG. 2 shows that human (HeLa) cells treated with an enforced expression plasmid for Alu RNA (pAluA) for denoted amounts of time exhibited profoundly reduced viability compared to a null plasmid (pUC19), as monitored by MTS proliferation assay, and that d4T co-administration prevented cell death induced by Alu overexpression.

Figure 3:
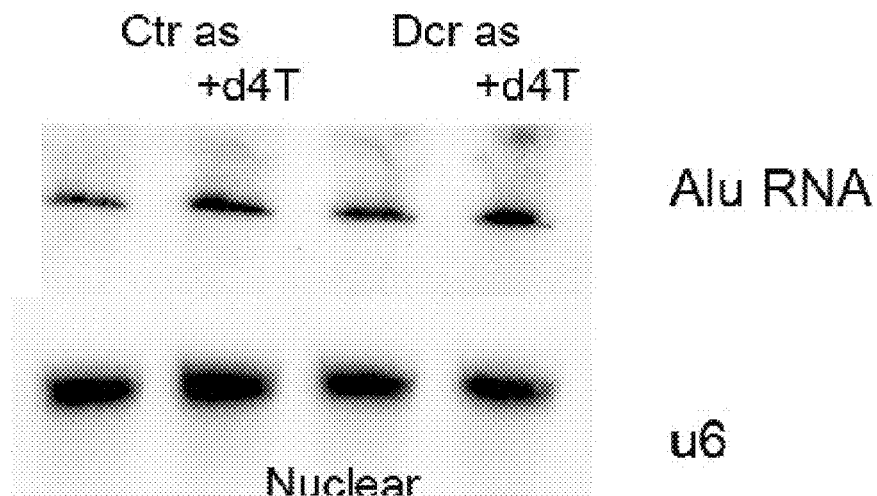
FIG. 3 shows the results of Northern blotting using an Alu-specific probe. As presented in FIG. 3, primary human RPE cells treated with antisense oligonucleotides targeting DICER1 (Dcr as) (lane 3 (third lane from left)) show increased Alu RNA levels in the nuclear compartment compared to control antisense oligonucleotides (Ctr as) (lane 1 (leftmost)), and co-administration of d4T (lanes 2 and 4) does not reduce Alu RNA levels. u6 (bottom row) is shown as a loading control for nuclear fraction.

In some exemplary embodiments, d4T does not rescue cytotoxicity via reduction in Alu RNA levels. As presented in FIG. 3, primary human RPE cells treated with antisense oligonucleotides targeting DICER1 (Dcr as) (lane 3 (third lane from left)) show increased Alu RNA levels in the nuclear compartment compared to control antisense oligonucleotides (Ctr as) (lane 1 (leftmost)), monitored by Northern blotting using an Alu-specific probe. Meanwhile, co-administration of d4T (lanes 2 and 4) does not reduce Alu RNA levels. FIG. 3 shows u6 (bottom row) as a loading control for nuclear fraction.

Figure 4:
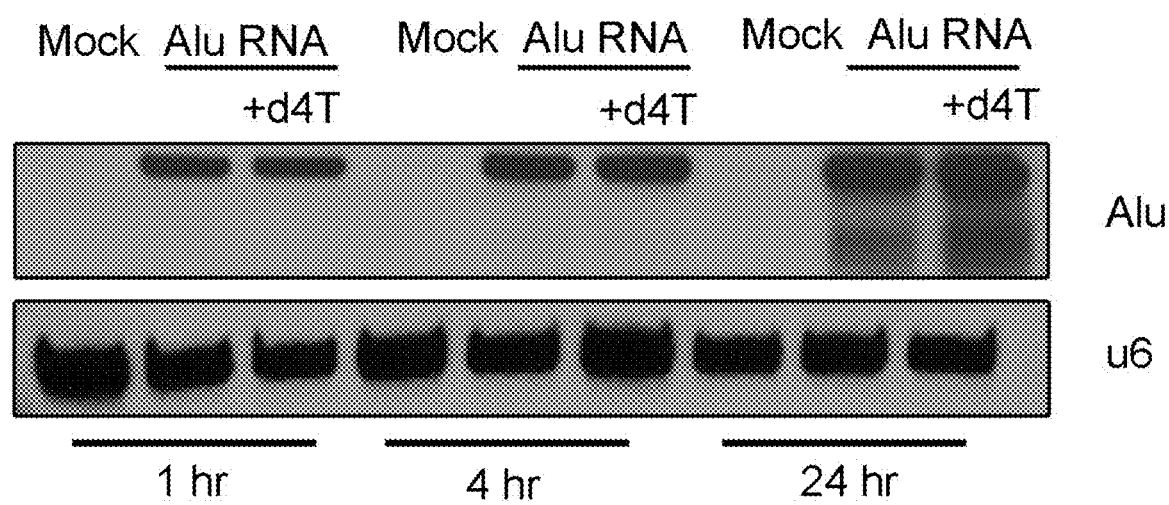
FIG. 4 provides another example of the results of Northern blotting using an Alu-specific probe. As presented in FIG. 4, co-administration of d4T does not change Alu RNA levels at 1, 4, or 24 hours after transfection in the nuclear fraction of human RPE cells transfected with Alu RNA, with or without d4T, as detected by Northern blotting using an Alu-specific probe. u6 (bottom row) is shown as loading control for nuclear fraction in FIG. 4.

Moreover, in some embodiments, d4T does not reduce Alu RNA levels. For example, primary human RPE cells may be transfected with Alu RNA, with or without d4T. (FIG. 4) And, as presented in FIG. 4, co-administration of d4T does not change Alu RNA levels at 1, 4, or 24 hours after transfection in the nuclear fraction, as detected by Northern blotting using an Alu-specific probe. U6 (bottom row) is shown as loading control for nuclear fraction in FIG. 4.

Figure 5:
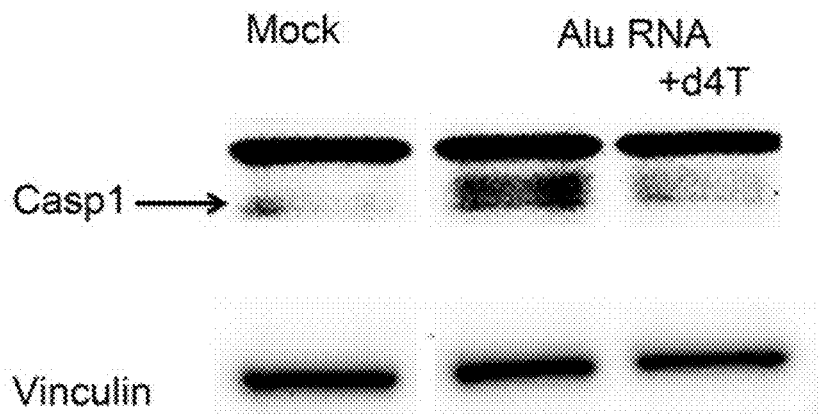
FIG. 5 provides the results of a Western blot showing that Alu RNA causes Caspase-1 maturation in primary human RPE cells at 24 hours after Alu administration (top, middle lane, lower band), which is blocked by co-treatment with d4T (100 uM; rightmost lane). The bottom row is a vinculin loading control.

The present disclosure further provides that, in some embodiments, d4T inhibits inflammasome activation by Alu RNA. Indeed, Alu RNA causes NLRP3 inflammasome activation, which is marked by processing of the enzyme Caspase 1, and FIG. 5 provides a Western blot showing that Alu RNA causes Caspase-1 maturation in primary human RPE cells at 24 hours after Alu administration (Top, Lane 2, lower band), which is blocked by co-treatment with d4T (100 uM; Lane 3). The bottom row in FIG. 5 is a vinculin loading control.

Figure 6:
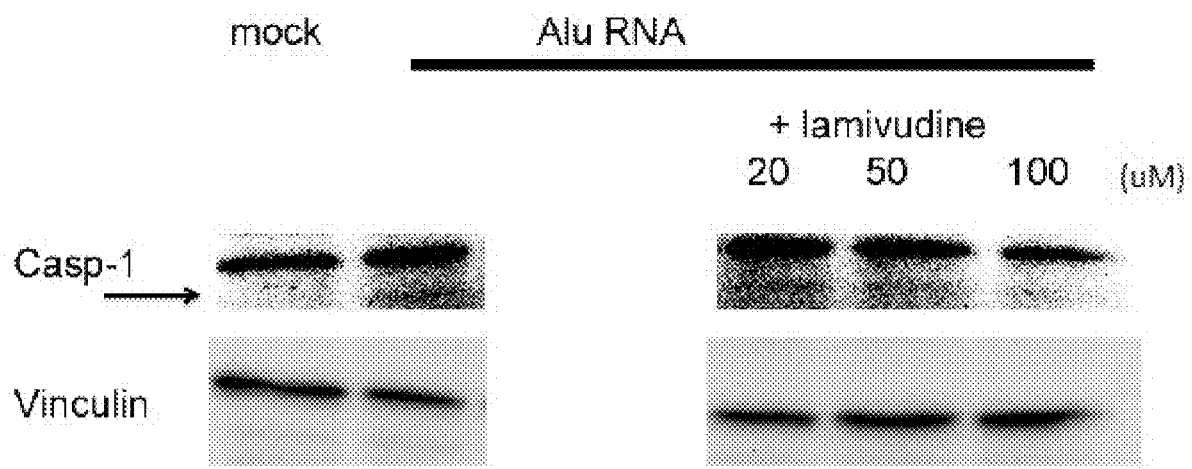
FIG. 6 is a Western blot showing that Alu RNA causes Caspase-1 maturation in primary human RPE cells at 24 hours after Alu administration (top, middle lane, lower band), which is blocked with co-treatment with 3TC (20-100 uM; rightmost lane), wherein the lowermost band is the loading control, vinculin.

In certain embodiments, 3TC inhibits inflammasome activation by Alu RNA. Indeed, Alu RNA causes NLRP3 inflammasome activation, which is marked by processing of the enzyme Caspase 1. FIG. 6 is a Western blot showing that Alu RNA causes Caspase-1 maturation in primary human RPE cells at 24 hours after Alu administration (top, lane 2, lower band), which is blocked with co-treatment with 3TC (20-100 uM; lane 3). On the bottom, the loading control, vinculin, is visible.

Figure 7:
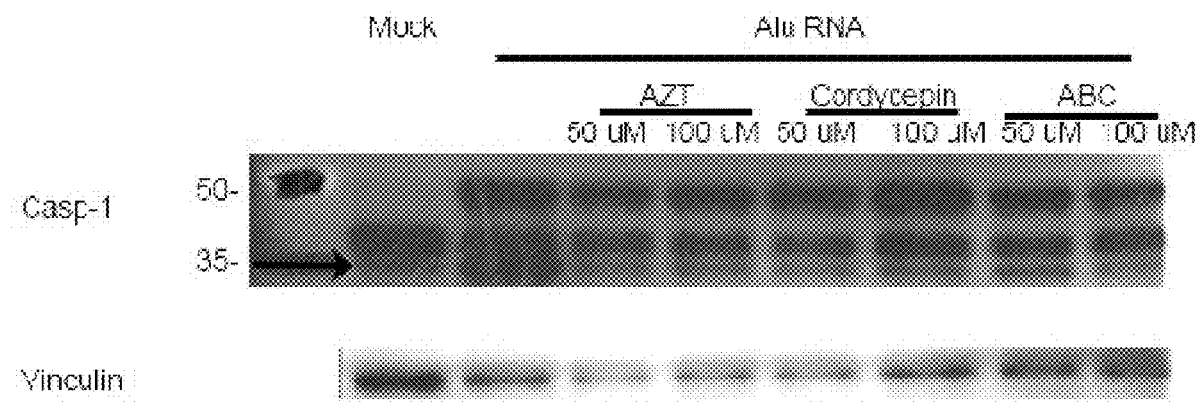
FIG. 7 is a Western blot showing that Alu RNA causes Caspase-1 maturation in primary human RPE cells at 24 hours after Alu administration (top, middle lane, lower band), which is blocked with co-treatment with azidothymidine (AZT), cordycepin, and abacavir (ABC) (50-100 uM; lanes 3-8 from left). The loading control vinculin is shown on the bottom.

Next, FIG. 7 provides evidence of AZT, cordycepin, and abacavir inhibition of inflammasome activation by Alu RNA. Indeed, Alu RNA causes NLRP3 inflammasome activation, which is marked by processing of the enzyme Caspase 1. FIG. 7 is a Western blot showing that Alu RNA causes Caspase-1 maturation in primary human RPE cells at 24 hours after Alu administration (top, lane 2, lower band), which is blocked with co-treatment with azidothymidine (AZT), cordycepin, and abacavir (ABC) (50-100 uM; Lanes 3-8). Again, the loading control vinculin is shown on the bottom.

Figure 8:
FIG. 8 provides a gel showing that primary human RPE cells treated with LPS/ATP, a classic inflammasome activator, exhibit increased Casp-1 activation, and phosphorylation of IRAK4, which is also a marker of inflammasome signaling via the cell surface receptor adaptor protein MyD88. Moreover, as shown in FIG. 8, d4T (25/100 uM) blocks Casp-1 activation and IRAK4 phosphorylation induced by LPS/ATP. Vinculin was used as the loading control in the gel of FIG. 8. Additionally, as shown, LPS and ATP activate the NLRP3 inflammasome only in combination.

In certain embodiments, the present disclosure provides that d4T inhibits inflammasome activation by LPS/ATP. As such, FIG. 8 provides a gel showing that primary human RPE cells treated with LPS/ATP, a classic inflammasome activator, exhibit increased Casp-1 activation, and phosphorylation of IRAK4, which is also a marker of inflammasome signaling via the cell surface receptor adaptor protein MyD88. Moreover, as shown in FIG. 8, d4T (25/100 uM) blocks Casp-1 activation and IRAK4 phosphorylation induced by LPS/ATP. The loading control in FIG. 8 is vinculin. Furthermore, as shown, LPS and ATP activate the NLRP3 inflammasome only in combination, thus treatment with one or the other alone is useful as a control for this experiment.

Figure 9:
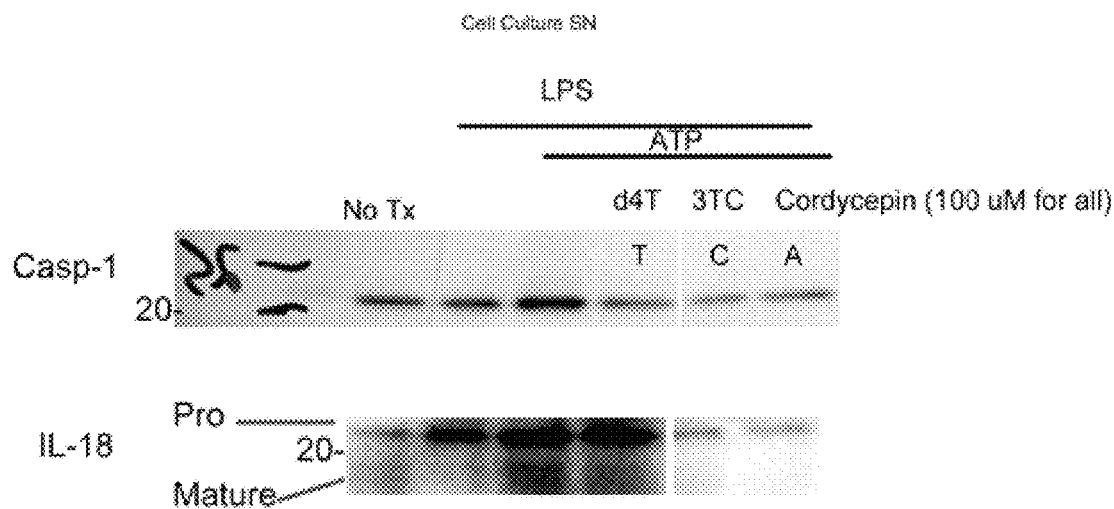
FIG. 9 provides the results of Western blotting, wherein d4T, 3TC, and cordycepin (at 100 uM), all di-deoxy nucleoside reverse transcriptase inhibitors, are shown to inhibit Caspase-1 activation (active p20 band, top) and IL-18 maturation (bottom) induced by LPS/ATP. To produce FIG. 9, cell culture supernatants were collected after (i) no treatment, (ii) LPS treatment, or (iii) LPS/ATP treatment of mouse bone marrow-derived macrophages and run on Western blotting probing with antibodies for Caspase-1 and IL-18.

The present disclosure further provides that, in exemplary embodiments, d4T and other NRTIs reduce inflammasome activation by LPS/ATP. As presented in FIG. 9, d4T, 3TC, and cordycepin (at 100 uM), all di-deoxy nucleoside reverse transcriptase inhibitors, inhibit Caspase-1 activation (active p20 band, top) and IL-18 maturation (bottom) induced by LPS/ATP. To produce FIG. 9, cell culture supernatants were collected after (i) no treatment, (ii) LPS treatment, or (iii) LPS/ATP treatment of mouse bone marrow-derived macrophages and run on Western blotting probing with antibodies for Caspase-1 and IL-18.

Figure 10:
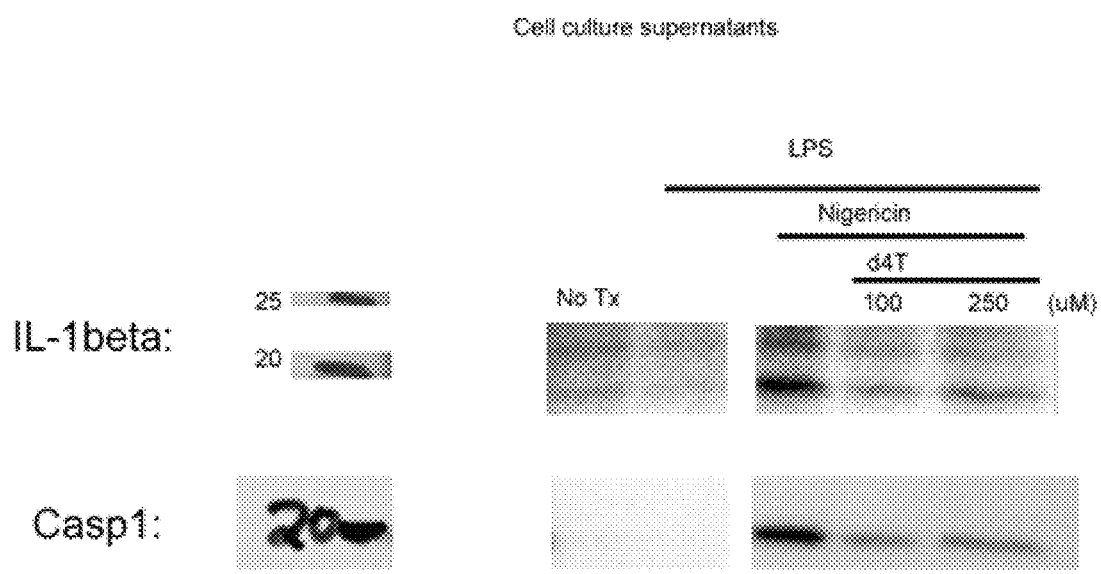
FIG. 10 provides the result of a Western blot showing that d4T (100, 250 uM) inhibits IL-1 beta maturation (top, 18 and 22 kDa forms) and Caspase-1 activation (active p20 band, bottom) induced by nigericin. To produce FIG. 10, cell culture supernatants were collected after (i) no treatment, (ii) LPS treatment, or (iii) LPS/nigericin treatment of mouse bone marrow-derived macrophages and run on Western blotting probing with antibodies for IL-1 beta and Caspase-1.

In some embodiments of the present disclosure, d4T inhibits nigericin-induced inflammasome activation. Per FIG. 10, d4T (100, 250 uM) inhibits IL-1 beta maturation (top, 18 and 22 kDa forms) and Caspase-1 activation (active p20 band, bottom) induced by nigericin. Cell culture supernatants were collected after (i) no treatment, (ii) LPS treatment, or (iii) LP S/nigericin treatment of mouse bone marrow-derived macrophages, and run on Western blotting probing with antibodies for IL-1 beta and Caspase-1. FIG. 10 shows the results of these efforts.

Figure 11:
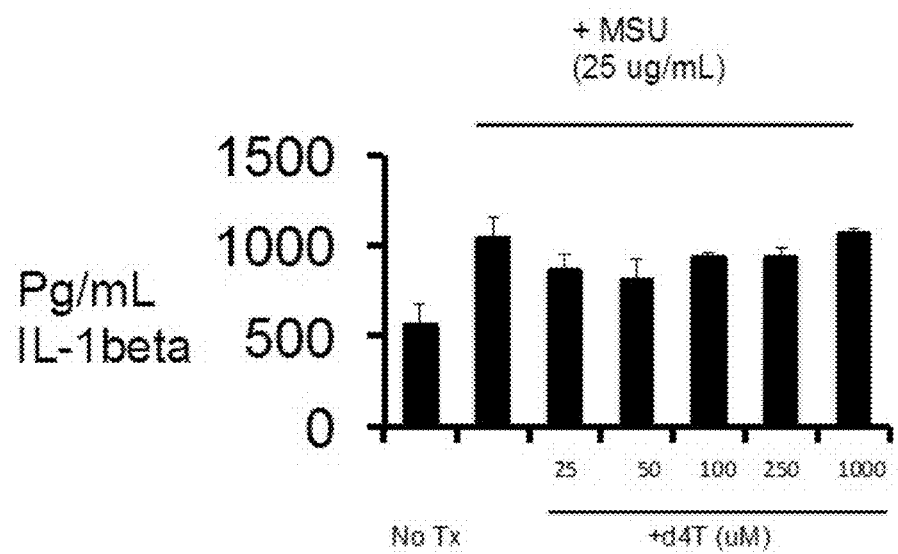
FIG. 11 shows a bar graph illustrating that d4T does not inhibit IL-1 beta secretion from PMA-differentiated THP-1 monocytes induced by monosodium urate (MSU).

Additionally, in some embodiments, d4T does not inhibit IL-1 beta secretion from PMA-differentiated THP-1 monocytes induced by MSU. Human THP-1 monocytes were differentiated into macrophages with PMA. As shown in FIG. 11, treatment with monosodium urate (MSU), a known inflammasome activator, increased IL-1 beta secretion compared to non-treated cells, whereas d4T co-administration at a range of doses (25-1000 uM) did not significantly affect IL-1beta secretion. Further, d4T does not block MSU-induced IL-1 beta secretion as determined by ELISA (n=3-4).

Figure 12:
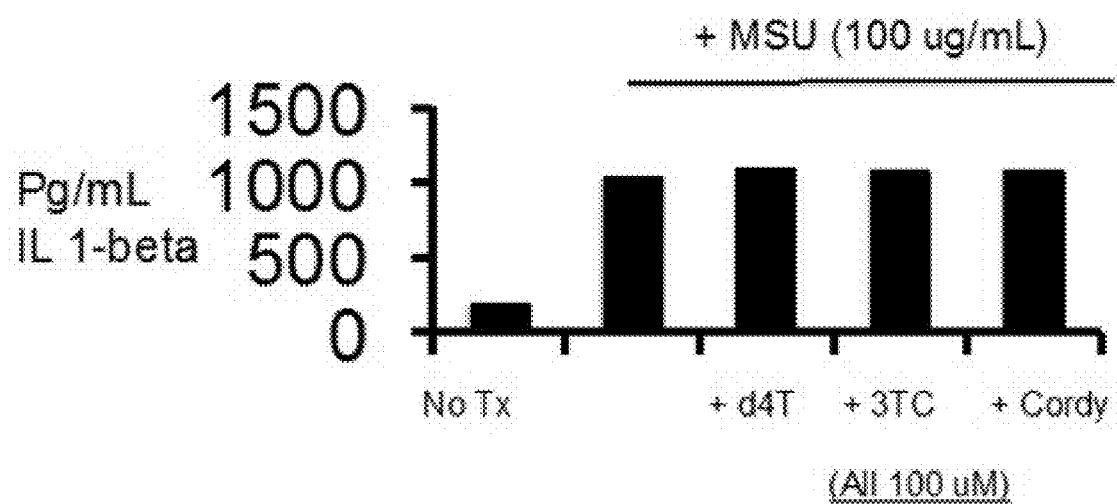
FIG. 12 is a bar graph, which shows that d4T and other nucleoside reverse transcriptase inhibitors do not inhibit IL-1 beta secretion from PMA-differentiated THP-1 monocytes induced by MSU. Human THP-1 monocytes were differentiated into macrophages with PMA. Their treatment with MSU increased IL-1 beta secretion compared to non-treated cells, as shown in FIG. 12, while co-administration of d4T, 3TC, or cordycepin (all are di-deoxy nucleotide analogs) at a range of doses (25-1000 uM) did not significantly affect IL-1beta secretion.

In certain embodiments, d4T and other nucleoside reverse transcriptase inhibitors do not inhibit IL-1 beta secretion from PMA-differentiated THP-1 monocytes induced by MSU. To illustrate this, human THP-1 monocytes were differentiated into macrophages with PMA. Treatment with MSU increased IL-1 beta secretion compared to non-treated cells. (FIG. 12) Meanwhile d4T, 3TC, or cordycepin (all are di-deoxy nucleotide analogs) co-administration at a range of doses (25-1000 uM) did not significantly affect IL-1beta secretion, as shown in FIG. 12.

Figure 13:
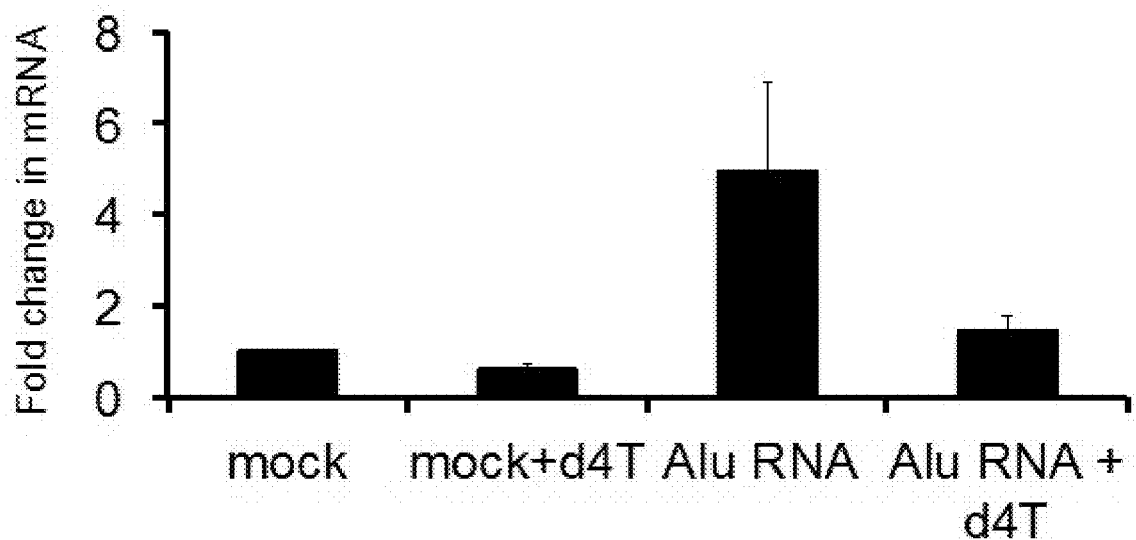
FIG. 13 is a graph, which provides that d4T reduces NLRP3 priming induced by Alu RNA. Indeed, as shown in FIG. 13, Alu RNA transfection increases NLRP3 mRNA levels in primary human RPE cells at 16 hours, an event termed "priming" (Y-axis) compared to mock (transfection reagent alone). This effect is blunted by co-administration of d4T (100 uM) and normalized to 18S RNA control.

Next, in some embodiments, d4T reduces NLRP3 priming induced by Alu RNA. Indeed, as provided in the bar graph of FIG. 13, Alu RNA transfection increases NLRP3 mRNA levels in primary human RPE cells at 16 hours, an event termed "priming" (Y-axis) compared to mock (transfection reagent alone). This effect is blunted by co-administration of d4T (100 uM) and normalized to 18S RNA control.

Figure 14:
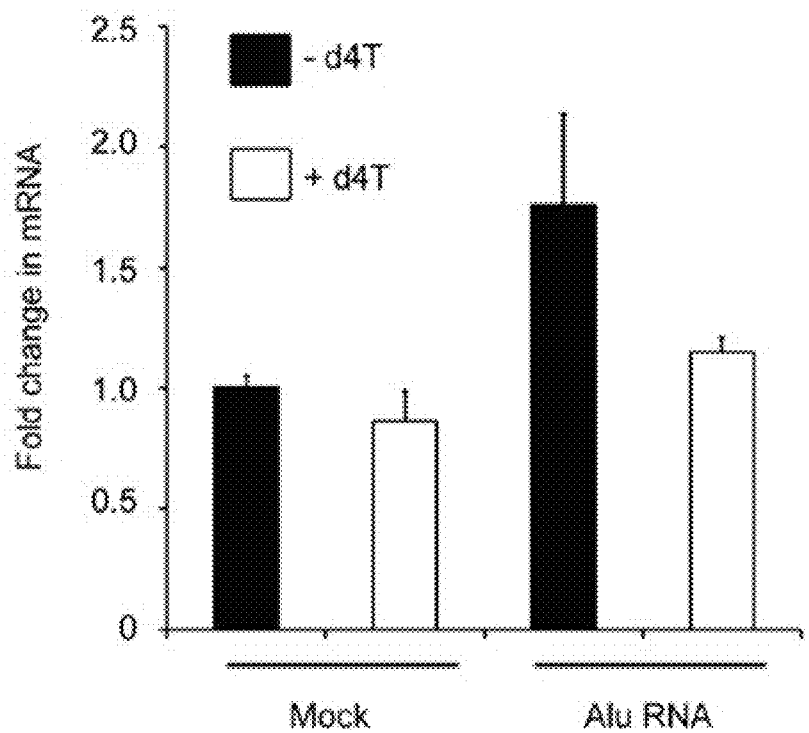
FIG. 14 illustrates, in graph format, that Alu RNA transfection increases IL-1 beta mRNA levels in primary human RPE cells at 24 hours, an event termed "priming", (Y-axis) compared to mock (transfection reagent alone). This effect is blunted by co-administration of d4T (100 uM) and normalized to 18S RNA control.

Furthermore, in exemplary embodiments of the present disclosure, d4T reduces IL-1beta priming induced by Alu RNA. FIG. 14 illustrates that Alu RNA transfection increases IL-1 beta mRNA levels in primary human RPE cells at 24 hours, an event termed "priming", (Y-axis) compared to mock (transfection reagent alone). This effect is blunted by co-administration of d4T (100 uM) and normalized to 18S RNA control.

Figure 15:
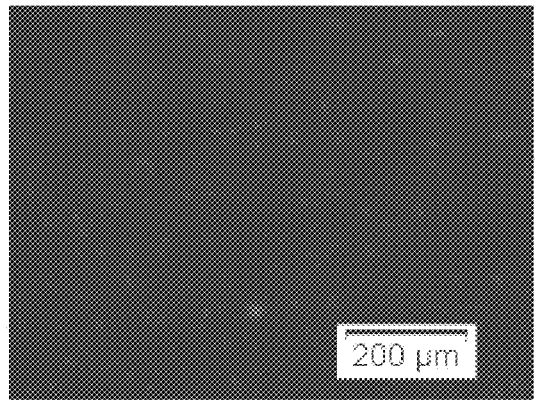
FIG. 15 shows that d4T reduces mitochondrial ROS caused by Alu expression. Indeed, FIG. 15 demonstrates that enforced expression of Alu (pAluA) causes increased mitochondrial reactive oxygen species (mtROS), as detected by MitoSox assay. In order to produce FIG. 15, primary human RPE cells were incubated with Alu expressing plasmid or control plasmid (pUC19) with or without d4T. After 15 hours cells were co-stained for mtROS (red) and for cell count, nuclei (blue; Hoechst DNA stain). Cells in the pAluA group exhibited greater mtROS staining (red) compared to pUC19 control, an effect that is reduced in pAluA+d4T treated cells.
Figure 15:
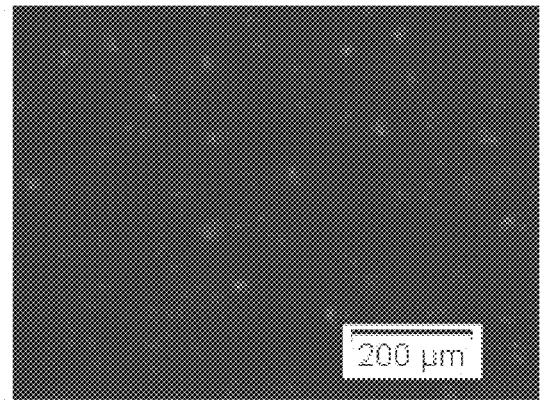
Figure 15:
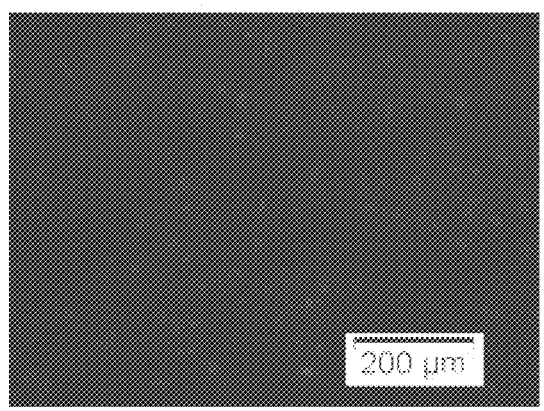
Figure 15:
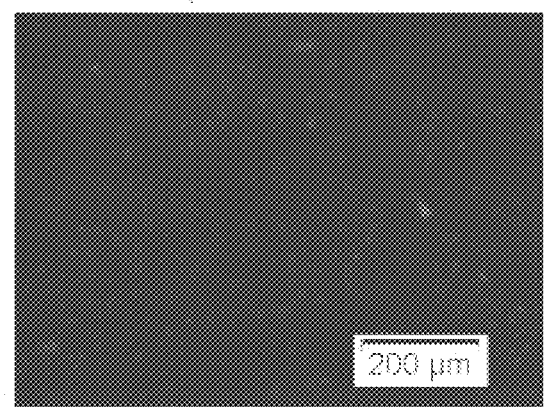

Meanwhile, in some embodiments, d4T reduces mitochondrial ROS caused by Alu expression. FIG. 15 demonstrates that enforced expression of Alu (pAluA) causes increased mitochondrial reactive oxygen species (mtROS), as detected by MitoSox assay. In order to produce FIG. 15, primary human RPE cells were incubated with Alu expressing plasmid or control plasmid (pUC19) with or without d4T. After 15 hours cells were co-stained for mtROS (red) and for cell count, nuclei (blue; Hoechst DNA stain). Cells in the pAluA group exhibited greater mtROS staining (red) compared to pUC19 control, an effect that is reduced in pAluA+d4T treated cells.

Figure 16:
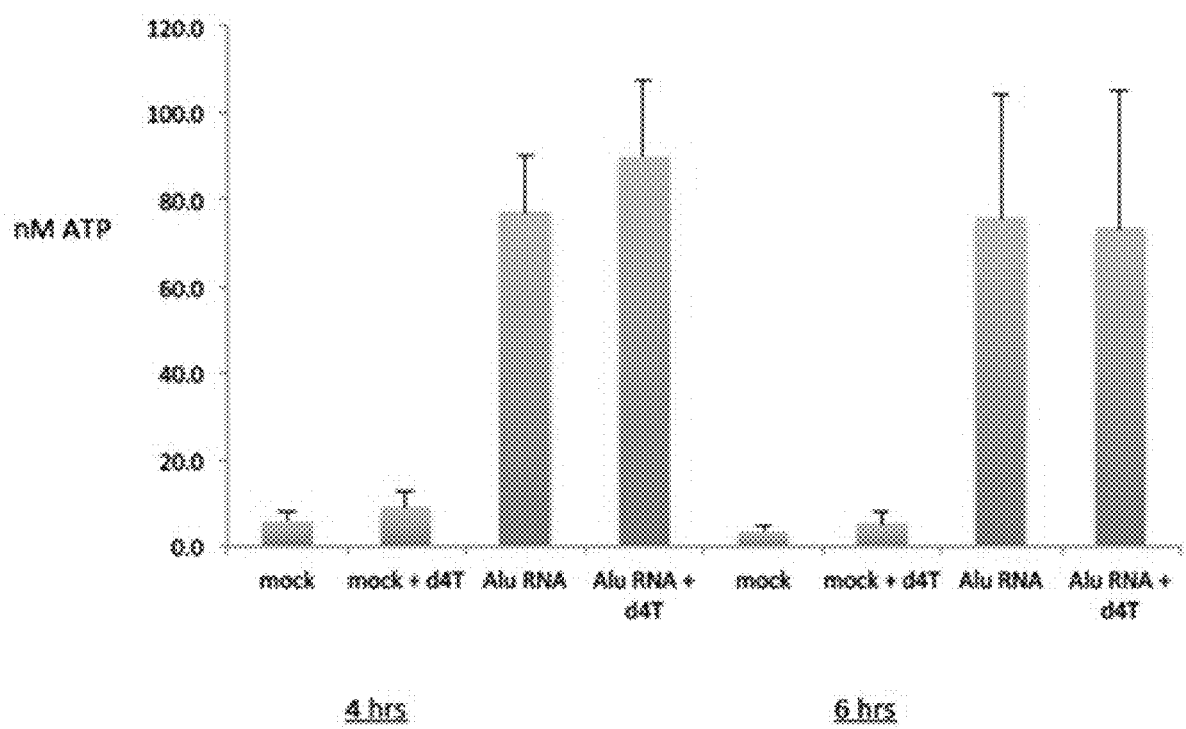
FIG. 16 provides a graph showing that d4T does not inhibit ATP release induced by Alu RNA. Moreover, primary human RPE cells treated with Alu RNA, for the times indicated in FIG. 16, release ATP. Cell culture supernatant was collected from mock or Alu RNA treated cells, with or without d4T, and ATP was detected using an ATP-dependent luciferase assay. Notably, d4T did not affect ATP release.

And in further embodiments, d4T does not inhibit ATP release induced by Alu RNA. (FIG. 16) Primary human RPE cells treated with Alu RNA for the times indicated release ATP. To provide FIG. 16, cell culture supernatant was collected from mock or Alu RNA treated cells, with or without d4T. ATP was detected using an ATP-dependent luciferase assay. And, notably, d4T did not affect ATP release.

Figure 17:
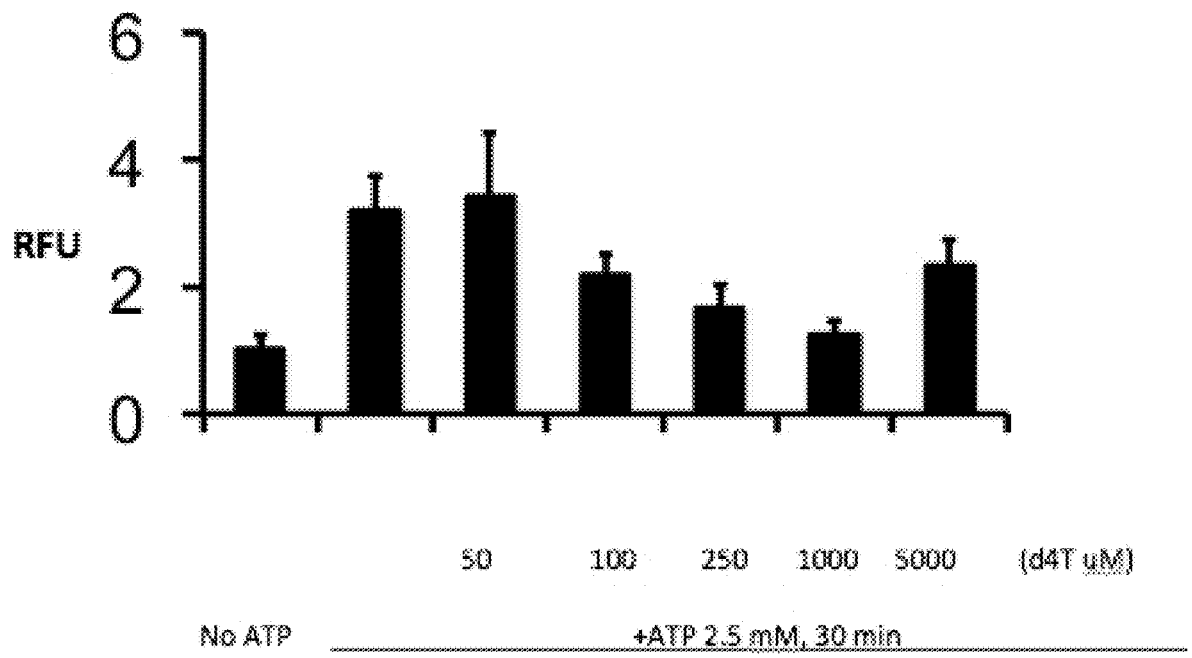
FIG. 17 shows that d4T reduces ATP-induced cell permeability to Yo-Pro1 (P2X7 receptor assay). Indeed, d4T dose-dependently reduced Yo-Pro entry induced by ATP, determined by an area-scan fluorescent measurement in a 96 well microplate reader.

In certain embodiments, d4T reduces ATP-induced cell permeability to Yo-Pro1 (P2X7 receptor assay), as shown in FIG. 17. To prepare FIG. 17, THP-1 cells differentiated into macrophages by PMA allowed entry of the large fluorescent dye Yo-Pro 1, in an assay for P2X7 receptor activity. It was observed that d4T dose-dependently reduced Yo-Pro entry induced by ATP, determined by an area-scan fluorescent measurement in a 96 well microplate reader. Indeed, FIG. 17 provides the results of the fluorescence measurement in relative fluorescence units (RFU, y-axis).

Figure 18:
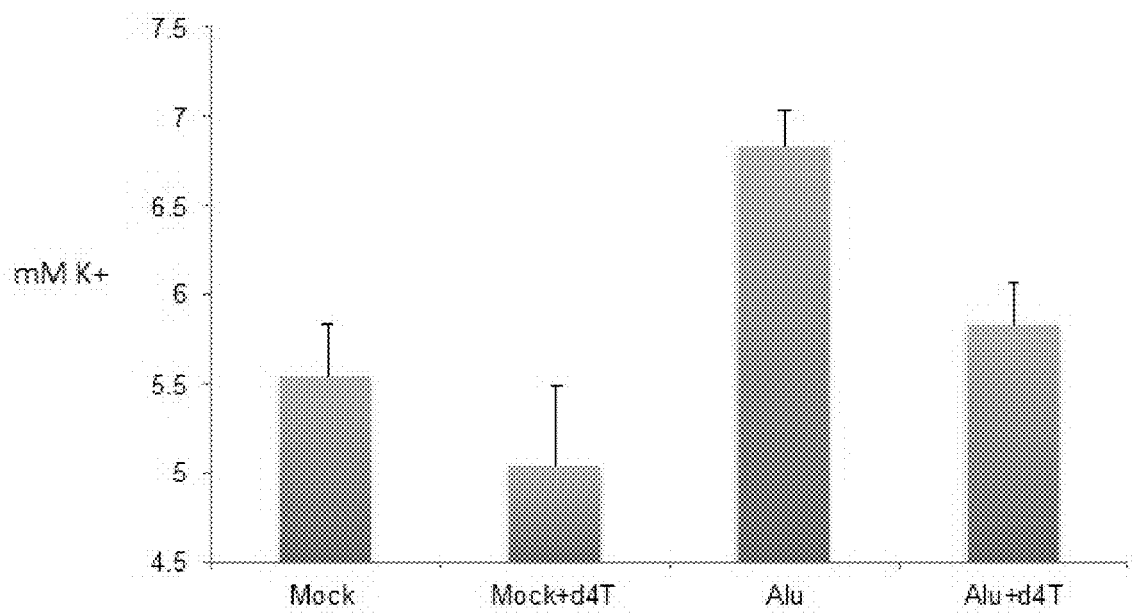
FIG. 18 illustrates, in graph format, that d4T reduces extracellular potassium levels, which increase after Alu RNA transfection. Indeed, cell culture potassium levels increase in primary human RPE cells treated with Alu RNA for 6 hours, an effect that is reduced by d4T co-administration. Potassium levels were determined in cell culture supernatants spectrophotometrically using a potassium-dependent pyruvate kinase assay.

Furthermore, it has been shown that d4T reduces extracellular potassium levels that increase after Alu RNA transfection. (FIG. 18) Indeed, cell culture potassium levels increase in primary human RPE cells treated with Alu RNA for 6 hours, an effect that is reduced by d4T co-administration. For FIG. 18, potassium levels were determined in cell culture supernatants spectrophotometrically using a potassium-dependent pyruvate kinase assay.

Figure 19:
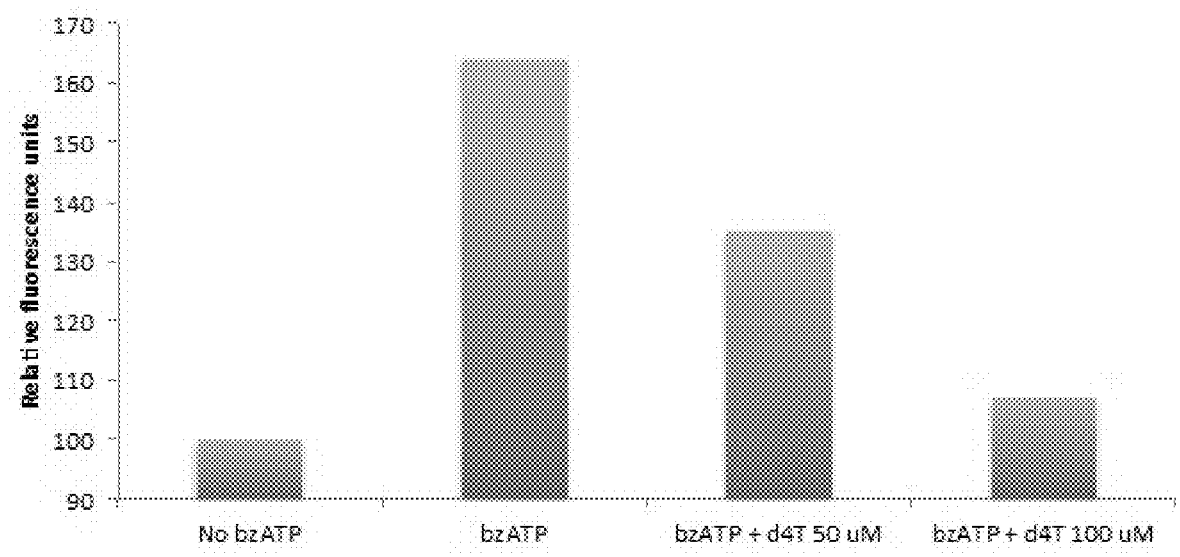
FIG. 19 shows that d4T blocks bzATP-induced cell permeability to Yo-Pro1 (P2X7 receptor assay). To prepare FIG. 19, d4T blocked YO-PRO-1 iodide entry in HEK293 cells stably expressing the human P2X7 receptor stimulated with the P2X7-selective agonist bzATP. Cells were pre-incubated with d4T for 30 minutes prior to addition of bzATP/YO-PRO, and fluorescence (in relative fluorescence units) at 485/515 nm was measured at t=30 minutes.

Next, in some embodiments, d4T blocks bzATP-induced cell permeability to Yo-Pro1 (P2X7 receptor assay), as shown in FIG. 19. d4T blocked YO-PRO-1 iodide entry in HEK293 cells stably expressing the human P2X7 receptor stimulated with the P2X7-selective agonist bzATP. Cells were pre-incubated with d4T for 30 minutes prior to addition of bzATP/YO-PRO, and fluorescence at 485/515 nm measured at t=30 minutes.

Moreover, d4T blocks Alu-induced RPE degeneration and Caspase-1 activation independent of reverse transcriptase inhibition.

In some embodiments, the present disclosure is directed to a compound having the structure(s) provided in FIG. 20. FIG. 20 includes a chemical structure of methoxy-d4T (me-d4T) and of d4T. As shown in FIG. 20, a single substitution of the ribose 5' hydroxyl group with a methoxy group (circled) has been designed by the inventors of the present disclosure to prevent d4T phosphorylation. Accordingly, in some embodiments, the present disclosure is directed to a compound comprising a single substitution of a ribose 5' hydroxyl group with a methoxy group. And, in some embodiments, the present disclosure provides compounds comprising a methoxy group in place of a ribose 5' hydroxyl group for preventing phosphorylation, such as d4T phosphorylation.

The present disclosure further provides the results of additional experiments in FIG. 21-FIG. 23. Indeed, FIG. 21 is a Western blot of Caspase-1 activation (p20 subunit) in primary human RPE cells transfected with Alu RNA±me-d4T; FIG. 22 shows cells, wherein unmodified d4T, but not me-d4T, blocks replication of a GFP-expressing lentivirus in HeLa cells; and FIG. 23 provides a graph illustrating that unmodified d4T, but not me-d4T, reduces mtDNA levels (normalized to chromosomal DNA exon-intron junction sequence) in primary mouse RPE cells as determined by real-time quantitative PCR. n=4, *p<0.05 by Student's t-test.

In some embodiments, it has been shown that Me-d4T (intraperitoneal injection) prevents Alu-induced RPE degeneration in mice. FIG. 24, top row, provides flat mounts stained for zonula occludens-1 (ZO-1; red), bottom row. Degeneration is outlined if FIG. 24 by blue arrowheads. Representative images of n=4 are shown.

Figure 25:
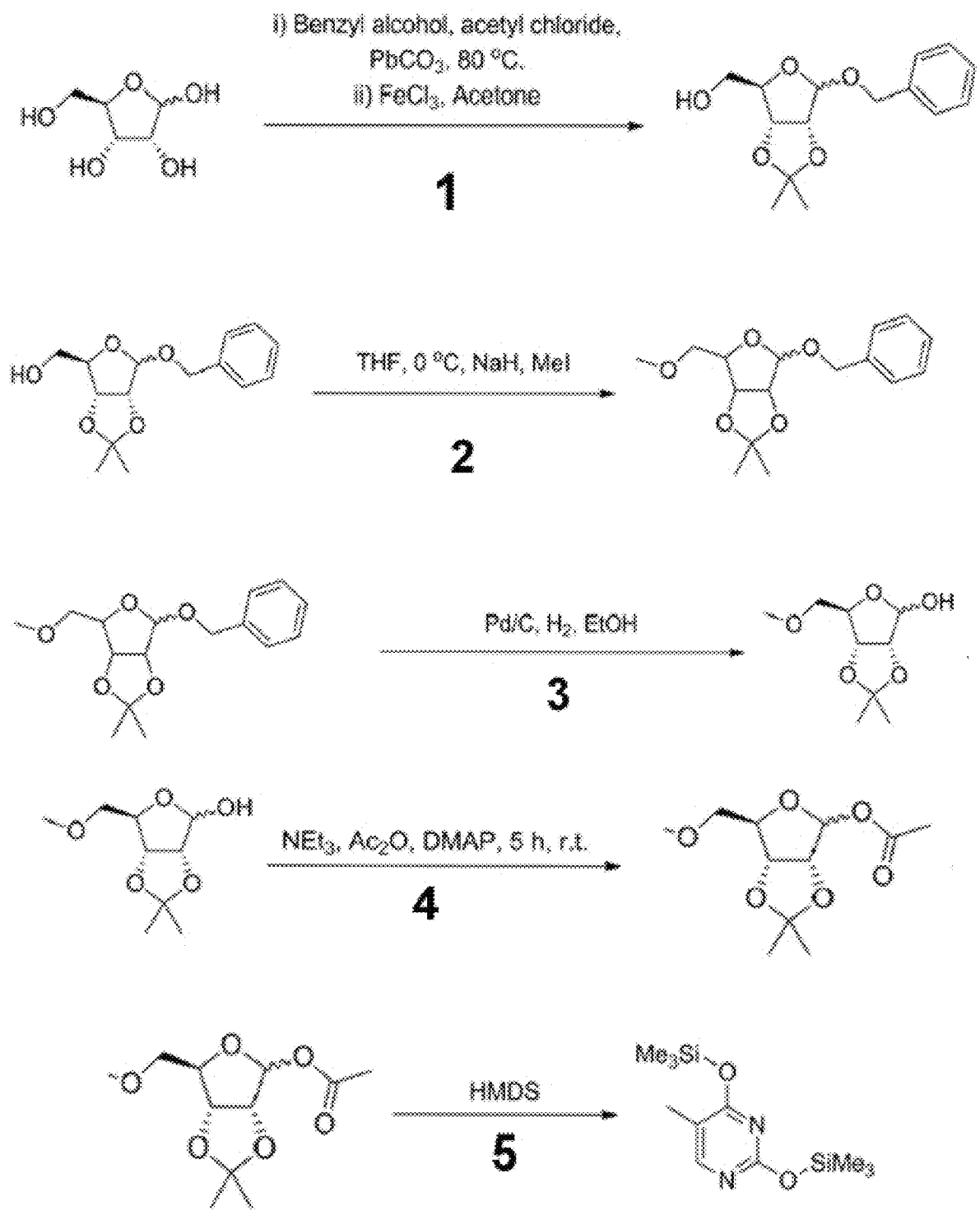
Figure 25:
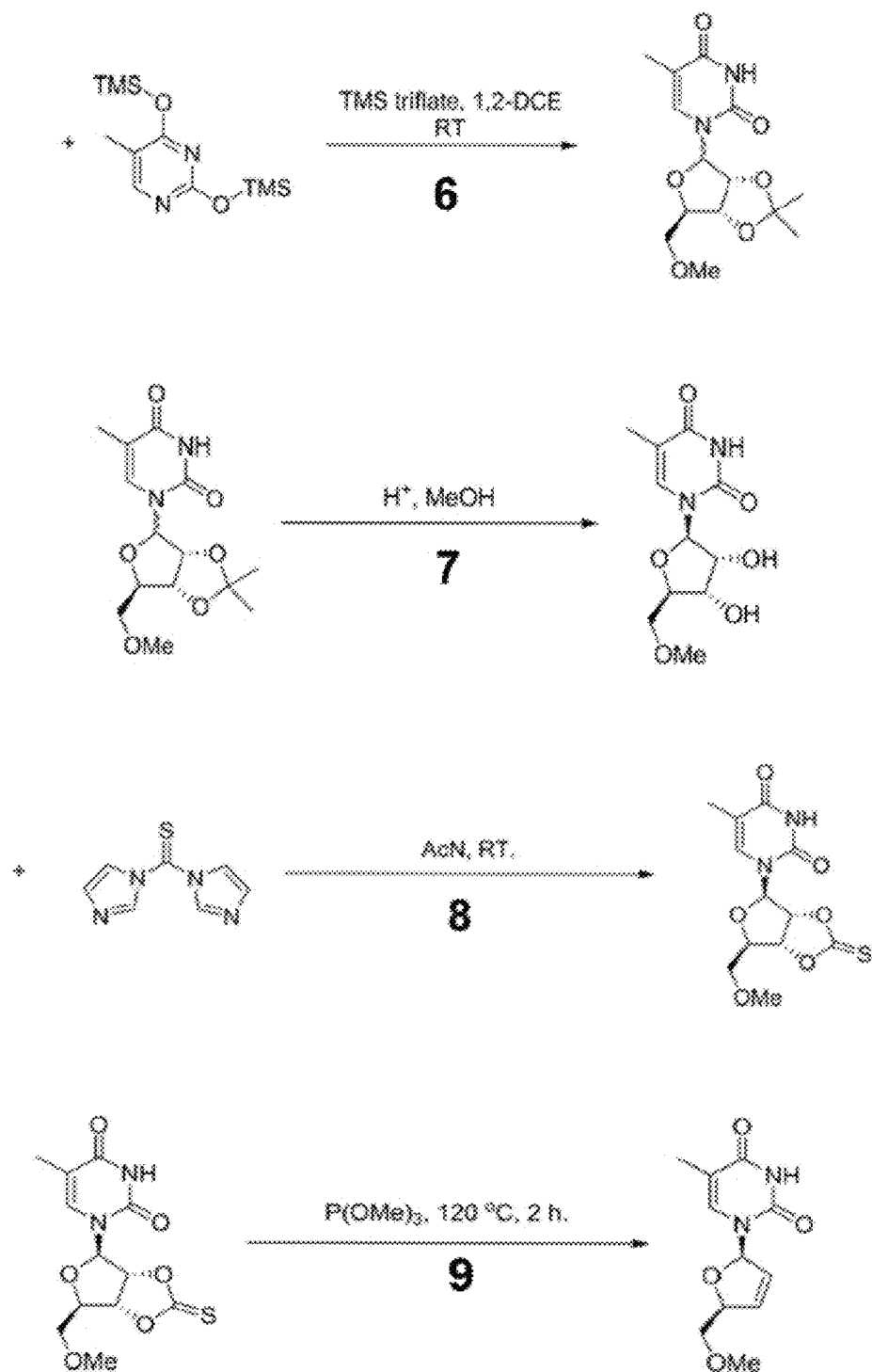
Figure 26:
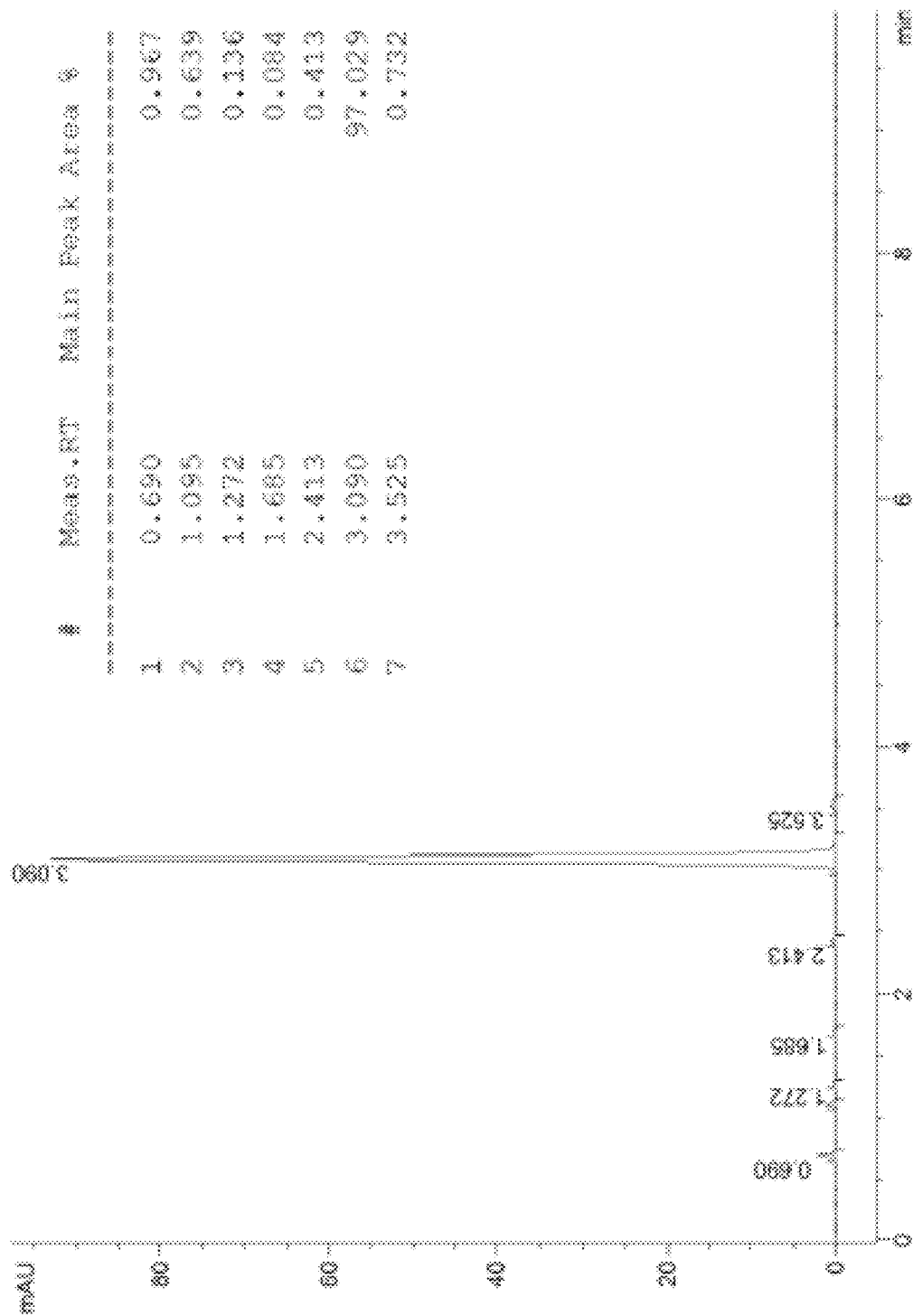
FIG. 26 is an HPLC chromatogram of me-d4T (peak #6) final product, >97% purity.
Figure 27:
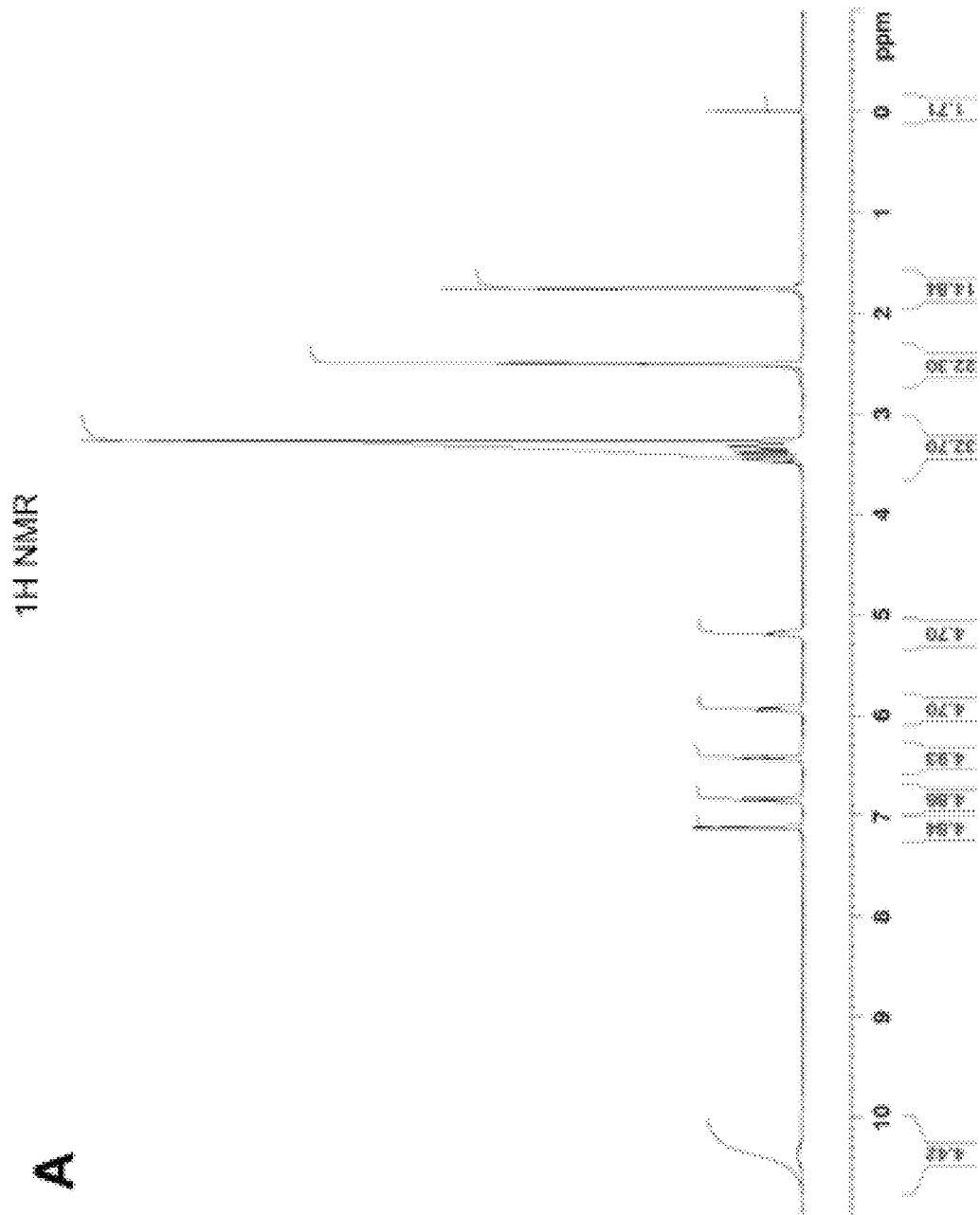
FIG. 27 is a 1H NMR spectroscopy of me-d4T final product, wherein the chemical shifts are consistent with the structure of me-d4T.
Figure 28:
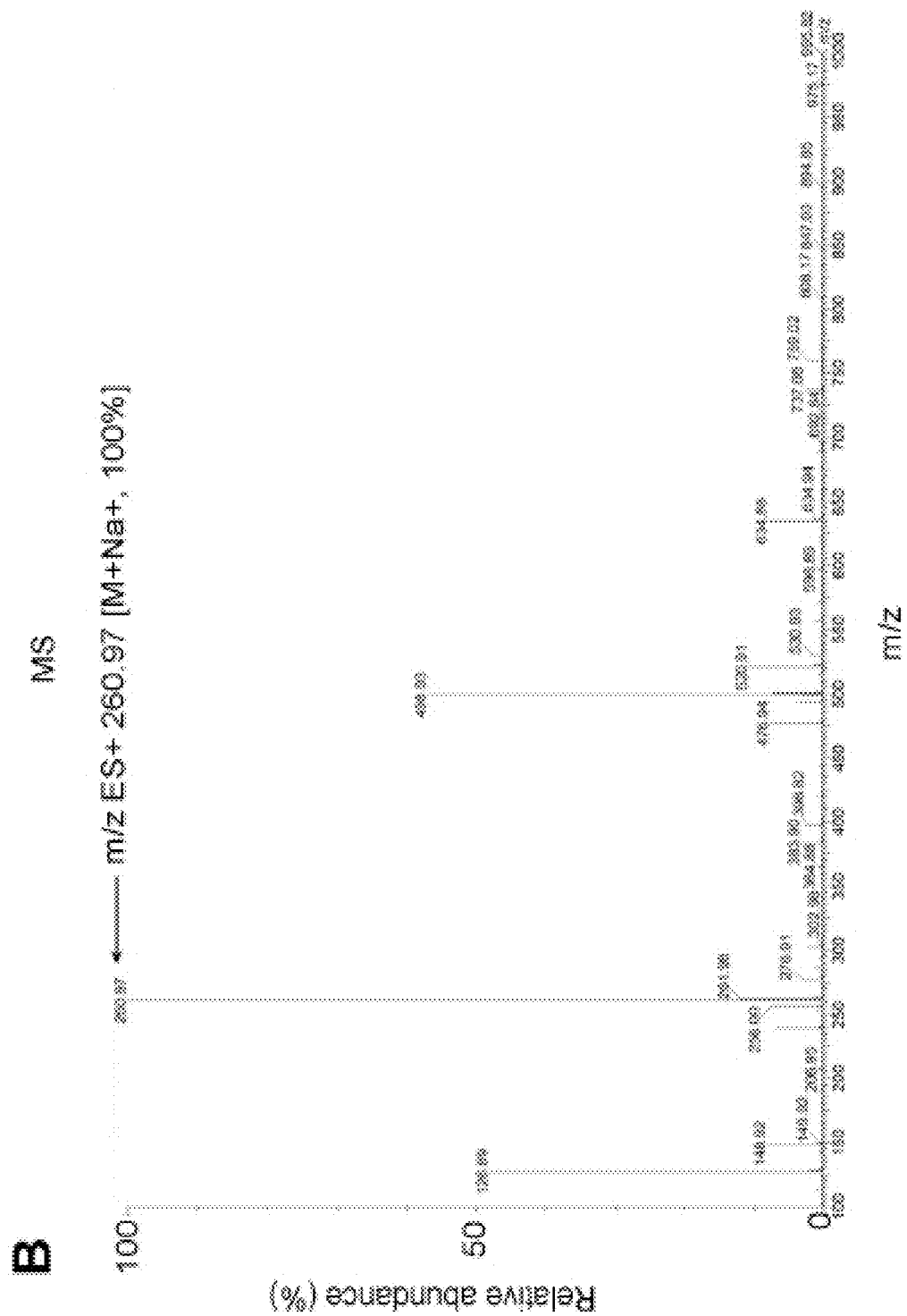
FIG. 28 provides the results of liquid chromatography/mass spectrometry of me-d4T final product, m/z ratio consistent with the structure of me-d4T.

Meanwhile, FIG. 25 provides a schematic overview of me-d4T synthesis, and FIG. 26 is an HPLC chromatogram of me-d4T (peak #6) final product, >97% purity. And FIG. 27 is a 1H NMR spectroscopy of me-d4T final product, wherein the chemical shifts are consistent with the structure, and FIG. 28 provides the results of liquid chromatography/ mass spectrometry of me-d4T final product, m/z ratio consistent with the structure.

Figure 29:
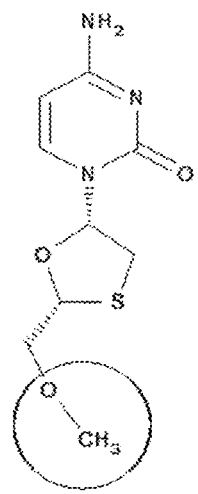
FIG. 29 provides the methoxy variant of a nucleoside analog. The chemical structure of 3TC (2'3' dideoxycytidine) is shown, wherein the methoxy variation (O-methyl group) of nucleoside analog is circled.
Figure 30:
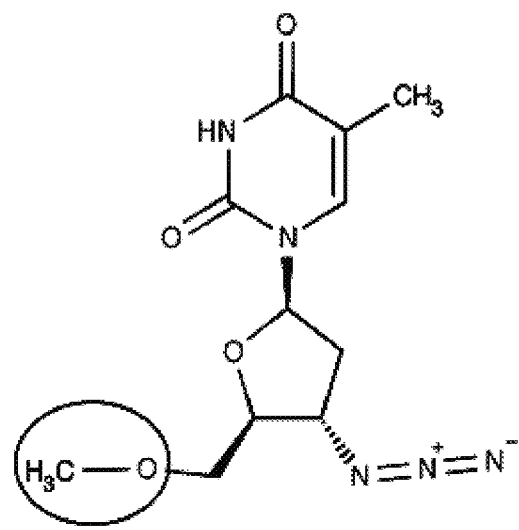
FIG. 30 provides the methoxy variant of a nucleoside analog. The chemical structure of AZT (3'-azido-2',3'-dideoxythymidine) is shown, wherein the methoxy variation (O-methyl group) of nucleoside analog is circled.
Figure 31:
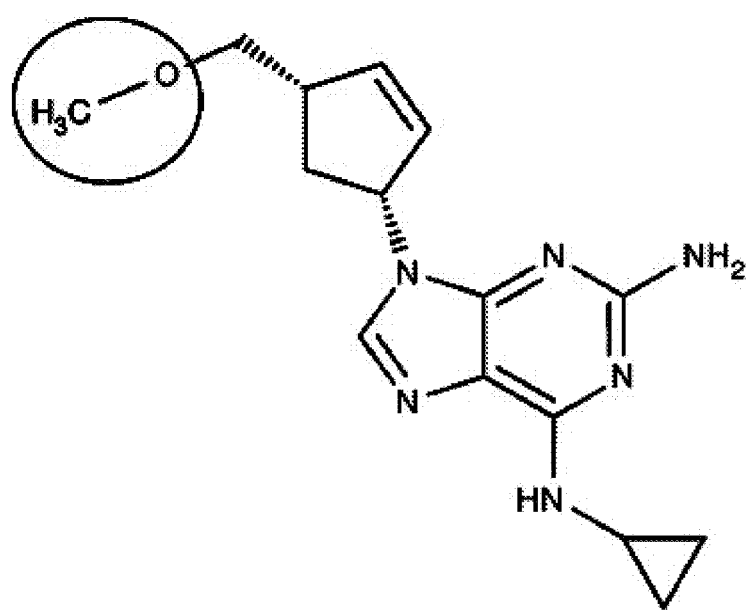
FIG. 31 provides the methoxy variant of a nucleoside analog. The chemical structure of ABC (cyclopropylaminopurinylcyclopentene) is shown, wherein the methoxy variation (O-methyl group) of nucleoside analog is circled.

FIG. 29, FIG. 30 and FIG. 31 provide for methoxy variants of nucleoside analogs. Specifically, FIG. 29 shows the chemical structure of 3TC (2'3' dideoxycytidine); FIG. 30 provides the chemical structure of AZT (3'-azido-2',3'-dideoxythymidine); and FIG. 31 shows the chemical structure of ABC (cyclopropylaminopurinylcyclopentene). In each of FIGS. 29-31, the methoxy variation (O-methyl group) of nucleoside analog is circled. Further, FIG. 32 shows a cell permeant variant of d4T (IC-d4T), where "n" group is equal to 11. Derivatives include cell permeant variants of 3TC, AZT, ABC, where the nucleobase group (circled) may be replaced, in various embodiments, by 3TC, AZT, ABC, or methoxy-variants of d4T, 3TC, AZT, ABC (FIG. 29-31), or derivatives thereof.

Figure 33:
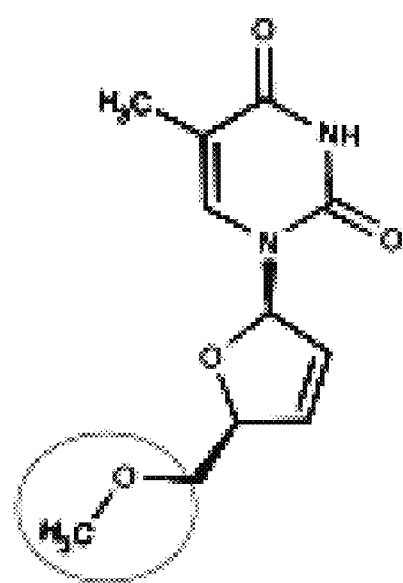
FIG. 33 provides the structure of an exemplary NRTI according to the present disclosure.

Meanwhile, FIG. 33 provides the chemical structure of an exemplary NRTI according to the present disclosure.

In certain embodiments, the present disclosure provides that NRTIs block Alu-induced RPE degeneration and/or Caspase-1 activation. For example, FIG. 34 shows a Western blot of Caspase-1 activation (p20 subunit) and IRAK4 phosphorylation in primary human RPE cells transfected with Alu RNA±d4T. FIG. 35 is a Western blot of Caspase-1 activation in human RPE cells transfected with Alu RNA±NRTIs (3TC, AZT, ABC). FIG. 36 shows that pAlu causes RPE degeneration, which is prevented by oral administration of d4T, and FIG. 37 shows that pAlu causes RPE degeneration, which is prevented by intraperitoneal administration of AZT. FIG. 36 and FIG. 37 include fundus photographs: top row; flat mounts stained for zonula occludens-1 (ZO-1; red), bottom row. Degeneration is outlined by blue arrowheads. Scale bars, 50 µm.

Figure 38:
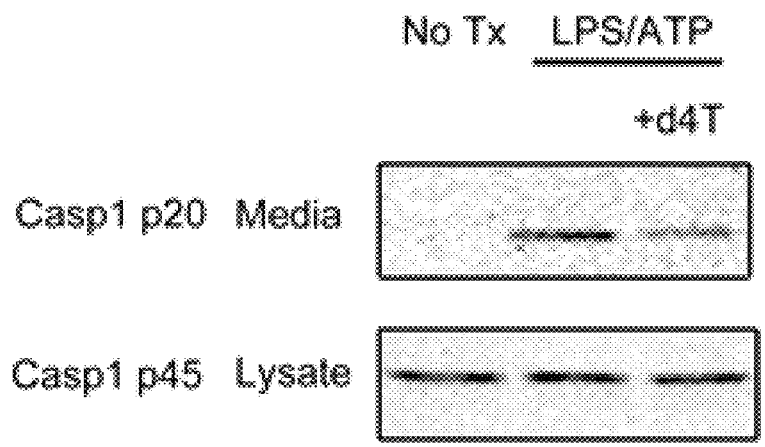
FIG. 38 illustrates that NRTIs block LPS/ATP-induced inflammasome activation. Specifically.
Figure 40:
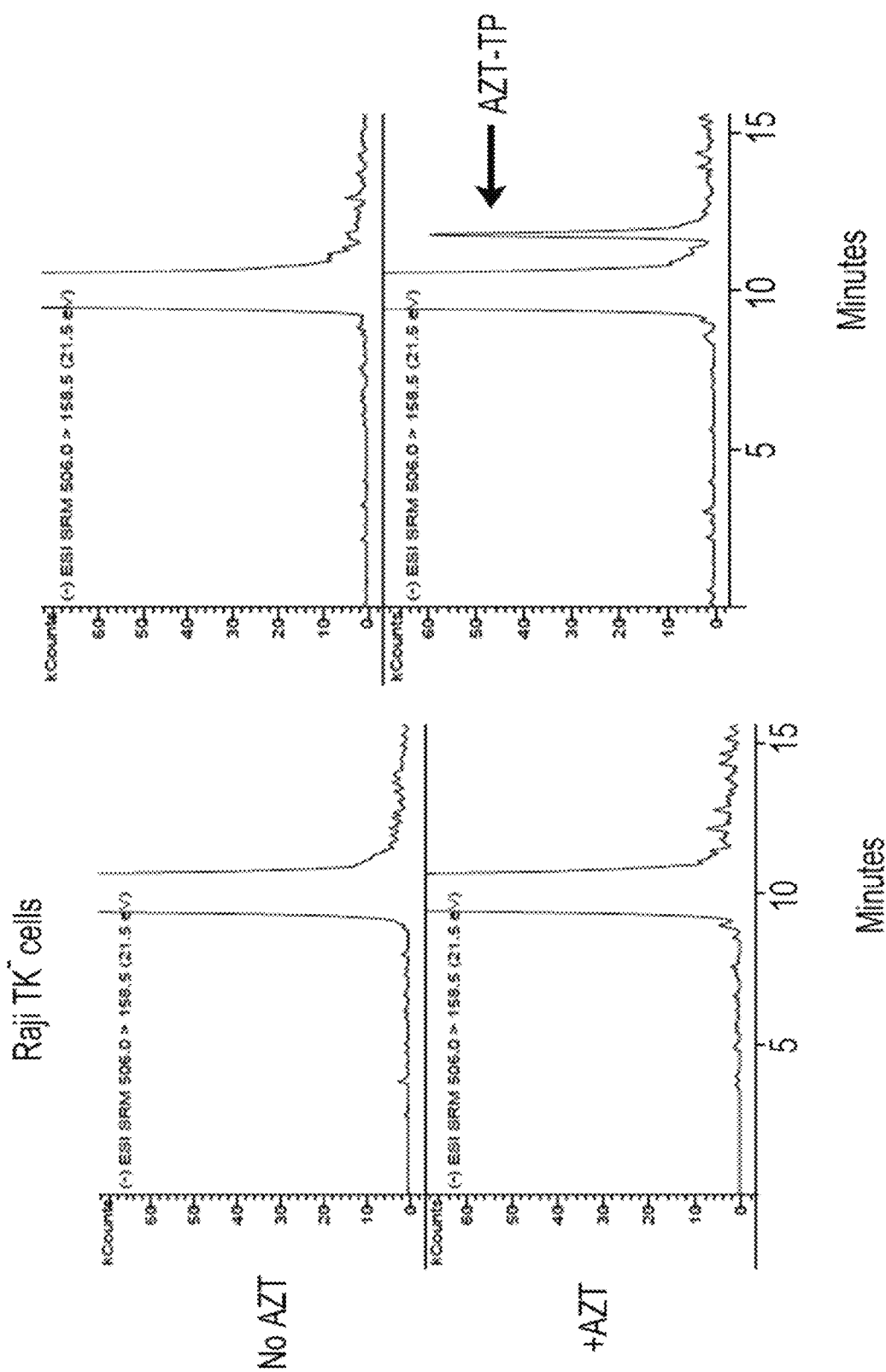
FIG. 40 presents chromatograms showing that Raji TK$^+$ cells, but not Raji TK$^-$ cells, phosphorylate AZT to AZT-triphosphate (AZT-TP) as determined by liquid chromatography-mass spectrometry (LC-MS).
Figure 41:
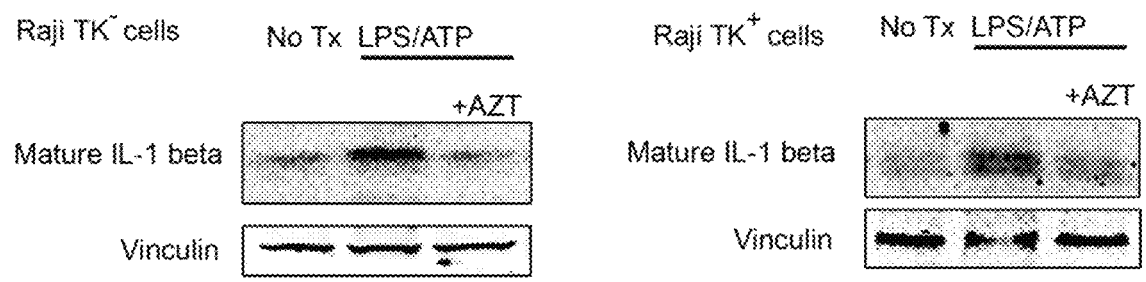
FIG. 41 shows that AZT blocks IL-1 beta activation by LPS/ATP in both Raji TK$^-$ and TK$^+$ cells, as determined by Western blot of cell lysates.

FIGS. 38-41 illustrate that NRTIs block LPS/ATP-induced inflammasome activation. FIGS. 38 and 39 show that d4T blocked Caspase-1 (FIG. 38) and IL-1 beta (FIG. 39) activation in LPS/ATP treated primary mouse bone marrow-derived macrophages as determined by western blot of cell culture media and lysate. Moreover, FIG. 40 presents chromatograms showing that Raji TK$^+$ cells, but not Raji TK$^-$ cells, phosphorylate AZT to AZT-triphosphate (AZT-TP) as determined by liquid chromatography-mass spectrometry (LC-MS). And FIG. 41 shows that AZT blocks IL-1 beta activation by LPS/ATP in both Raji TK$^-$ and TK$^+$ cells as determined by western blot of cell lysates. Representative images of n=3-4 experiments are provided in each of FIGS. 38-41.

Figure 43:
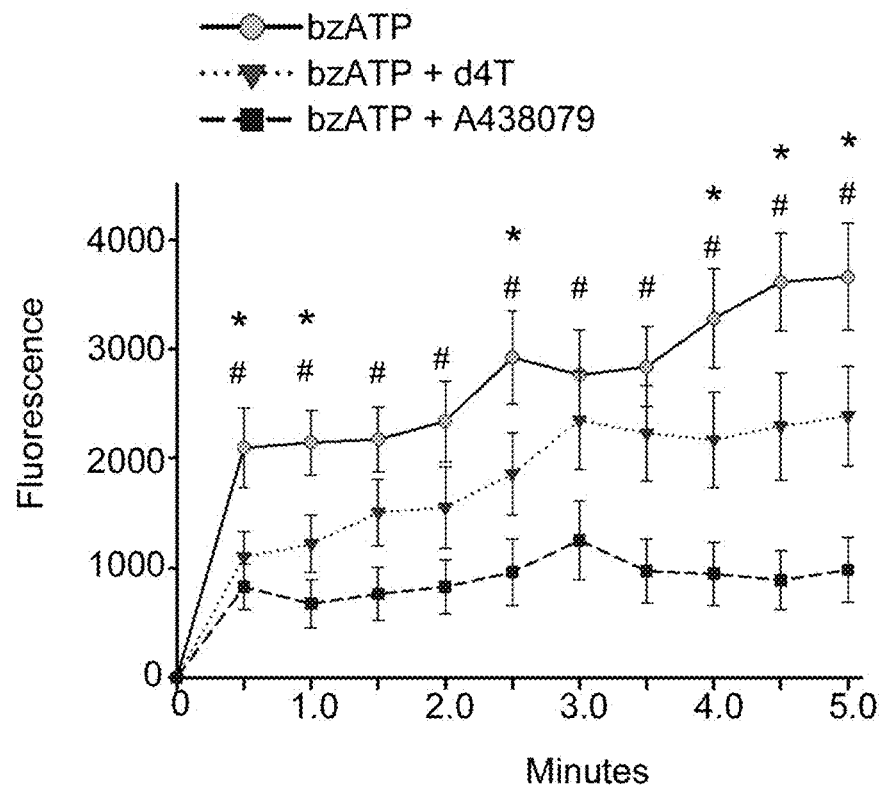
FIG. 43 provides a graph of P2X7-mediated YO-PRO-1 dye uptake (fluorescence) induced by bzATP (100 μM) in HEK293 cells stably expressing the human P2X7 receptor was inhibited by d4T and A438079 (64 μM for both drugs). Fluorescence values are baseline subtracted from cells without bzATP treatment. * bzATP vs. d4T; #bzATP vs. A438079, p<0.05 by Student-Newman Keuls post-hoc test (n=12).

In some embodiments, the present disclosure provides that NRTIs selectively block P2X7 pore function and P2X7-driven models of graft rejection and sterile liver inflammation, as shown in FIGS. 42-43. FIG. 42 is a bar graph illustrating that d4T does not block Alu-induced ATP release from primary human RPE cells (n=4). Meanwhile, FIG. 43 is a graph illustration showing that NRTIs selectively block P2X7 pore function and P2X7-driven models of graft rejection and sterile liver inflammation, providing a graph of the fluorescence (% of bzATP) over time (minutes).

And in certain exemplary embodiments, the present disclosure provides that d4T blocks Caspase-1 activation without reducing Alu RNA levels. Accordingly, FIG. 44 provides a Western blot of Caspase-1 activation (p20 subunit) and IRAK4 phosphorylation in primary mouse RPE cells transfected with Alu RNA±d4T. And FIG. 45 presents a Northern blot of biotin-UTP-labeled Alu RNA-transfected primary human RPE cells. Notably, in FIG. 45, d4T did not reduce Alu RNA levels (normalized to u6 RNA).

Figure 46:
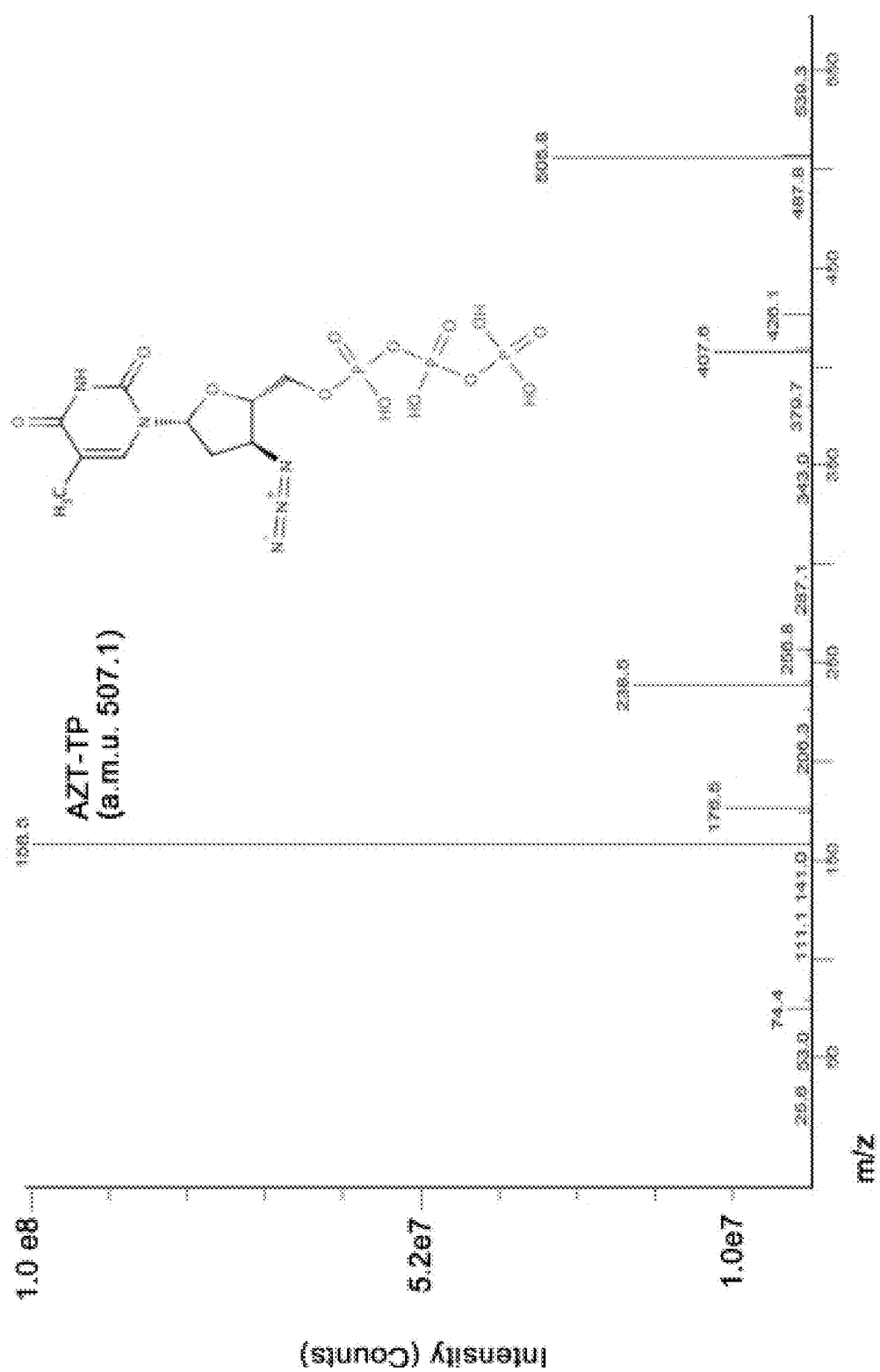
FIG. 46 provides LC-MS/MS spectra of AZT-triphosphate (AZT-TP).
Figure 47:
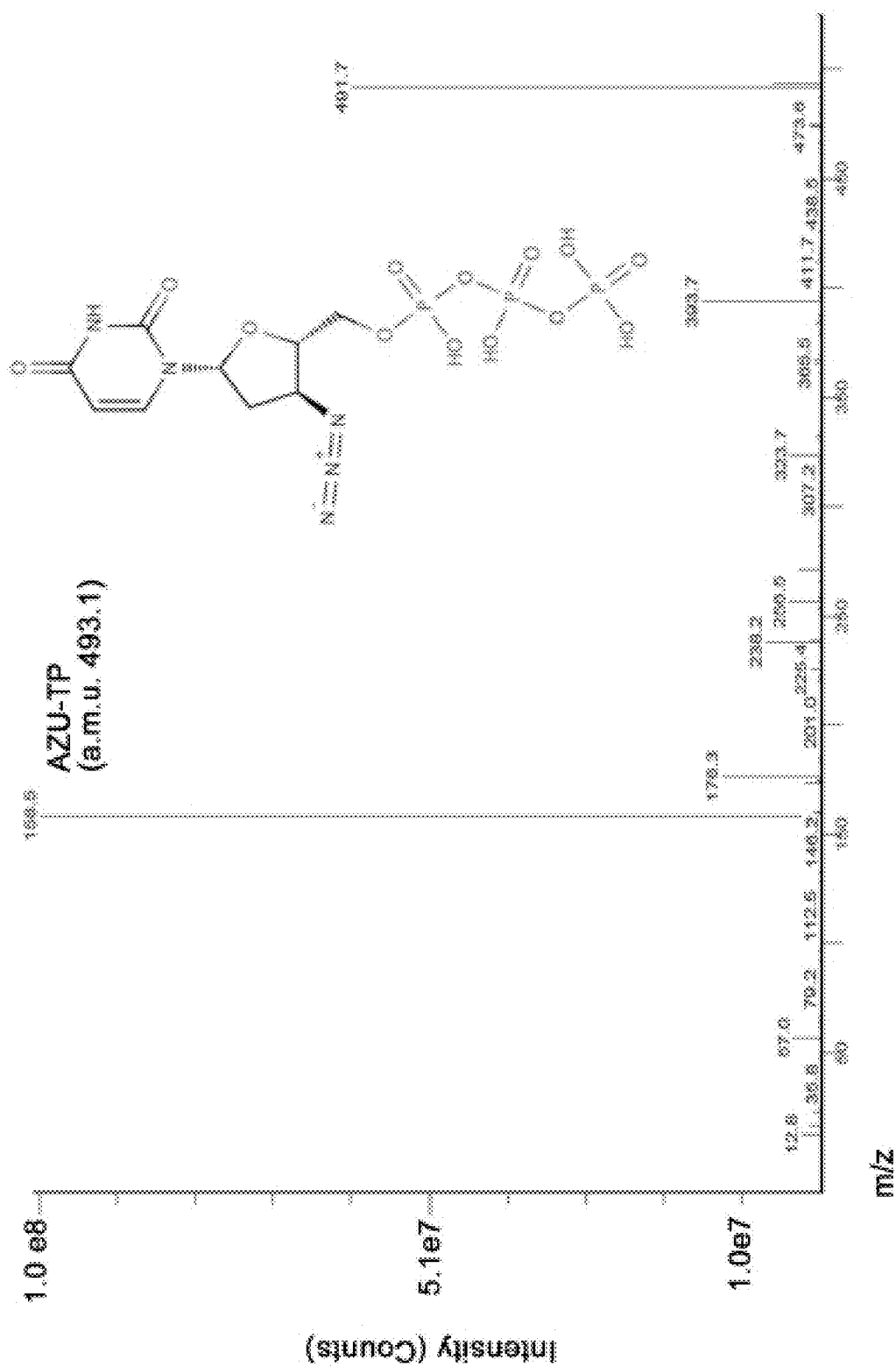
FIG. 47 provides LC-MS/MS spectra of AZU-triphosphate (AZT-TP
Figure 48:
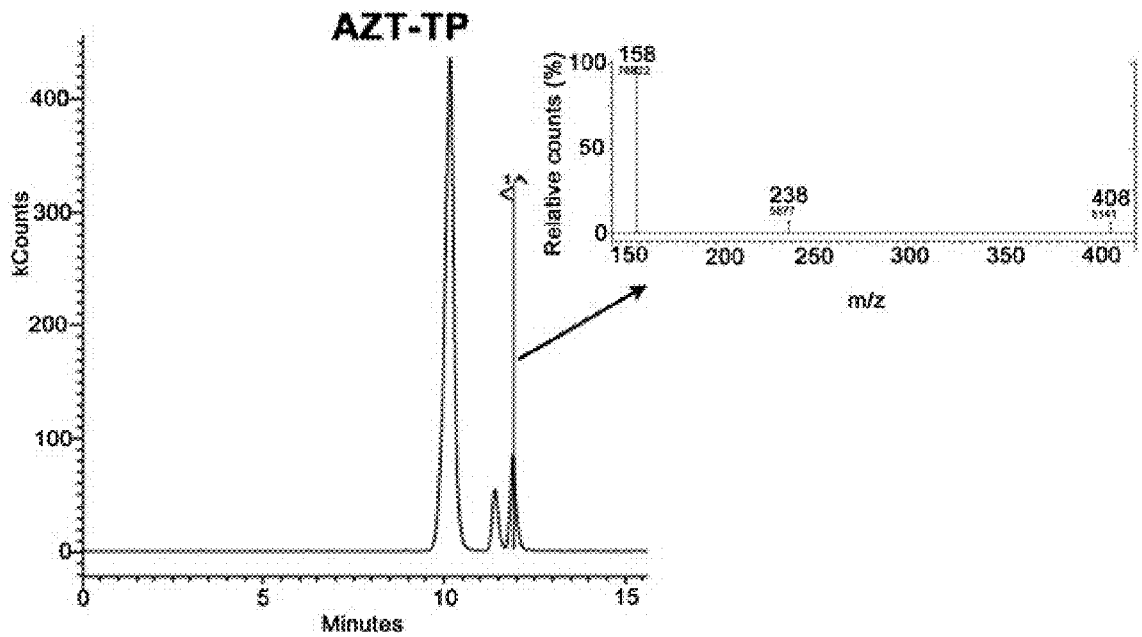
FIG. 48 shows the chromatographic separation of Raji TK$^-$ cells spiked with AZT-TP with MS spectra (inset) to confirm identity of designated peaks.
Figure 49:
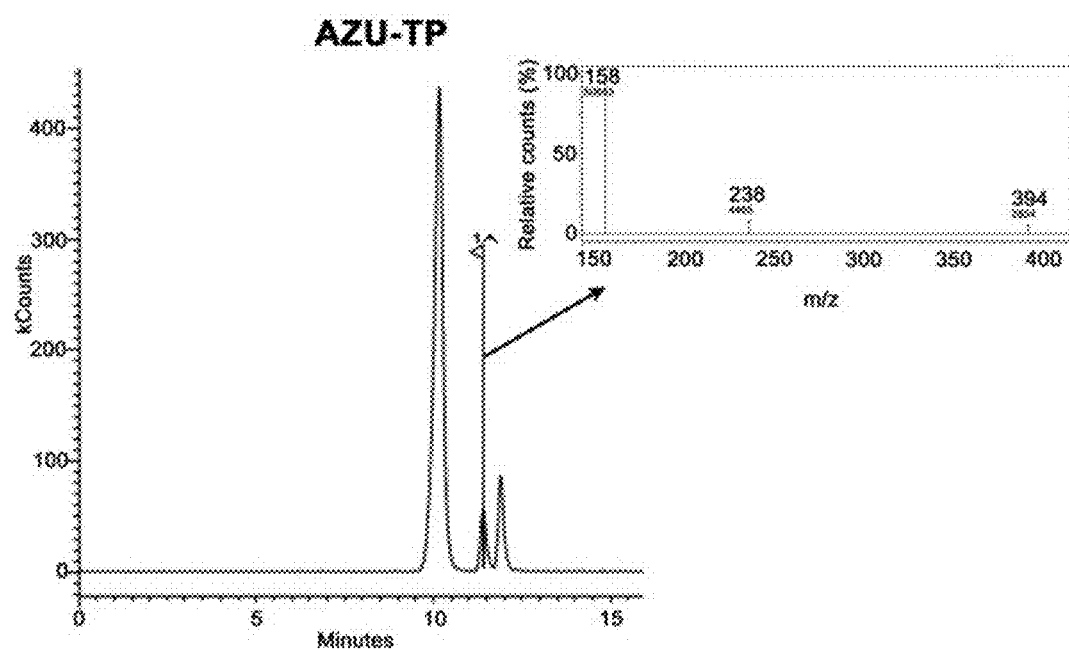
FIG. 49 shows the chromatographic separation of Raji TK$^-$ cells spiked with AZU-TP with MS spectra (inset) to confirm identity of designated peaks.

Next, FIGS. 46-47 provide LC-MS/MS spectra of AZT-triphosphate (AZT-TP, target compound; FIG. 46) and AZU-triphosphate (AZU-TP, internal standard; FIG. 47). And FIGS. 48-49 show the chromatographic separation of Raji TK$^-$ cells spiked with AZT-TP (FIG. 48) and AZU-TP (FIG. 49) with MS spectra (insets) to confirm identity of designated peaks.

Figure 50:
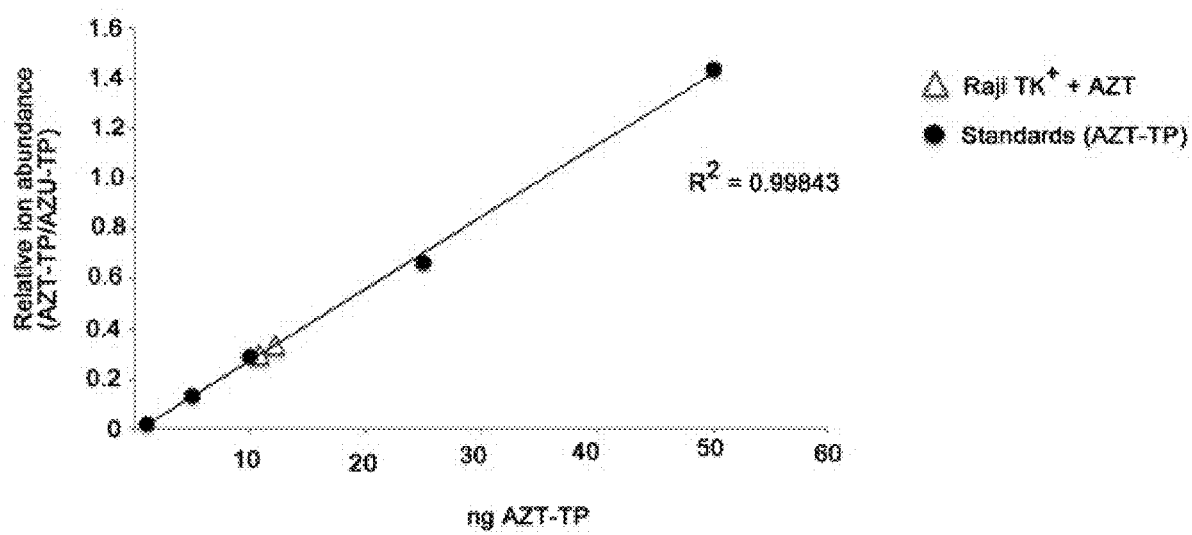
FIG. 50 is a standard curve of AZT-TP standards (black circle). As shown, Raji TK$^+$ samples treated with AZT produced AZT-TP (white triangles), whereas AZT-TP was not detectable in Raji TK$^-$ cells treated with AZT.

FIG. 50 is a standard curve of AZT-TP standards (black circle). Raji TK$^+$ samples treated with AZT produced AZT-TP (white triangles), whereas AZT-TP was not detectable in Raji TK$^-$ cells treated with AZT. FIG. 50 is representative of two experiments.

FIGS. 51-54 show that, in some exemplary embodiments, P2X7-dependent pore function mediates Alu-induced Caspase-1 activation. Indeed, FIG. 51 is a Western blot of Caspase-1 activation (p20 subunit) in primary human RPE cells transfected with Alu RNA, with short peptide) (Panx1$^{10}$, which blocks P2X7 pore function but not cation flux (vs. scrambled peptide: Scr Panx1$^{10}$); FIG. 52 is a Western blot of Caspase-1 activation (p20 subunit) in primary human RPE cells transfected with Alu RNA, with calmidazolium (FIG. 32 provides the chemical structure of IC- and EC-d4T used), which blocks P2X7 cation flux but not pore function; and FIG. 53 is a Western blot of Caspase-1 activation (p20 subunit) in primary human RPE cells transfected with Alu RNA, with cell permeable (IC), cell-impermeable (EC), or unmodified (no tag) d4T. Furthermore, FIG. 54 shows that d4T prevents pAlu-induced mitochondrial ROS generation in primary human RPE cells. In FIG. 54, mitochondrial reactive oxygen species (ROS) were visualized with MitoSox (Red) and cell nuclei with Hoechst (Blue).

One of ordinary skill in the art will recognize that additional embodiments or implementations are possible without departing from the teachings of the present disclosure or the scope of the claims which follow. This detailed description, and particularly the specific details of the exemplary embodiments and implementations disclosed herein, is given primarily for clarity of understanding, and no unnecessary limitations are to be understood therefrom, for modifications will become obvious to those skilled in the art upon reading this disclosure and may be made without departing from the spirit or scope of the claimed invention.

REFERENCES

Throughout this document various references are mentioned, including patent references. All such references are incorporated herein by reference, including the references set forth in the following list:
1. International Patent Application No. PCT/US11/38753.
2. International Patent Application No. PCT/US12/46928.

3. U.S. Provisional Patent Application Ser. No. 61/586,427.
4. U.S. Provisional Patent Application Ser. No. 61/780,105.
5. Adinolfi, E., Callegari, M. G., Ferrari, D., Bolognesi, C., Minelli, M., Wieckowski, M. R., Pinton, P., Rizzuto, R., and Di Virgilio, F. (2005). Basal activation of the P2X7 ATP receptor elevates mitochondrial calcium and potential, increases cellular ATP levels, and promotes serum-independent growth. Mol Biol Cell 16, 3260-3272.
6. Agarwal, H. K., Loethan, K., Mandal, D., Doncel, G. F., and Parang, K. (2011). Synthesis and biological evaluation of fatty acyl ester derivatives of 2',3'-didehydro-2',3'-dideoxythymidine. Bioorg Med Chem Lett 21, 1917-1921.
7. Ahmad, R., Sindhu, S. T., Toma, E., Morisset, R., and Ahmad, A. (2002). Elevated levels of circulating interleukin-18 in human immunodeficiency virus-infected individuals: role of peripheral blood mononuclear cells and implications for AIDS pathogenesis. J Virol 76, 12448-12456.
8. Ambati, J., Ambati, B. K., Yoo, S. H., Ianchulev, S., and Adamis, A. P. (2003). Age-related macular degeneration: etiology, pathogenesis, and therapeutic strategies. Sury Ophthalmol 48, 257-293.
9. Ambati, J., and Fowler, B. J. (2012). Mechanisms of age-related macular degeneration. Neuron 75, 26-39.
10. Balzarini, J., Herdewijn, P., and De Clercq, E. (1989). Differential patterns of intracellular metabolism of 2',3'-didehydro-2',3'-dideoxythymidine and 3'-azido-2',3'-dideoxythymidine, two potent anti-human immunodeficiency virus compounds. J Biol Chem 264, 6127-6133.
11. Batzer, M. A., and Deininger, P. L. (2002). Alu repeats and human genomic diversity. Nat Rev Genet 3, 370-379.
12. Cheewatrakoolpong, B., Gilchrest, H., Anthes, J. C., and Greenfeder, S. (2005). Identification and characterization of splice variants of the human P2X7 ATP channel. Biochem Biophys Res Commun 332, 17-27.
13. Cruz, C. M., Rinna, A., Forman, H. J., Ventura, A. L., Persechini, P. M., and Ojcius, D. M. (2007). ATP activates a reactive oxygen species-dependent oxidative stress response and secretion of proinflammatory cytokines in macrophages. J Biol Chem 282, 2871-2879.
14. David, D., Chevrier, D., Treilhou, M. P., Joussemet, M., Dupont, B., Theze, J., and Guesdon, J. L. (2000). IL-18 underexpression reduces IL-2 levels during HIV infection: a critical step towards the faulty cell-mediated immunity? Aids 14, 2212-2214.
15. Dewannieux, M., Esnault, C., and Heidmann, T. (2003). LINE-mediated retrotransposition of marked Alu sequences. Nat Genet 35, 41-48.
16. Dridi, S., Hirano, Y., Tarallo, V., Kim, Y., Fowler, B. J., Ambati, B. K., Bogdanovich, S., Chiodo, V. A., Hauswirth, W. W., Kugel, J. F., et al. (2012). ERK1/2 activation is a therapeutic target in age-related macular degeneration. Proc Natl Acad Sci USA 109, 13781-13786.
17. Ferrara, J. L., Levine, J. E., Reddy, P., and Holler, E. (2009). Graft-versus-host disease. Lancet 373, 1550-1561.
18. Garcia-Marcos, M., Fontanils, U., Aguirre, A., Pochet, S., Dehaye, J. P., and Marino, A. (2005). Role of sodium in mitochondrial membrane depolarization induced by P2X7 receptor activation in submandibular glands. FEBS Lett 579, 5407-5413.
19. Hazleton, J. E., Berman, J. W., and Eugenin, E. A. (2012). Purinergic receptors are required for HIV-1 infection of primary human macrophages. J Immunol 188, 4488-4495.
20. Hentze, H., Lin, X. Y., Choi, M. S., and Porter, A. G. (2003). Critical role for cathepsin B in mediating caspase-1-dependent interleukin-18 maturation and caspase-1-independent necrosis triggered by the microbial toxin nigericin. Cell Death Differ 10, 956-968.
21. Humphreys, B. D., Rice, J., Kertesy, S. B., and Dubyak, G. R. (2000). Stress-activated protein kinase/JNK activation and apoptotic induction by the macrophage P2X7 nucleotide receptor. J Biol Chem 275, 26792-26798.
22. Iannello, A., Boulassel, M. R., Samarani, S., Tremblay, C., Toma, E., Routy, J. P., and Ahmad, A. (2010). HIV-1 causes an imbalance in the production of interleukin-18 and its natural antagonist in HIV-infected individuals: implications for enhanced viral replication. J Infect Dis 201, 608-617.
23. Jankovic, D., Ganesan, J., Bscheider, M., Stickel, N., Weber, F. C., Guarda, G., Follo, M., Pfeifer, D., Tardivel, A., Ludigs, K., et al. (2013). The Nlrp3 inflammasome regulates acute graft-versus-host disease. J Exp Med 210, 1899-1910.
24. Kahlenberg, J. M., and Dubyak, G. R. (2004). Mechanisms of caspase-1 activation by P2X7 receptor-mediated K+ release. Am J Physiol Cell Physiol 286, C1100-1108.
25. Kaneko, H., Dridi, S., Tarallo, V., Gelfand, B. D., Fowler, B. J., Cho, W. G., Kleinman, M. E., Ponicsan, S. L., Hauswirth, W. W., Chiodo, V. A., et al. (2011). DICER1 deficit induces Alu RNA toxicity in age-related macular degeneration. Nature 471, 325-330.
26. Kerur, N., Hirano, Y., Tarallo, V., Fowler, B. J., Bastos-Carvalho, A., Yasuma, T., Yasuma, R., Kim, Y., Hinton, D. R., Kirschning, C. J., et al. (2013). TLR-Independent and P2X7-Dependent Signaling Mediate Alu RNA-Induced NLRP3 Inflammasome Activation in Geographic Atrophy. Invest Ophthalmol Vis Sci 54, 7395-7401.
27. Kubes, P., and Mehal, W. Z. (2012). Sterile inflammation in the liver. Gastroenterology 143, 1158-1172.
28. Lewis, W., Day, B. J., and Copeland, W. C. (2003). Mitochondrial toxicity of NRTI antiviral drugs: an integrated cellular perspective. Nat Rev Drug Discov 2, 812-822.
29. Mariathasan, S., Newton, K., Monack, D. M., Vucic, D., French, D. M., Lee, W. P., Roose-Girma, M., Erickson, S., and Dixit, V. M. (2004). Differential activation of the inflammasome by caspase-1 adaptors ASC and Ipaf. Nature 430, 213-218.
30. Mariathasan, S., Weiss, D. S., Newton, K., McBride, J., O'Rourke, K., Roose-Girma, M., Lee, W. P., Weinrauch, Y., Monack, D. M., and Dixit, V. M. (2006). Cryopyrin activates the inflammasome in response to toxins and ATP. Nature 440, 228-232.
31. Martinon, F., Burns, K., and Tschopp, J. (2002). The inflammasome: a molecular platform triggering activation of inflammatory caspases and processing of proIL-beta. Mol Cell 10, 417-426.
32. Martinon, F., Petrilli, V., Mayor, A., Tardivel, A., and Tschopp, J. (2006). Gout-associated uric acid crystals activate the NALP3 inflammasome. Nature 440, 237-241.
33. McDonald, B., Pittman, K., Menezes, G. B., Hirota, S. A., Slaba, I., Waterhouse, C. C., Beck, P. L., Muruve, D. A., and Kubes, P. (2010). Intravascular danger signals guide neutrophils to sites of sterile inflammation. Science 330, 362-366.
34. Nakahira, K., Haspel, J. A., Rathinam, V. A., Lee, S. J., Dolinay, T., Lam, H. C., Englert, J. A., Rabinovitch, M., Cernadas, M., Kim, H. P., et al. (2011). Autophagy proteins regulate innate immune responses by inhibiting the release of mitochondrial DNA mediated by the NALP3 inflammasome. Nat Immunol 12, 222-230.
35. Nykanen, A., Haley, B., and Zamore, P. D. (2001). ATP requirements and small interfering RNA structure in the RNA interference pathway. Cell 107, 309-321.
36. Ostertag, W., Roesler, G., Krieg, C. J., Kind, J., Cole, T., Crozier, T., Gaedicke, G., Steinheider, G., Kluge, N., and Dube, S. (1974). Induction of endogenous virus and of thymidine kinase by bromodeoxyuridine in cell cultures transformed by Friend virus. Proc Natl Acad Sci USA 71, 4980-4985.
37. Pelegrin, P., and Surprenant, A. (2006). Pannexin-1 mediates large pore formation and interleukin-1beta release by the ATP-gated P2X7 receptor. Embo J 25, 5071-5082.
38. Petrilli, V., Papin, S., Dostert, C., Mayor, A., Martinon, F., and Tschopp, J. (2007). Activation of the NALP3 inflammasome is triggered by low intracellular potassium concentration. Cell Death Differ 14, 1583-1589.
39. Qu, Y., Misaghi, S., Newton, K., Gilmour, L. L., Louie, S., Cupp, J. E., Dubyak, G. R., Hackos, D., and Dixit, V. M. (2011). Pannexin-1 is required for ATP release during apoptosis but not for inflammasome activation. J Immunol 186, 6553-6561.
40. Riteau, N., Baron, L., Villeret, B., Guillou, N., Savigny, F., Ryffel, B., Rassendren, F., Le Bert, M., Gombault, A., and Couillin, I. (2012). ATP release and purinergic signaling: a common pathway for particle-mediated inflammasome activation. Cell Death Dis 3, e403.
41. Sorge, R. E., Trang, T., Dorfman, R., Smith, S. B., Beggs, S., Ritchie, J., Austin, J. S., Zaykin, D. V., Vander Meulen, H., Costigan, M., et al. (2012). Genetically determined P2X7 receptor pore formation regulates variability in chronic pain sensitivity. Nat Med 18, 595-599.
42. Stylianou, E., Bjerkeli, V., Yndestad, A., Heggelund, L., Waehre, T., Damas, J. K., Aukrust, P., and Froland, S. S. (2003). Raised serum levels of interleukin-18 is associated with disease progression and may contribute to virological treatment failure in HIV-1-infected patients. Clin Exp Immunol 132, 462-466.
43. Surprenant, A., Rassendren, F., Kawashima, E., North, R. A., and Buell, G. (1996). The cytolytic P2Z receptor for extracellular ATP identified as a P2X receptor (P2X7). Science 272, 735-738.
44. Tarallo, V., Hirano, Y., Gelfand, B. D., Dridi, S., Kerur, N., Kim, Y., Cho, W. G., Kaneko, H., Fowler, B. J., Bogdanovich, S., et al. (2012). DICER1 Loss and Alu RNA Induce Age-Related Macular Degeneration via the NLRP3 Inflammasome and MyD88. Cell 149, 847-859.
45. Wilhelm, K., Ganesan, J., Muller, T., Dun, C., Grimm, M., Beilhack, A., Krempl, C. D., Sorichter, S., Gerlach, U. V., Juttner, E., et al. (2010). Graft-versus-host disease is enhanced by extracellular ATP activating P2X7R. Nat Med 16, 1434-1438.
46. Yamin, T. T., Ayala, J. M., and Miller, D. K. (1996). Activation of the native 45-kDa precursor form of interleukin-1-converting enzyme. J Biol Chem 271, 13273-13282.

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:
1. A method of treating a condition selected from graft-versus-host disease, chronic pain, proliferative vitreo-retinopathy, glaucoma, bipolar disorder, major depressive disorder, renal fibrosis, nephritis, pulmonary fibrosis, Huntington's disease, osteoporosis, chronic lymphocytic leukemia, anxiety disorder, pulmonary tuberculosis, osteoporosis in post-menopausal women, osteoporosis in fracture patients, systemic lupus erythematosus, autosomal dominant polycystic kidney disease, spinal cord injury, neuropathic pain, hypertension, varicose veins, gout, autoimmune hepatitis, graft vascular injury, atherosclerosis, thrombosis, metabolic syndrome, salivary gland inflammation, traumatic brain injury, ischemic heart disease, ischemic stroke, melanoma, neuroblastoma, prostate cancer, breast cancer, skin cancer, thyroid cancer, tubular early gastric cancer, neuroendocrine cancer, colon cancer, high-grade urothelial carcinoma, kidney clear cell carcinoma, undifferentiated ovary carcinoma, gram negative sepsis, cryopyrinopathy, keratitis, acne vulgaris, Crohn's disease, ulcerative colitis, irritable bowel syndrome, insulin resistance, obesity, hemolytic-uremic syndrome, immune complex renal disease, acute tubular injury, lupus nephritis, renal ischemia-perfusion injury, glomerulonephritis, cryoglobulinemia, systemic vasculitides, IgA nephropathy, septic shock, allergic asthma, hay fever, chronic obstructive pulmonary disease, drug-induced lung inflammation, contact dermatitis, psoriasis, scleroderma, reactive arthritis, cystic fibrosis, Sjögren's syndrome, inflammatory joint disease, non-alcoholic fatty liver disease, peri-operative inflammation in cardiac surgery, post-operative inflammation in cardiac surgery, acute organ transplant rejection, chronic organ transplant rejection, acute bone marrow transplant rejection, chronic bone marrow transplant rejection, familial cold autoinflammatory syndrome, Muckle-Wells syndrome, neonatal onset multisystem inflammatory disease, chronic infantile neurological cutaneous and articular syndrome, mucoid colon cancer, papillary intracystic breast carcinoma, and tumor angiogenesis, or a combination thereof, comprising administering to a subject in need thereof a compound selected from:
(i) a compound having the structure of formula I

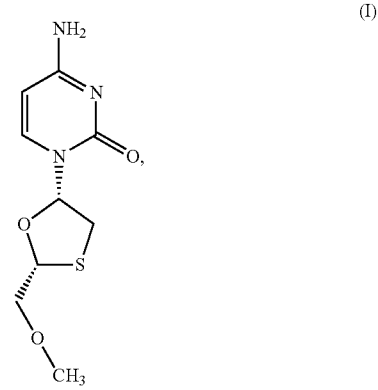

or a pharmaceutically acceptable salt thereof;

(ii) a compound having the structure of formula II

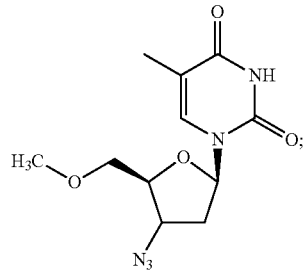
(II)

(iii) a compound having the structure of formula III, or a pharmaceutically acceptable salt thereof;

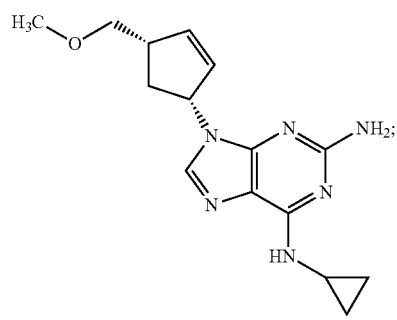
(III)

(iv) a compound having the structure of formula IV,

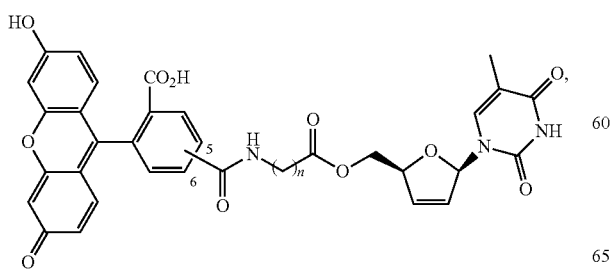
(IV)

wherein n is 10 to 20;

(v) a compound having the structure of formula V

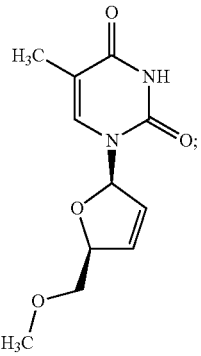
(V)

(vi) stavudine (d4T);
(vii) lamivudine (3TC);
(viii) cordycepin;
(x) abacavir (ABC); and
(xi) a combination thereof.

2. The method of claim 1, wherein the compound is selected from:

(i) the compound having the structure of formula I

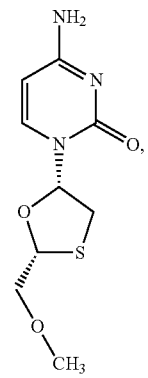 [SMILES: COC[C@@H]1O[C@H](n2ccc(N)nc2=O)CS1]
(I)

or a pharmaceutically acceptable salt thereof;

(ii) the compound having the structure of formula II

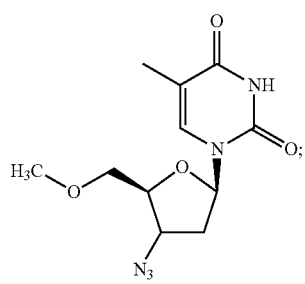
(II)

(iii) the compound having the structure of formula III, or a pharmaceutically acceptable salt thereof;

(III)

(iv) the compound having the structure of formula IV, (IV)

wherein n is 10 to 20;
(v) a compound having the structure of formula V (V)

and
(vi) a combination thereof.
3. The method of claim 1, wherein n is 11.

4. The method of claim 1, wherein the compound is selected from:
(i) the compound having the structure of formula I (I)

or a pharmaceutically acceptable salt thereof;
(ii) the compound having the structure of formula II (II)

and
(iii) a compound having the structure of formula V (V)

and
(iv) a combination thereof.

5. The method of claim 1, wherein the compound is selected from:

(i) the compound having the structure of formula I

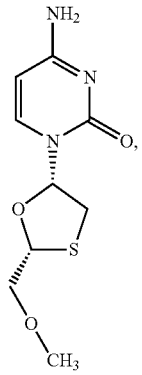

or a pharmaceutically acceptable salt thereof;

(ii) a compound having the structure of formula V

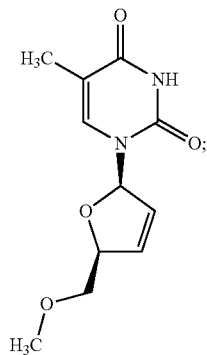

and (iii) a combination thereof.

6. The method of claim 1, wherein the compound is a compound having the structure of formula I

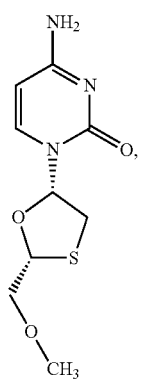

or a pharmaceutically acceptable salt thereof.

7. The method of claim 1, wherein the compound is the compound having the structure of formula II:

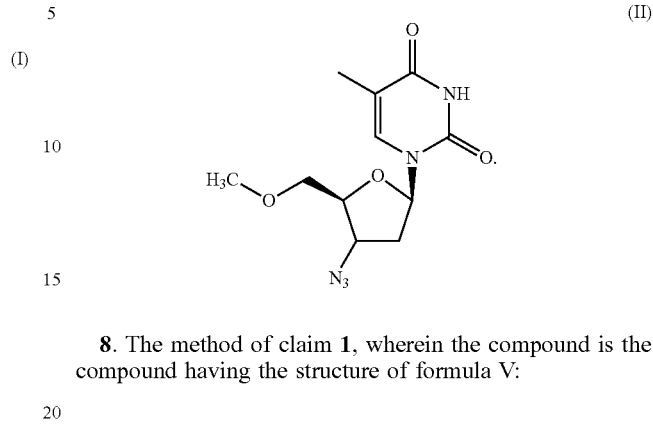

8. The method of claim 1, wherein the compound is the compound having the structure of formula V:

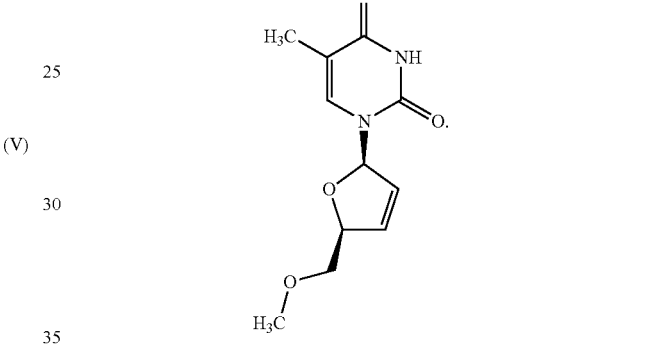

9. The method of claim 1, wherein the compound is selected from
(vi) stavudine (d4T);
(vii) lamivudine (3TC);
(viii) cordycepin;
(x) abacavir (ABC); and
(xi) a combination thereof.

10. The method of claim 1, wherein the method comprises administering a composition comprising the compound and a pharmaceutically acceptable carrier.

11. The method of claim 1, wherein the condition is selected from proliferative vitreoretinopathy, glaucoma, systemic lupus erythematosus, hypertension, gout, atherosclerosis, metabolic syndrome, traumatic brain injury, ischemic heart disease, ischemic stroke, cryopyrinopathy, Crohn's disease, ulcerative colitis, insulin resistance, obesity, inflammatory joint disease, and non-alcoholic fatty liver disease.

12. The method of claim 1, wherein the condition is selected from familial cold autoinflammatory syndrome, Muckle-Wells syndrome, and neonatal onset multisystem inflammatory disease.

13. The method of claim 1, wherein the condition is selected from proliferative vitreoretinopathy and glaucoma.

14. The method of claim 1, wherein the condition is selected from metabolic syndrome, hypertension, insulin resistance, and obesity.

15. The method of claim 1, wherein the condition is selected from atherosclerosis, traumatic brain injury, ischemic heart disease, and ischemic stroke.

16. The method of claim 1, wherein the condition is selected from Crohn's disease and ulcerative colitis.

17. The method of claim 1, wherein the condition is systemic lupus erythematosus.

18. The method of claim 1, wherein the condition is gout.

19. The method of claim 1, wherein the condition is inflammatory joint disease.

20. The method of claim 1, wherein the condition is non-alcoholic fatty liver disease.

\* \* \* \* \*